(12) United States Patent
Vogels et al.

(10) Patent No.: US 7,285,265 B2
(45) Date of Patent: Oct. 23, 2007

(54) STABLE ADENOVIRAL VECTORS AND METHODS FOR PROPAGATION THEREOF

(75) Inventors: Ronald Vogels, Linschoten (NL); Menzo Jans Emco Havenga, Alphen a/d Rijn (NL); David Adrianus Theodorus Maria Zuijdgeest, The Hague (NL)

(73) Assignee: Crucell Holland B.V., Leiden (NL)

( * ) Notice: Subject to any disclaimer, the term of this patent is extended or adjusted under 35 U.S.C. 154(b) by 453 days.

(21) Appl. No.: 10/512,602

(22) PCT Filed: Apr. 24, 2003

(86) PCT No.: PCT/EP03/50126

§ 371 (c)(1),
(2), (4) Date: Oct. 25, 2004

(87) PCT Pub. No.: WO04/001032

PCT Pub. Date: Dec. 31, 2003

(65) Prior Publication Data

US 2005/0163753 A1      Jul. 28, 2005

(30) Foreign Application Priority Data

| Apr. 25, 2002 | (WO) | PCT/NL02/00281 |
| Oct. 15, 2002 | (WO) | PCT/NL02/00656 |
| Nov. 25, 2002 | (EP) | 02102631 |

(51) Int. Cl.
- *A01N 63/00* (2006.01)
- *C12N 15/00* (2006.01)
- *C12N 15/01* (2006.01)
- *C07H 21/04* (2006.01)

(52) U.S. Cl. .................. 424/93.2; 435/320.1; 435/455; 435/456; 536/24.1

(58) Field of Classification Search ............... None See application file for complete search history.

(56) References Cited

U.S. PATENT DOCUMENTS 6,365,394 B1 * 4/2002 Gao et al. ............... 435/239

FOREIGN PATENT DOCUMENTS

| EP | 99201545.3 | 5/1999 |
| EP | 0 978 566 A2 | 2/2000 |
| WO | WO 96/26281 | 8/1996 |
| WO | WO 98/32842 | 7/1998 |
| WO | WO 98/50053 | 11/1998 |
| WO | WO 00/52186 | 9/2000 |

OTHER PUBLICATIONS

Zhang et al, Role for the Adenovirus IVa2 Protein in Packaging of Viral DNA, Journal of Virology, 2001, vol. 75 (21), p. 10446-10454.*
Tertiary structures- Biology Pages, downloaded Oct. 14, 2005.*
Smith et al, Surface point mutations that significantly alter the structure and stability of a protein's denatured state, Protein Science, 1996, vol. 5, pp. 2009-2019.*
Basler et al., "Sequence of the immunoregulatory early region 3 and flanking sequences of adenovirus type 35," Gene, 1996, pp. 249-254, vol. 170.
Flomenberg et al., "Molecular Epidemiology of Adenovirus Type 35 Infections in Immunocompromised Hosts," The Journal of Infectious Diseases, Jun. 1987, pp. 1127-1134, vol. 155, No. 6.
Flomenberg et al., "Sequence and genetic Organization of Adenovirus Type 35 Early Region 3," Journal of Virology, Nov. 1988, pp. 4431-4437, vol. 62, No. 11.
Gahery-Segard et al., "Immune response to recombinant Capsid Proteins of Adenovirus in Humans: Antifiber and Anti-Penton Base Antibodies Have a Synergistic Effect on Neutralizing Activity," Journal of Virology, Mar. 1998, pp. 2388-2397, vol. 72, No. 3.
Kang et al., "Molecular Cloning and Physical Mapping of the DNA of Human Adenovirus Type 35," Acta Microbiologica Hungarica, 1999, pp. 67-75, vol. 36, No. 1.
Krasnykh et al., "Generation of Recombinant Adenovirus Vectors with modified Fibers for Altering Viral Tropism," Journal of Virology, Oct. 1996, pp. 6839-6846, vol. 70, No. 10.
Notice of Opposition to a European Patent, Patent No. 1054064, by Cell Genesys Inc., dated Jul. 5, 2005.
Rosenfeld et al., Adenovirus-Mediated Transfer of a recombinant alpha-1-Antitrypsin Gene to the Lugn Epithelium in Vivo, Science, Apr. 19, 1991, pp. 431-434, vol. 252.
Roy et al., "Circumvention of Immunity to the Adenovirus major Coat Protein Hexon," Journal of Virology, Aug. 1998, pp. 6875-6879, vol. 72, No. 8.
Stevenson et al., "Human Adenovirus Serotypes 3 and 5 Blind to Two Different Cellular receptors via the Fiber Head Domain," Journal of Virology, May 1995, pp. 2850-2857, vol. 69, No. 5.
Stratford-Perricaudet et al., "Evaluation of the Transfer and Expression in Mice of an Enzyme-Encoding Gene Using a Human Adenovirus Vector," Human Gene Therapy, 1990, pp. 241-256, vol. 1.

\* cited by examiner

*Primary Examiner*—Joseph Woitach
*Assistant Examiner*—Maria B Marvich
(74) *Attorney, Agent, or Firm*—TraskBritt

(57) ABSTRACT

The present invention provides methods and means to increase the stability and/or the packaging capacity of recombinant adenoviruses, by overexpression of pIX in an adenoviral packaging cell, by retaining at least a part of the E1B 55K region in the recombinant adenoviral vector or by regulating pIX with a heterologous promoter. The invention further relates to methods and means for the production of such adenoviruses on complementing cell lines, wherein the early region 4 open reading frame 6 (E4-orf6) encoding nucleic acid is present in the adenovirus and wherein the E4-orf6 gene product is compatible with one or more products of the E1 gene products in the complementing cell, such that the adenoviral vector can be efficiently produced by the complementing cell.

12 Claims, 38 Drawing Sheets

Fig. 3A

Alignment of pIX proximal regions

```
1  TGAGGTACTGAAATGTGT GGGCGT GGCTTAAGGGTGGGAAAGAA TATATAA GGTGGGGGT  Ad2.SEQ
1  TGAGGTACTGAAATGTGT GGGCGT GGCTTAAGGGTGGGAAAGAA TATATAA GGTGGGGGT  Ad5.SEQ
1  TGAGG---TAAGTGGGTGGAGCTA--------GGTGGGATTATAAAA--GGC-TGGAAGT    Ad12.SEQ
1  TAGAGG--TAGGTCGAGTGAGTAGTGGGCGTGGCTAAGGT-GACTATA-AAGGCGGGTGT     Ad9.SEQ
1  TAAGGG--TAAG------GGGCGGAGCCTATTAC--AGGTATAAAGGTTGGGGT-AGAGT     Ad40.SEQ
1  TAGAG---TGAGTAGTG--------TTCTG-GGGCGGGGGA---GGACCTGCATGAGGGC    Ad4.SEQ
1  TAGAG---TGAGTAGTG--------TTCTG-GGGCGGGGGA---GGACCTGCATGAGGGC    S25.SEQ
1  TAAGG---TGAGTATTGGGA--AAACTTTG-GGGTGGGATTTTCAGAT---------GGA    Ad35.SEQ
1  TAAGG---TGAGTATTGGGA--AAACTTTG-GGGTGGGATTTTCAGAT---------GGA    Ad11.SEQ
1  TAAAG---TAAGTAGTGGGGGCAAAATGTG-GATGGGACTTTCAGGTTGGTAAGGTGGA     Ad7.SEQ

61 CTCATGTAGTTTTGTATCTGTTTTGCAGCA-GCCGCCGCC---ATG                  Ad2.SEQ
61 CTTATGTAGTTTTGTATCTGTTTTGCAGCA-GCCGCCGCCGCCATG                  Ad5.SEQ
47 CA-----ACTAAAAATTGT-TTTTGTTCT-TTTAACAGC-ACGATG                  Ad12.SEQ
57 CTTACGAGGGTCTT--TTTGCTTTTCTGCA-GA------CATCATG                  Ad9.SEQ
50 AAAAAAAAGGGAAG-----------------TTACAA----AATG                   Ad40.SEQ
46 CAGAATAACTGAAATCTGTGCTTTTCTGTGTGTTGCAGCAG-CATG                  Ad4.SEQ
46 CAGAATAACTGAAATCTGTGCTTTTCTGTGTGTTGCAGCAG-CATG                  S25.SEQ
46 CAGATTGAGTAAAAATT-TGTTT-TTTCTGTCTTGCAGCTGACATG                  Ad35.SEQ
46 CAGATTGAGTAAAAATT-TGTTT-TTTCTGTCTTGCAGCTGTCATG                  Ad11.SEQ
57 CAAATTGGGTAAAT-TT-TGTTAATTTCTGTCTTGCAGCTGCCATG                  Ad7.SEQ
```

Fig. 10

Alignment Report of Align.E1B-pIX.35-11-7.MEG, using Clustal method with Weighted residue weight table.
Friday 4 October 2002 9:32

```
1    AATAAAAATATGTTAACTGTTCACTGGTTTTTATTGCTTTTTGGGCGGGG   Ad35.E1B-pIX.SEQ
1    AATAAAAATATGTTAACTGTTCACTGGTTTTTATTGCTTTTTGGGCGGGG   Ad11.E1B-pIX.SEQ
1    AATAAAATTATGTCAGCTGCTGAGTG--TTTTATTACTTCTTGGGTGGGG   Ad7.E1B-pIX.SEQ

51   ACTCAGGTATATAAGTAGAAGCAGACCTGTGTGGTTAGCTCATAGGAGCT   Ad35.E1B-pIX.SEQ
51   ACTCAGGTATATAAGTAGAAGCAGACCTGTGTGGTTAGCTCATAGGAGCT   Ad11.E1B-pIX.SEQ
49   TCTTGGATATATAAGTAGGAGCAGATCTGTGTGGTTAGCTCACAGCAACT   Ad7.E1B-pIX.SEQ

101  GGCTTTCATCCATGGAGGTTTGGGCCATTTTGGAAGACCTTAGGAAGACT   Ad35.E1B-pIX.SEQ
101  GGCTTTCATCCATGGAGGTTTGGGCCATTTTGGAAGACCTTAGGAAGACT   Ad11.E1B-pIX.SEQ
99   TGCTGCCATCCATGGAGGTTTGGGCTATCTTGGAAGACCTCAGACAGACT   Ad7.E1B-pIX.SEQ

151  AGGCAACTGTTAGAGAGCGCTTCGGACGGAGTCTCCGGTTTTTGGAGATT   Ad35.E1B-pIX.SEQ
151  AGGCAACTGTTAGAGACGCTTCGGACGGAGTCTCCGGTTTTTGGAGATT   Ad11.E1B-pIX.SEQ
149  AGGCTACTACTAGAAAACGCCTCGGACGGAGTCTCTGGCCTTTGGAGATT   Ad7.E1B-pIX.SEQ

201  CTGGTTCGCTAGTGAATTAGCTAGGGTAGTTTTTAGGATAAAACAGGACT   Ad35.E1B-pIX.SEQ
201  CTGGTTCGCTAGTGAATTAGCTAGGGTAGTTTTTAGGATAAAACAGGACT   Ad11.E1B-pIX.SEQ
199  CTGGTTCGGTGGTGATCTAGCTAGGCTAGTGTTTAGGATAAAACAGGACT   Ad7.E1B-pIX.SEQ

251  ATAAACAAGAATTTGAAAAGTTGTTGGTAGATTGCCCAGGACTTTTTGAA   Ad35.E1B-pIX.SEQ
251  ATAAACAAGAATTTGAAAAGTTGTTGGTAGATTGCCCAGGACTTTTTGAA   Ad11.E1B-pIX.SEQ
249  ACAGGGAAGAATTTGAAAAGTTATTGGACGACATTCCAGGACTTTTTGAA   Ad7.E1B-pIX.SEQ

301  GCTCTTAATTTGGGCCATCAGGTTCACTTTAAAGAAAAAGTTTTATCAGT   Ad35.E1B-pIX.SEQ
301  GCTCTTAATTTGGGCCATCAGGTTCACTTTAAAGAAAAAGTTTTATCAGT   Ad11.E1B-pIX.SEQ
299  GCTCTTAACTTGGGCCATCAGGCTCATTTTAAGGAGAAGGTTTTATCAGT   Ad7.E1B-pIX.SEQ

351  TTTAGACTTTTCAACCCCAGGTAGAACTGCTGCTGCTGTGGCTTTTCTTA   Ad35.E1B-pIX.SEQ
351  TTTAGACTTTTCAACCCCAGGTAGAACTGCTGCTGCTGTGGCTTTTCTTA   Ad11.E1B-pIX.SEQ
349  TTTAGATTTTTCTACTCCTGGTAGAACTGCTGCTGCTGTAGCTTTTCTTA   Ad7.E1B-pIX.SEQ

401  CTTTTATATTAGATAAATGGATCCCGCAGACTCATTTCAGCAGGGGATAC   Ad35.E1B-pIX.SEQ
401  CTTTTATATTAGATAAATGGATCCCGCAGACTCATTTCAGCAGGGGATAC   Ad11.E1B-pIX.SEQ
399  CTTTTATATTGGATAAATGGATCCGCCAAACTCACTTCAGCAAGGGATAC   Ad7.E1B-pIX.SEQ

451  GTTTTGGATTTCATAGCCACAGCATTGTGGAGAACATGGAAGGTTCGCAA   Ad35.E1B-pIX.SEQ
451  GTTTTGGATTTCATAGCCACAGCATTGTGGAGAACATGGAAGGTTCGCAA   Ad11.E1B-pIX.SEQ
449  GTTTTGGATTTCATAGCAGCAGCTTTGTGGAGAACATGGAAGGCTCGCAG   Ad7.E1B-pIX.SEQ

501  GATGAGGACAATCTTAGGTTACTGGCCAGTGCAGCCTTTGGGTGTAGCGG   Ad35.E1B-pIX.SEQ
501  GATGAGGACAATCTTAGGTTACTGGCCAGTGCAGCCTTTGGGTGTAGCGG   Ad11.E1B-pIX.SEQ
499  GATGAGGACAATCTTAGATTACTGGCCAGTGCAGCCTCTGGGAGTAGCAG   Ad7.E1B-pIX.SEQ
```

Fig. 10, Cont'd

```
551 G A A T C C T G A G G C A T C C A C C G G T C A T G C C A G C G G T T C T G G A G G A G G A A C A G  Ad35.E1B-pIX.SEQ
551 G A A T C C T G A G G C A T C C A C C G G T C A T G C C A G C G G T T C T G G A G G A G G A A C A G  Ad11.E1B-pIX.SEQ
549 G G A T A C T G A G A C A C C C A C C G A C C A T G C C A G C G G T T C T G C A G G A G G A G C A G  Ad7.E1B-pIX.SEQ

601 C A A G A G G A C A A C C C G A G A G C C G G C C T G G A C C C T C C A G T G G A G G A G G C G G A  Ad35.E1B-pIX.SEQ
601 C A A G A G G A C A A C C C G A G A G C C G G C C T G G A C C C T C C A G T G G A G G A G G C G G A  Ad11.E1B-pIX.SEQ
599 C A G G A G G A C A A T C C G A G A G C C G G C C T G G A C C C T C C G G T G G A G G A G - - - - -  Ad7.E1B-pIX.SEQ

651 G T A G C T G A C T T G T C T C C T G A A C T G C A A C G G G T G C T T A C T G G A T C T A C G T C  Ad35.E1B-pIX.SEQ
651 G T A G C T G A C T T G T C T C C T G A A C T G C A A C G G G T G C T T A C T G G A T C T A C G T C  Ad11.E1B-pIX.SEQ
644 - T A G C T G A C C T G T T T C C T G A A C T G C G A C G G G T G C T T A C T A G G T C T A C G A C  Ad7.E1B-pIX.SEQ

701 C A C T G G A C G G G A T A G G G G C G T T A A G A G G G A G A G G G C A T C C A G T G G T A C T G  Ad35.E1B-pIX.SEQ
701 C A C T G G A C G G G A T A G G G G C G T T A A G A G G G A G A G G G C A T C T A G T G G T A C T G  Ad11.E1B-pIX.SEQ
693 C A G T G G A C A G A A C A G G G G A A T T A A G A G G G A G A G G A A T C C T A G T G G A A T A  Ad7.E1B-pIX.SEQ

751 A T G C T A G A T C T G A G T T G G C T T T A A G T T T A A T G A G T C G C A G A C G T C C T G A A  Ad35.E1B-pIX.SEQ
751 A T G C T A G A T C T G A G T T G G C T T T A A G T T T A A T G A G T C G C A G A C G T C C T G A A  Ad11.E1B-pIX.SEQ
743 A T T C A A G A A C C G A G T T G G C T T T A A G T T T A A T G A G C C G C A G G C G T C C T G A A  Ad7.E1B-pIX.SEQ

801 A C C A T T T G G T G G C A T G A G G T T C A G A A A G A G G G A A G G G A T G A A G T T T C T G T  Ad35.E1B-pIX.SEQ
801 A C C A T T T G G T G G C A T G A G G T T C A G A A A G A G G G A A G G G A T G A A G T T T C T G T  Ad11.E1B-pIX.SEQ
793 A C T G T T T G G T G G C A T G A G G T T C A G A G C G A A G G C A G G G A T G A A G T T T C A A T  Ad7.E1B-pIX.SEQ

851 A T T G C A G G A G A A A T A T T C A C T G G A A C A G G T G A A A A C A T G T T G G T T G G A G C  Ad35.E1B-pIX.SEQ
851 A T T G C A G G A G A A A T A T T C A C T G G A A C A G G T G A A A A C A T G T T G G T T G G A G C  Ad11.E1B-pIX.SEQ
843 A T T G C A G G A G A A A T A T T C A C T A G A A C A A C T T A A G A C C T G T T G G T T G G A A C  Ad7.E1B-pIX.SEQ

901 C A G A G G A T G A T T G G G C G G T G G C C A T T A A A A A T T A T G C C A A G A T A G C T T T G  Ad35.E1B-pIX.SEQ
901 C T G A G G A T G A T T G G G A G G T G G C C A T T A A A A A T T A T G C C A A G A T A G C T T T G  Ad11.E1B-pIX.SEQ
893 C T G A G G A T G A T T G G G A G G T G G C C A T T A G G A A T T A T G C T A A G A T A T C T C T G  Ad7.E1B-pIX.SEQ

951 A G G C C T G A T A A A C A G T A T A A G A T C A G T A G A C G G A T T A A T A T C C G G A A T G C  Ad35.E1B-pIX.SEQ
951 A G G C C T G A T A A A C A G T A T A A G A T T A C T A G A C G G A T T A A T A T C C G G A A T G C  Ad11.E1B-pIX.SEQ
943 A G G C C T G A T A A A C A A T A T A G A A T T A C T A A G A A G A T T A A T A T T A G A A A T G C  Ad7.E1B-pIX.SEQ

1001 T T G T T A C A T A T C T G G A A A T G G G G C T G A G G T G G T A A T A G A T A C T C A A G A C A  Ad35.E1B-pIX.SEQ
1001 T T G T T A C A T A T C T G G A A A T G G G G C T G A G G T G G T A A T A G A T A C T C A A G A C A  Ad11.E1B-pIX.SEQ
993  A T G C T A C A T A T C A G G A A T G G G G C A G A G G T T A T A A T A G A T A C A A G A T A  Ad7.E1B-pIX.SEQ

1051 A G A C A G T T A T T A G A T G C T G C A T G A T G G A T A T G T G G C C T G G A G T A G T C G G T  Ad35.E1B-pIX.SEQ
1051 A G G C A G T T A T T A G A T G C T G C A T G A T G G A T A T G T G G C C T G G G G T A G T C G G T  Ad11.E1B-pIX.SEQ
1043 A A G C A G C T T T T A G A T G T T G T A T G A T G G G T A T G T G G C C A G G G G T T G T C G G C  Ad7.E1B-pIX.SEQ
```

Fig. 10, Cont'd

```
1101 A T G G A A G C A G T C A C T T T T G T A A A T G T T A A G T T T A G G G G A G A T G G T T A T A A  Ad35.E1B-pIX.SEQ
1101 A T G G A A G C A G T[A]A C T T T T G T A A A T G T T A A G T T T A G G G G A G A T G G T T A T A A  Ad11.E1B-pIX.SEQ
1093 A T G G A A G C A[A]T[A]A C[A C]T T[A]T[G]A A T[A]T T A[G]G T T T A G[A]G G[G]G A T G G[G]T A T A A  Ad7.E1B-pIX.SEQ

1151 T G G A A T A G T G T T T A T G G C C A A T A C C A A A C T T A T A T T G C A T G G T T G T A G C T  Ad35.E1B-pIX.SEQ
1151 T G G A A T A G T G T T T A T G G C C A A T A C C A A A C T T A T A T T G C A T G G T T G T A G C T  Ad11.E1B-pIX.SEQ
1143 T G G[C]A T[T]G T[A]T T T A T G G C[T]A A C A C[T]A A G C T G A T[T C T A]C A T G G T T G T A G C T  Ad7.E1B-pIX.SEQ

1201 T T T T T G G T T T C A A C A A T A C C T G T G T A G A T G C C T G G G G A C A G G T T A G T G T A  Ad35.E1B-pIX.SEQ
1201 T T T T T G G T T T C A A C A A T A C C T G T G T A G A T G C C T G G G G A C A G G T T A G T G T A  Ad11.E1B-pIX.SEQ
1193 T T T T T G G[G]T T[T]A A[T]A A T A C[G]T G T G T A G A[A]G C[T]T G G G G[G]C A[A]G T T A G T G T[G]  Ad7.E1B-pIX.SEQ

1251 C G G G G G T G T A G T T T C T A T G C G T G T T G G A T T G C C A C A G C T G G C A G A A C C A A  Ad35.E1B-pIX.SEQ
1251 C G G G G[A]T G T A G T T T C T A T G C G T G T T G G A T T G C C A C A G C T G G C A G A A C C A A  Ad11.E1B-pIX.SEQ
1243 [A]G G G G[T]T G T A G T T T[T]T A T G C[A]T G[C]T G G A T T G C[A]A C A[T]C[A]G G[T]A G[G G T G]A A  Ad7.E1B-pIX.SEQ

1301 G A G T C A A T T G T C T C T G A A G A A A T G C A T A T T C C A A A G A T G T A A C C T G G G C A  Ad35.E1B-pIX.SEQ
1301 G A G T C A A T T G T C T C T G A A G A A A T G C A T A T T[T]C A A A G A T G T A A C C T G G G C A  Ad11.E1B-pIX.SEQ
1293 G A G T C A[G]T T G T C T[G]T G A A G A A A T G C A T[G]T T[T G]A G A G A T G T A A[T]C T[T]G G C A  Ad7.E1B-pIX.SEQ

1351 T T C T G A A T G A A G G C G A A G C A A G G G T C C G T C A C T G C G C T T C T A C A G A T A C T  Ad35.E1B-pIX.SEQ
1351 T T C T G A A T G A A G G C G A A G C A A G G G T C C G[C]C A C T G C G C T T C T A C A G A T A C T  Ad11.E1B-pIX.SEQ
1343 T[A]C T G A A T G A A G G[T]G A A G C A A G G G T C C G[C]C A C T G C G C[A G]C T A C A G A[A]A C T  Ad7.E1B-pIX.SEQ

1401 G G A T G T T T T A T T T T A A T T A A G G G A A A T G C C A G C G T A A A G C A T A A C A T G A T  Ad35.E1B-pIX.SEQ
1401 G G A T G T T T T A T T T T[G]A T T A A G G G A A A T G C C A G C G T A A A G C A T A A C A T G A T  Ad11.E1B-pIX.SEQ
1393 G[C C]T G[C]T T[C]A T T[C]T A A T[A]A A G G G A A A T G C C A G[T]G[T G]A A G C A T A A[T]A T G A T  Ad7.E1B-pIX.SEQ

1451 T T G T G G T G C T T C C G A T G A G A G G C C T T A T C A A A T G C T C A C T T G T G C T G G T G  Ad35.E1B-pIX.SEQ
1451 T T G[C]G G T G C T T C C G A T G A G A G G C C T T A T C A A A T G C T C A C T T G T G C T G G T G  Ad11.E1B-pIX.SEQ
1443 [C]T G T G G[A C A]T T C[G]G A T G A G A G G C C T T A T C A[G]A T G C T[A]A C[C]T G[C]G C T G G T G  Ad7.E1B-pIX.SEQ

1501 G G C A T T G T A A T A T G C T G G C T A C T G T G C A T A T T G T T T C C C A T C A A C G C A A A  Ad35.E1B-pIX.SEQ
1501 G G C A T T G T A A T A T G C T G G C T A C T G T G C A T A T T G T T T C C C A T C A A C G C A A A  Ad11.E1B-pIX.SEQ
1493 G[A]C A T T G[C]A A T A T[T]C T[T]G C T A C[C]G T G C A T A T[C]G T T T C[A]C A T[G C]A C G C A A[G]  Ad7.E1B-pIX.SEQ

1551 A A A T G G C C T G T T T T T G A T C A C A A T G T G T T G A C C A A G T G C A C C A T G C A T G C  Ad35.E1B-pIX.SEQ
1551 A A A T G G C C T G T T T T T G A T C A C A A T G T G[A]T G A C[G]A A G T G[T]A C C A T G C A T G C  Ad11.E1B-pIX.SEQ
1543 A A A T G G C C T G T[A]T T T G A[A]C A[T]A A T G T G[A]T[T]A C C A A G T G C A C C A T G C A T[A T]  Ad7.E1B-pIX.SEQ

1601 A G G T G G G C G T A G A G G A A T G T T T A T G C C T T A C C A G T G T A A C A T G A A T C A T G  Ad35.E1B-pIX.SEQ
1601 A G G T G G G C G T A G A G G A A T G T T T A T G C C T T A C C A G T G T A A C A T G A A T C A T G  Ad11.E1B-pIX.SEQ
1593 A G G T G G[T]C G[C]A G[G]G G A A T G T T T A T G C C T T A C C A G T G T A A C A T G A A T C A T G  Ad7.E1B-pIX.SEQ
```

Fig. 10, Cont'd

```
1651 T G A A A G T G T T G T T G G A A C C A G A T G C C T T T T C C A G A A T G A G C C T A A C A G G A  Ad35.E1B-pIX.SEQ
1651 T G A A A G T G T T G T T G G A A C C A G A T G C C T T T T C C A G A A T G A G C C T A A C A G G A  Ad11.E1B-pIX.SEQ
1643 T G A A G G T A A T G T T G G A A C C A G A T G C C T T T T C C A G A G T G A G C G T A A C A G G A  Ad7.E1B-pIX.SEQ

1701 A T C T T T G A C A T G A A C A C G C A A A T C T G G A A G A T C C T G A G G T A T G A T G A T A C  Ad35.E1B-pIX.SEQ
1701 A T T T T T G A C A T G A A C A T G C A A A T C T G G A A G A T C C T G A G G T A T G A T G A T A C  Ad11.E1B-pIX.SEQ
1693 A T C T T T G A T A T G A A T A T T C A A C T A T G G A A G A T C C T G A G A T A T G A T G A C A C  Ad7.E1B-pIX.SEQ

1751 G A G A T C G A G G G T G C G C G C A T G C G A A T G C G G A G G C A A G C A T G C C A G G T T C C  Ad35.E1B-pIX.SEQ
1751 G A G A T C G A G G G T A C G C G C A T G C G A A T G C G G A G G C A A G C A T G C C A G G T T C C  Ad11.E1B-pIX.SEQ
1743 T A A A C C A A G G G T G C G C G C A T G C G A A T G C G G A G G C A A G C A T G C T A G A T T C C  Ad7.E1B-pIX.SEQ

1801 A G C C G G T G T G T G T A G A T G T G A C C G A A G A T C T C A G A C C G G A T C A T T T G G T T  Ad35.E1B-pIX.SEQ
1801 A G C C G G T G T G T G T A G A T G T G A C T G A A G A T C T C A G A C C G G A T C A T T T G G T T  Ad11.E1B-pIX.SEQ
1793 A G C C G G T G T G C G T G G A T G T G A C T G A A G A C C T G A G G C C C G A T C A T T T G G T G  Ad7.E1B-pIX.SEQ

1851 A T T G C C C G C A C T G G A G C A G A G T T C G G A T C C A G T G G A G A A G A A A C T G A C T A  Ad35.E1B-pIX.SEQ
1851 A T T G C C C G C A C T G G A G C A G A G T T C G G A T C C A G T G G A G A A G A A A C T G A C T A  Ad11.E1B-pIX.SEQ
1843 C T T G C C T G C A C T G G A G C G G A G T T C G G T T C T A G T G G T G A A G A A A C T G A C T A  Ad7.E1B-pIX.SEQ

1901 A G G T G A G T A T T G G G A - - A A A C T T T G G G G T G G G A T T T T C A G - - - - - - - - - A  Ad35.E1B-pIX.SEQ
1901 A G G T G A G T A T T G G G A - - A A A C T T T G G G G T G G G A T T T T C A G - - - - - - - - - A  Ad11.E1B-pIX.SEQ
1893 A A G T A A G T A G T G G G G G C A A A A T G T G G A T G G G G A C T T T C A G G T T G G T A A G G  Ad7.E1B-pIX.SEQ

1940 T G G A C A G A T T G A G T A A A A A T T T G T T T T T T C T G T C T T G C A G C T G A C A T G A G  Ad35.E1B-pIX.SEQ
1940 T G G A C A G A T T G A G T A A A A A T T T G T T T T T T C T G T C T T G C A G C T G T C A T G A G  Ad11.E1B-pIX.SEQ
1943 T G G A C A A A T T G G G T A A A T T T T G T T A A T T T C T G T C T T G C A G C T G C C A T G A G  Ad7.E1B-pIX.SEQ

1990 T G G A A A T G C T T C T T T T A A G G G G G G A G T C T T C A G C C C T T A T C T G A C A G G G C  Ad35.E1B-pIX.SEQ
1990 T G G A A A C G C T T C T T T T A A G G G G G G A G T C T T C A G C C C T T A T C T G A C A G G G C  Ad11.E1B-pIX.SEQ
1993 T G G A A G C G C T T C T T T T G A G G G G G G A G T A T T T A G C C C T T A T C T G A C G G G C A  Ad7.E1B-pIX.SEQ

2040 G T C T C C C A T C C T G G G C A G G A G T T C G T C A G A A T G T T A T G G G A T C T A C T G T G  Ad35.E1B-pIX.SEQ
2040 G T C T C C C A T C C T G G G C A G G A G T T C G T C A G A A T G T T A T G G G A T C T A C T G T G  Ad11.E1B-pIX.SEQ
2043 G G C T C C C A C C A T G G G C A G G A G T T C G T C A G A A T G T C A T G G G A T C C A C T G T G  Ad7.E1B-pIX.SEQ

2090 G A T G G A A G A C C C G T T C A A C C C G C C A A T T C T T C A A C G C T G A C C T A T G C T A C  Ad35.E1B-pIX.SEQ
2090 G A T G G A A G A C C C G T C C A A C C C G C C A A T T C T T C A A C G C T G A C C T A T G C T A C  Ad11.E1B-pIX.SEQ
2093 G A T G G G A G A C C C G T C C A G C C C G C C A A T T C C T C A A C G C T G A C C T A T G C C A C  Ad7.E1B-pIX.SEQ

2140 T T T A A G T T C T T C A C C T T T G G A C G C A G C T G C A G C C G C T G C C G C C G C C T C T G  Ad35.E1B-pIX.SEQ
2140 T T T A A G T T C T T C A C C T T T G G A C G C A G C T G C A G C T G C C G C C G C C G C T T C T G  Ad11.E1B-pIX.SEQ
2143 T T T G A G T T C G T C A C C A T T G G A T G C A G C T G C A G C C G C C G C C G C T A C - - - T G  Ad7.E1B-pIX.SEQ
```

Fig. 10, Cont'd

```
2190 T C G C C G C T A A C A C T G T G C T T G G A A T G G G T T A C T A T G G A A G C A T C G T G G C T  Ad35.E1B-pIX.SEQ
2190 T T G C C G C T A A C A C T G T G C T T G G A A T G G G T T A C T A T G G A A G C A T C A T G G C T  Ad11.E1B-pIX.SEQ
2190 C T G C C G C C A A C A C C A T C C T T G G A A T G G G C T A T T A C G G A A G C A T T G T T G C C  Ad7.E1B-pIX.SEQ

2240 A A T T C C A C T T C C T C T A A T A A C C C T T C T A C A C T G A C T C A G G A C A A G T T A C T  Ad35.E1B-pIX.SEQ
2240 A A T T C C A C T T C C T C T A A T A A C C C T T C T A C C C T G A C T C A G G A C A A G T T A C T  Ad11.E1B-pIX.SEQ
2240 A A T T C C A G T T C C T C T A A T A A T C C T T C A A C C C T G G C T G A G G A C A A G C T A C T  Ad7.E1B-pIX.SEQ

2290 T G T C C T T T T G G C C C A G C T G G A G G C T T T G A C C C A A C G T C T G G G T G A A C T T T  Ad35.E1B-pIX.SEQ
2290 T G T C C T T T T G G C C C A G C T G G A G G C T T T G A C C C A A C G T C T G G G T G A A C T T T  Ad11.E1B-pIX.SEQ
2290 T G T C T C T T G G C T C A G C T C G A G G C C T T A A C C C A A C G C T T A G G C G A A C T G T  Ad7.E1B-pIX.SEQ

2340 C T C A G C A G G T G G C C G A G T T G C G A G T A C A A A C T G A G T C T G C T G T C G G C A C G  Ad35.E1B-pIX.SEQ
2340 C T C A G C A G G T G G T C G A G T T G C G A G T A C A A A C T G A G T C T G C T G T C G G C A C G  Ad11.E1B-pIX.SEQ
2340 C T A A G C A G G T G G C C C A G T T G C G T G A G C A A A C T G A G T C T G C T G T T G C C A C A  Ad7.E1B-pIX.SEQ

2390 G C A A A G T C T A A A T A A A A A A A T T C C A G A A T C A A T G A A T A A A              Ad35.E1B-pIX.SEQ
2390 G C A A A G T C T A A A T A A A A A A A - T C C A G A A T C A A T G A A T A A A              Ad11.E1B-pIX.SEQ
2390 G C A A A G T C T A A A T A A G A - - - T C T C A - A A T C A A T A A A T A A A              Ad7.E1B-pIX.SEQ
```

Decoration 'Decoration #1': Box residues that differ from Ad35.E1B-pIX.SEQ.

Fig. 21

```
1   MTTSGVPFGMTLRPTRSRLSRRTPYSRDRLPPFET-ETRATILEDHPLLP  Ad5.E4-ORF6.PRO
1   MTTSGVPFGMTLRPTRSRLSRRTPYSRDRLPPFET-ETRATILEDHPLLP  Orf6 aaseq in Ad35.PR.5Orf6.PRO
1   MSGSNSIMTR-LRARSTSCARHHPYTRAQLPRCENETRASMTEDHPLLP   Ad35.E4-ORF6.PRO 50  ECNTLTMHNVSYVRGLPCSVGFTLIQEWVPHDMVLTREELVILRKCMHV   Ad5.E4-ORF6.PRO
50  ECNTLTMHNVSYVRGLPCSVGFTLIQEWVPHDMVLTREELVILRKCMHV   Orf6 aaseq in Ad35.PR.5Orf6.PRO
50  DCDTMTHHSVSCVRGLPCSASFTVLQELPIPWDMFLNPEELKIMRRCMHL  Ad35.E4-ORF6.PRO 100 CLCCANIDIMTSMMIHGYESWALHCHCSSPGSLQCIAGGQVLASWFRMVV  Ad5.E4-ORF6.PRO
100 CLCCANIDIMTSMMIHGYESWALHCHCSSPGSLQCIAGGQVLASWFRMVV  Orf6 aaseq in Ad35.PR.5Orf6.PRO
100 CLCCATIDIFHSQVIHGRENWVLHCHCNQQGSLQCMAGGAVLAVWFRKVI  Ad35.E4-ORF6.PRO 150 DGAMFNQRFIWYREVVNYNMPKEVMFMSSVFMRGRHLIYLRLWYDGHVGS  Ad5.E4-ORF6.PRO
150 DGAMFNQRFIWYREVVNYNMPKEVMFMSSVFMRGRHLIYLRLWYDGHVGS  Orf6 aaseq in Ad35.PR.5Orf6.PRO
150 LGCMINQRCPWYRQIVNMHMPKEIMYVGSVFLRERHLIYIKLWYDGHAGA  Ad35.E4-ORF6.PRO 200 VVPAMSFGYSALHCGILNNIVVLCCSYCADLSEIRVRCCARRTRRLMLRA  Ad5.E4-ORF6.PRO
200 VVPAMSFGYSALHCGILNNIVVLCCSYCADLSEIRVRCCARRTRRLMLRA  Orf6 aaseq in Ad35.PR.5Orf6.PRO
200 IISDMSPGWSAFNYGLLNNIVIMCCTYCKDLSEIRMRCCAHRTRKLMLRA  Ad35.E4-ORF6.PRO 250 VRIIAEETTA--MLYSCRTERRRQQFIRALLQHHRPILMHDYDS---TPM  Ad5.E4-ORF6.PRO
250 VRIIAEETTA--MLYSCRTERRRQQFIRALLQHHRPILMHDYDS---TPM  Orf6 aaseq in Ad35.PR.5Orf6.PRO
250 IKIMLQETVDPDPINSSRTERRRQRLLVGLMRHNRPIPFSDYDSHRSSSR  Ad35.E4-ORF6.PRO
```

Decoration 'Decoration #1': Box residues that differ from Ad5.E4-ORF6.PRO.

Fig. 22

```
1   M T T S G V P F G M T L R P T R S R L S R R T P Y S R D R L P P F E T - E T R A   Ad5.E4-ORF6+7.PRO
1   M T T S G V P F G M T L R P T R S R L S R R T P Y S R D R L P P F E T - E T R A   Orf6+7 aaseq in Ad35.PR5Orf6.PRO
1   M S G S N - S I M T R L R A R S T S C A R H H P Y T R A Q L P R C E E N E T R A   Ad35.E4-ORF6+7.pro 40  T I L E D H P L L P E C N T L T M H N A W T S P S P P V K Q P Q V G Q Q P V A Q   Ad5.E4-ORF6+7.PRO
40  T I L E D H P L L P E C N T L T M H N A W T S P S P P V K Q P Q V G Q Q P V A Q   Orf6+7 aaseq in Ad35.PR5Orf6.PRO
40  S M T E D H P L L P D C D T M T M H S M T V I Q T P - - - - - - - - - E S H P Q   Ad35.E4-ORF6+7.pro 80  Q L D S D M N L S E L P G E F I N I T D E R L A R Q E T V W N I T P K N M S V T   Ad5.E4-ORF6+7.PRO
80  Q L D S D M N L S E L P G E F I N I T D E R L A R Q E T V W N I T P K N M S V T   Orf6+7 aaseq in Ad35.PR5Orf6.PRO
71  Q L D C E S A L K D Y R D G F L S I T D P R L A R S E T V W N V E S K T M S I S   Ad35.E4-ORF6+7.pro 120 H D M M L F K A S R G E R T V Y S V C W E G G G R L N T R V L                     Ad5.E4-ORF6+7.PRO
120 H D M M L F K A S R G E R T V Y S V K W E G G G K I T T R I L                     Orf6+7 aaseq in Ad35.PR5Orf6.PRO
111 N G I Q M F K A V R G E R L V Y S V K W E G G G K I T T R I L                     Ad35.E4-ORF6+7.pro
```

Decoration 'Decoration #1': Box residues that differ from Ad5.E4-ORF6+7.PRO.

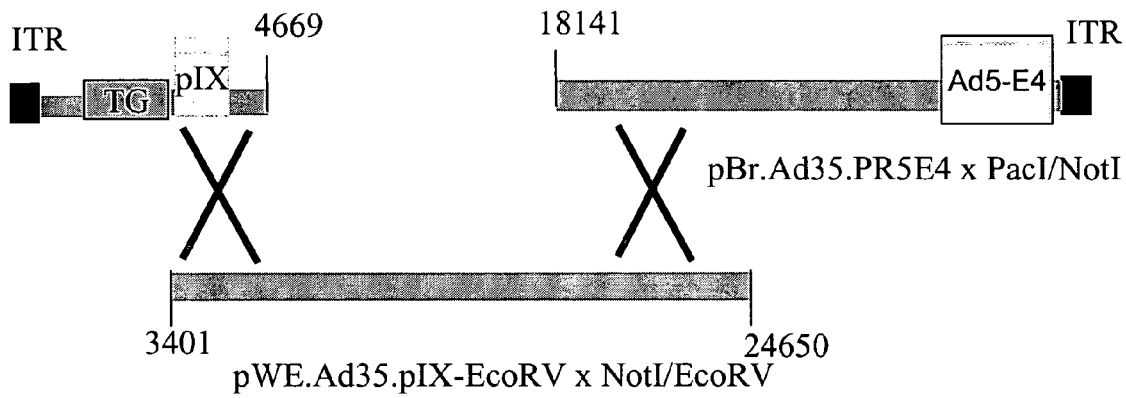
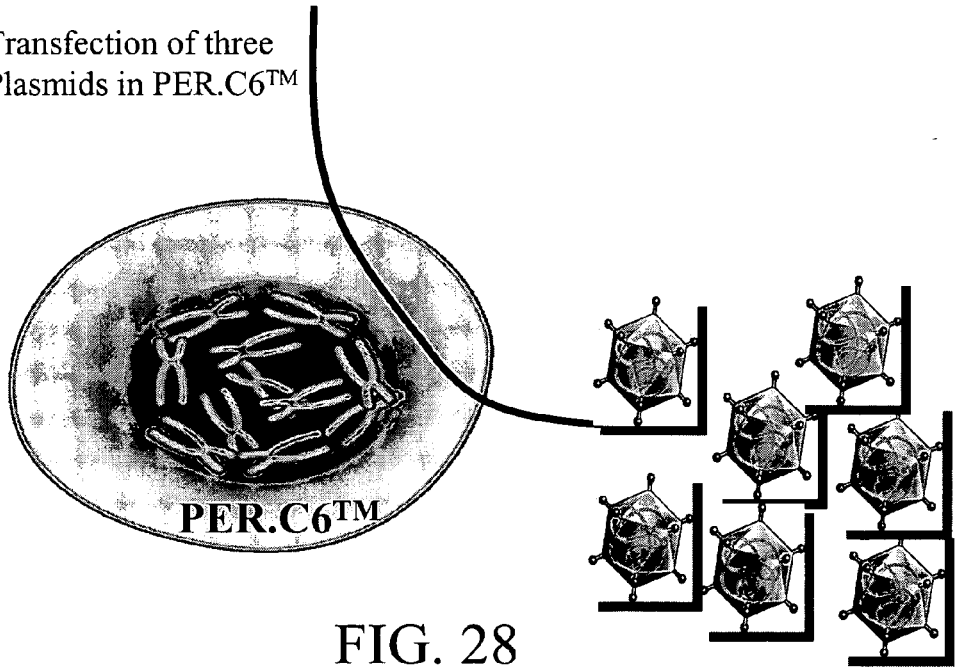
FIG. 28

STABLE ADENOVIRAL VECTORS AND METHODS FOR PROPAGATION THEREOF

CROSS-REFERENCE TO RELATED APPLICATIONS

This application is a national phase entry under 35 U.S.C. § 371 of International Patent Application PCT/EP03/50126, filed Apr. 24, 2003, published in English as International Patent Publication WO 04/001032 on Dec. 31, 2003, which claims the benefit under 35 U.S.C. § 119 of International Patent Application PCT/NL02/00281, filed Apr. 25, 2002, International Patent Application PCT/NL02/00656, filed Oct. 15, 2002, and European Patent Application EP02102631.5, filed Nov. 25, 2002.

TECHNICAL FIELD

The invention relates to the field of biotechnology and medicine; more in particular, the invention relates to recombinant adenoviral vectors and the use thereof.

BACKGROUND

Human adenoviruses are non-enveloped icosahedral particles of ~60 to 90 nM size. To date, 51 serotypes have been identified that are subdivided into six subgroups based on hemagglutination properties and sequence homology (Francki et al., 1991). The genome has a length of 34 to 36 kb and is flanked on both sites by inverted terminal repeat sequences (ITR). The virus infectious cycle is divided into an early and a late phase. In the early phase—(six to eight hours after infection), the virus is uncoated and the genome transported to the nucleus, after which the early gene regions E1-E4 become transcriptionally active.

The early region-1 (E1) contains two transcription regions named E1A and E1B. The E1A region encodes two major proteins that are involved in modification of the host-cell cycle and activation of the other viral transcription regions (reviewed by Russell, 2000). The E1B region encodes two major proteins, 19K and 55K, that prevent, via different routes, the induction of apoptosis resulting from the activity of the E1A proteins (Rao et al., 1992; Yew and Berk, 1992; reviewed in Shenk, 1996). In addition, the E1B-55K protein is required in the late phase for selective viral mRNA transport and inhibition of host protein expression (Pilder et al., 1986). Early region-2 (E2) is also divided in an E2A and E2B region that together encode three proteins, DNA binding protein, viral polymerase and pre-terminal protein, all involved in replication of the viral genome (reviewed by van der Vliet, 1995). The E3 region is not necessary for replication in vitro but encodes several proteins that subvert the host defense mechanism towards viral infection (reviewed by Horwitz, 2001). The E4 region encodes at least six proteins involved in several distinct functions related to viral mRNA splicing and transport, host-cell mRNA transport, viral and cellular transcription and transformation (reviewed by Leppard, 1997).

The late proteins necessary for formation of the viral capsids and packaging of viral genomes, are all generated from the major late transcription unit (MLTU) that becomes fully active after the onset of replication. A complex process of differential splicing and polyadenylation gives rise to more than 15 mRNA species that share a tripartite leader sequence. The early proteins E1B-55K and E4-Orf3 and Orf6 play a pivotal role in the regulation of late viral mRNA processing and transport from the nucleus (reviewed in Leppard, 1998).

Packaging of newly formed viral genomes in pre-formed capsids is mediated by at least two adenoviral proteins, the late protein 52/55K and an intermediate protein IVa2, through interaction with the packaging sequence located at the left end of the genome (Grable and Hearing, 1990; Gustin and Imperiale, 1998; Zang et al., 2001). A second intermediate protein, pIX, is part of the capsid and is known to stabilize the hexon-hexon interactions (Furcinitti et al., 1989). In addition, pIX has been described to transactivate TATA-containing promoters like the E1A promoter and MLP (Lutz et al., 1997).

Due to the extensive knowledge of the viral biology and the high efficiency of nuclear delivery after entry into cells, adenoviruses have become popular tools for gene delivery into human cells. In addition, adenoviral vectors are stable and can be produced relatively easy at a large scale. In most cases, vectors are deleted for at least the E1 region, which renders them replication deficient. Production of E1-deleted vectors based on subgroup C serotypes Ad5 or Ad2 is achieved in E1-complementing cell lines such as 293 (Graham et al., 1970), 911 (Fallaux et al., 1996) and PER.C6™ (Fallaux et al., 1998). As disclosed in U.S. Pat. No. 5,994,128, vectors and cell lines need to be carefully matched to avoid generation of replication-competent adenoviruses through homologous recombination between adenovirus sequences in the cell line and the vector. Thus, PER.C6™ cells and matched adenoviral vectors provide a preferred system for the production of group C adenoviral vectors (Fallaux et al., 1998). The deletion of E1 sequences provides space for the introduction of foreign genes in the viral vector. Since the maximum size of Ad5 genomes that can be incorporated into virions is limited to about 105% of the wild-type length, E1-deleted viruses can accommodate approximately 4.8 kb of foreign DNA (Bett et al., 1993).

The maximum packaging capacity in virions that lack pIX is reduced to approximately 95% of the normal genome length (Ghosh-Choudhury et al., 1987). This is most likely caused by the reduced stability of pIX— ("pIX-minus") virions. The deficiency in pIX-minus mutant Ad5 can be complemented by episomal expression of pIX in a packaging cell line used for producing viruses (Caravokyri et al., 1995).

Although the serotypes Ad5 and Ad2 are most commonly used as gene transfer vectors, other serotypes may have preferred characteristics that make them more useful as a therapeutic or prophylactic tool. Subgroup B viruses Ad35 and Ad11, for example, are much less prone to neutralization by human sera than Ad5 and Ad2 viruses (disclosed in WO 00/70071). Neutralization of adenoviral transfer vectors diminishes transduction efficiency in vivo. Furthermore, the infection efficiency of antigen presenting cells, like dendritic cells, by recombinant viruses carrying the fiber of Ad35 was found to be greatly enhanced in vitro compared to Ad5 viruses (WO 00/70071, WO 02/24730). Thus, Ad35-based vectors combine highly improved infection efficiency with low neutralization in human sera, making such vectors suitable for vaccination purposes.

Generation and propagation of fully E1-deleted Ad35-based vectors is possible using the technology discussed below. However, careful analysis of a variety of recombinant Ad35-based vectors has revealed that such vectors are less stable, i.e., can contain less foreign DNA compared to the Ad5-based vectors. In the current patent application, means and methods are presented to overcome this problem.

In addition, there is a need to further develop the presently available technology for adenoviruses that have broader serotype utility. Existing packaging cell lines typically comprise E1-encoded proteins derived from adenovirus serotype 5. Examples of such "standard" packaging cell lines are 293, 911 and PER.C6™. Attempts to produce vectors derived from other serotypes on these standard packaging cell lines have proven arduous, if not unsuccessful. Occasionally, some production is seen, depending on the particular serotype used. However, the yields of recombinant adenovirus vectors derived from adenovirus subgroups other than subgroup C, produced on cell lines transformed and immortalized by E1 from Ad5, is poor. In a paper by Abrahamsen et al. (1997), improved plaque purification of an E1A-deleted adenovirus serotype 7 vector (subgroup B) was observed on 293 cells comprising E4-orf6 derived from adenovirus serotype 5, as compared to 293 cells lacking the E4-orf6 sequence from Ad5. However, a problem was encountered with the stability of the vector as unexpected recombinations were observed in plaque-purified stocks. An additional problem was encountered with wild-type adenovirus contamination during production. Moreover, for large-scale production of adenoviruses, it is not useful to co-transfect E4-orf6 to obtain titers that are high enough for application. One option for growing such adenoviruses is to provide cells with the E4-orf6 gene stably integrated into the genome of the complementing/packaging cell line. Such cells have been described in the art (e.g. WO 96/22378). A disadvantage of that system is the fact that new stable cell lines have to be generated and numerous selection rounds have to be performed before stable and proper cells have been generated. This process is laborious and time-consuming. In general, it can be stated that generation and propagation of adenoviruses from serotypes other than serotype 5 (subgroup C), such as subgroup B viruses, have proven to be difficult on Ad5-complementing cells. As has been disclosed by the applicants in WO 00/70071, recombinant viruses based on subgroup B virus Ad35 can be made by co-transfection of an expression construct containing the Ad35-early region-1 sequences (Ad35-E1). Furthermore, Ad35-based viruses that are deleted only for E1A sequences and not for E1B were shown to replicate efficiently on PER.C6™ cells, suggesting that the E1A proteins of Ad5 are able to complement the Ad35-E1A functions (applicant's application WO 02/40665). Moreover, the experiments show that lack of Ad35-E1B results in poor yields on Ad5-complementing cells. WO 00/70071 also discloses cell lines for the production of E1-deleted non-group C adenoviral vectors by further modifying cell lines that are capable of complementing adenovirus serotype 5. WO 00/70071 further suggests that one should establish new cell lines harboring Ad35-E1 sequences for the complementation of recombinant adenovirus serotype 35 vectors lacking the E1 region (see also WO 02/40665). However, as also discussed above, if one desires to apply a specific serotype for a specific need, one would have to establish a new cell line for every specific serotype or one would have to modify the available cell lines that can complement adenovirus serotype 5 for complementation of the serotype of interest. It would clearly be advantageous to use the established cell lines that are available in the art and not to modify these and use them for the production of all other, non-Ad5 serotypes, applying the established and efficient methods known in the art.

It is concluded that there still exists a need for a production system to produce useful yields of adenovirus serotypes that are different from the serotypes of subgroup C.

Furthermore, there is still a need for suitable packaging systems comprising convenient packaging cells and recombinant subgroup B adenoviruses that are stable and can be propagated on such packaging cells.

BRIEF DESCRIPTION OF THE FIGURES

FIG. 3A. Sequence alignments of the proximal pIX upstream sequence regions of various adenoviruses generated with MEGalign software (DNAstar) using Clustal method (SEQ ID NOs:45-54, respectively). Source of sequences are indicated in the text. The Sp1 site and TATA-box in Ad5 and Ad2 (as in Babiss and Vales, 1991) are boxed.

FIG. 10. Sequence alignment of the region between the polyA signals of the E1A region and of the E1B/pIX region in three different subgroup B serotypes (SEQ ID NOs:55-57).

FIG. 21. Alignment between E4-orf6 of Ad5 (upper sequence) (SEQ ID NO:61) with E4-orf6 from Ad5 cloned into the Ad35 backbone (middle sequence) (SEQ ID NO:61) and the Ad35-E4-orf6 sequence (lower sequence) (SEQ ID NO:62), showing that the entire fragment has been replaced.

FIG. 22. Alignment between E4-orf6/7 of Ad5 (upper sequence) (SEQ ID NO:63) with the part of Ad5-E4-orf6/7 cloned into the Ad35 backbone (middle sequence) (SEQ ID NO:63) and the Ad35-E4-orf6/7 sequence (lower sequence)

(SEQ ID NO:64), showing that the orf6/7 sequence is partly chimeric, with the fusion approximately at the lysine (K) residue at position 138.

Figure 23:
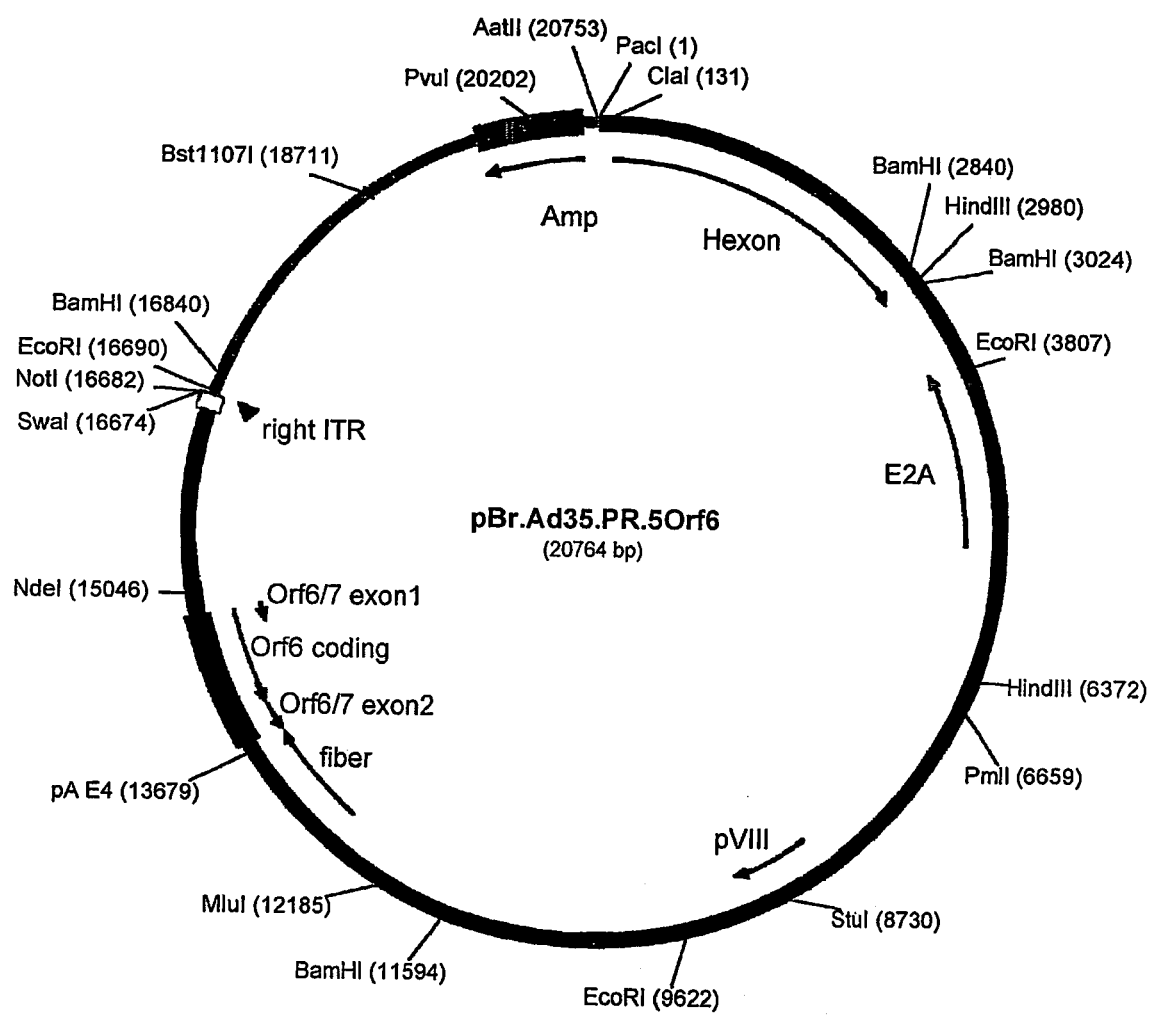

FIG. 23. Schematic representation of pBr.Ad35.PR.5Orf6 (ECACC deposit no. P02041227).

Figure 24:
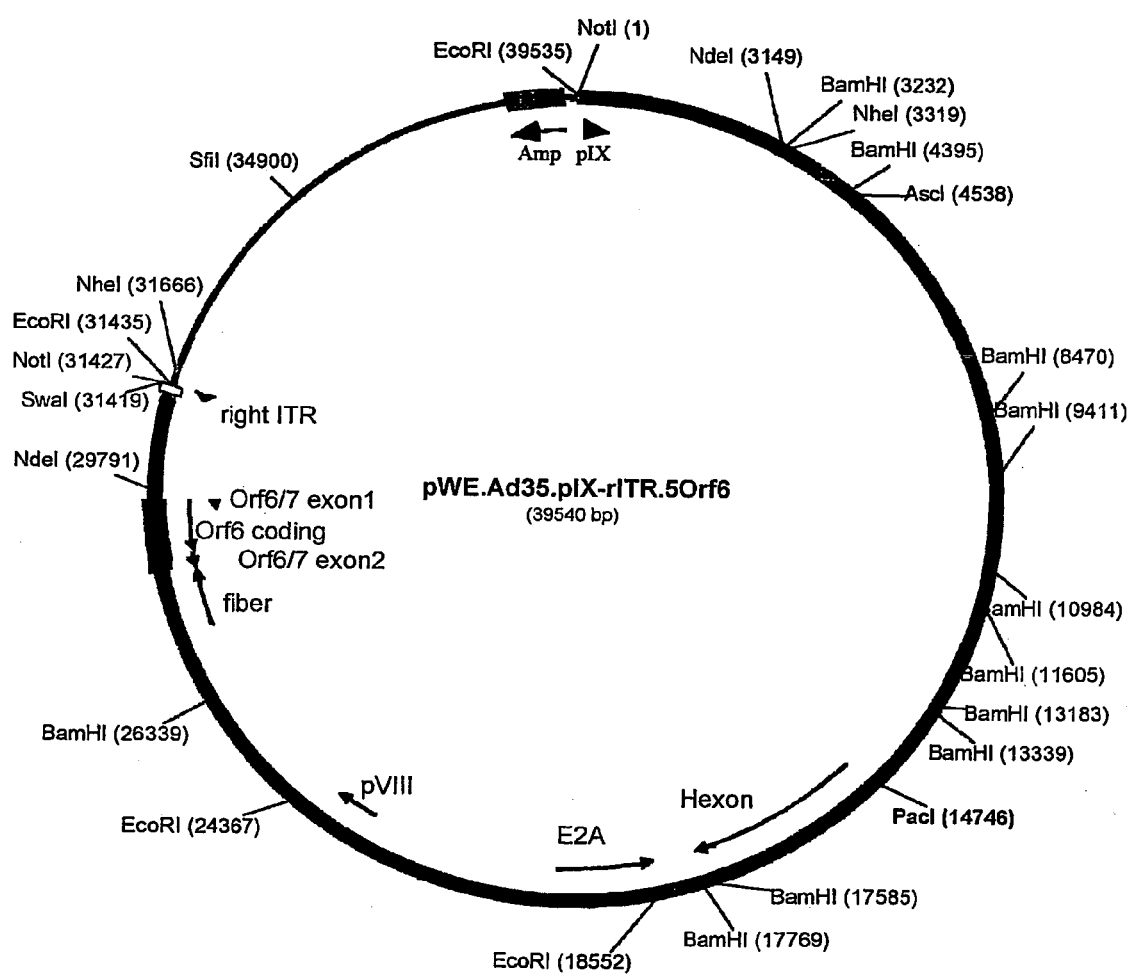

FIG. 24. Schematic representation of pWE.Ad35.pIX-rITR.5Orf6.

Figure 25:
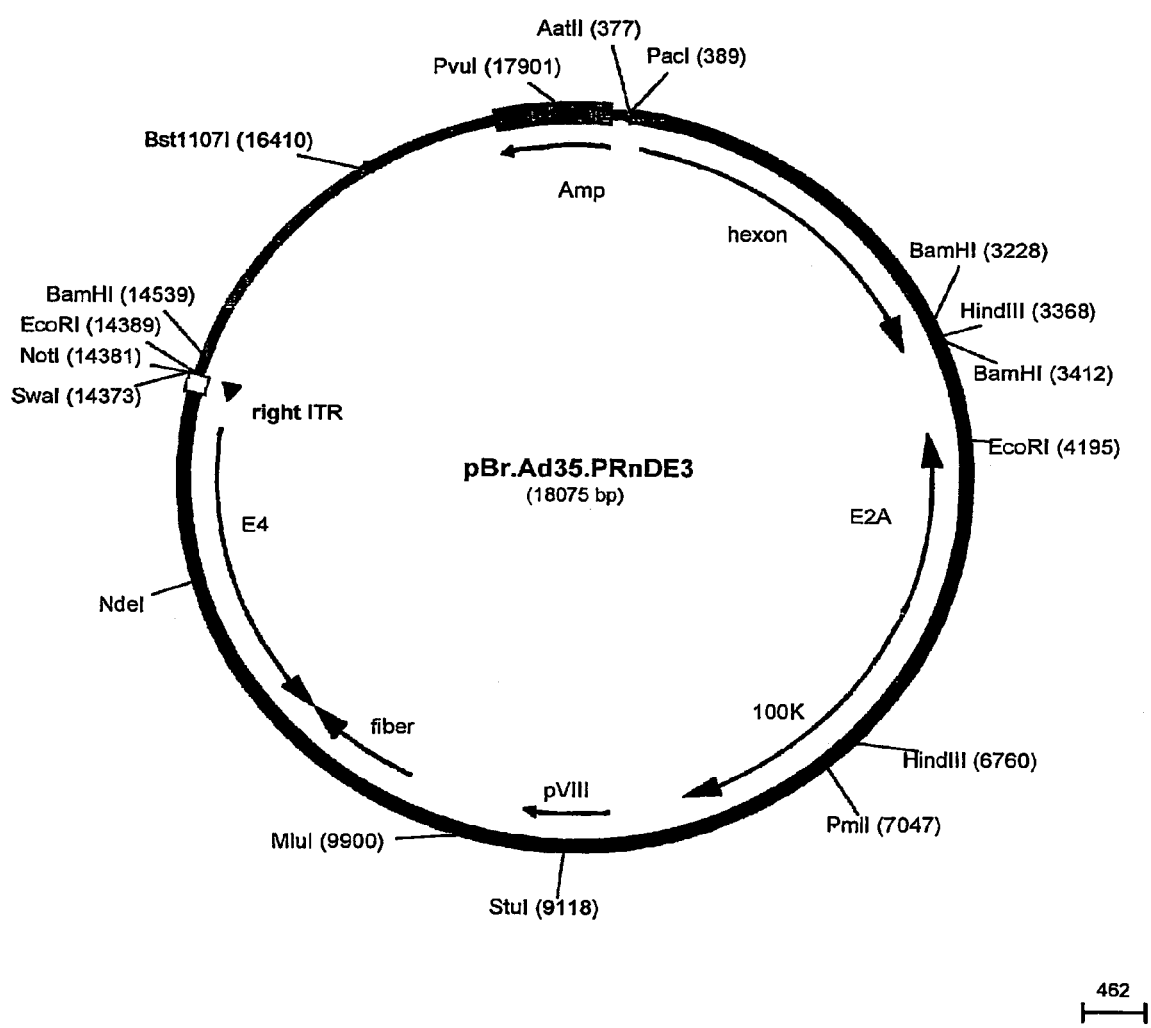

FIG. 25. Schematic representation of pBr.Ad35.PRnΔE3.

Figure 26:
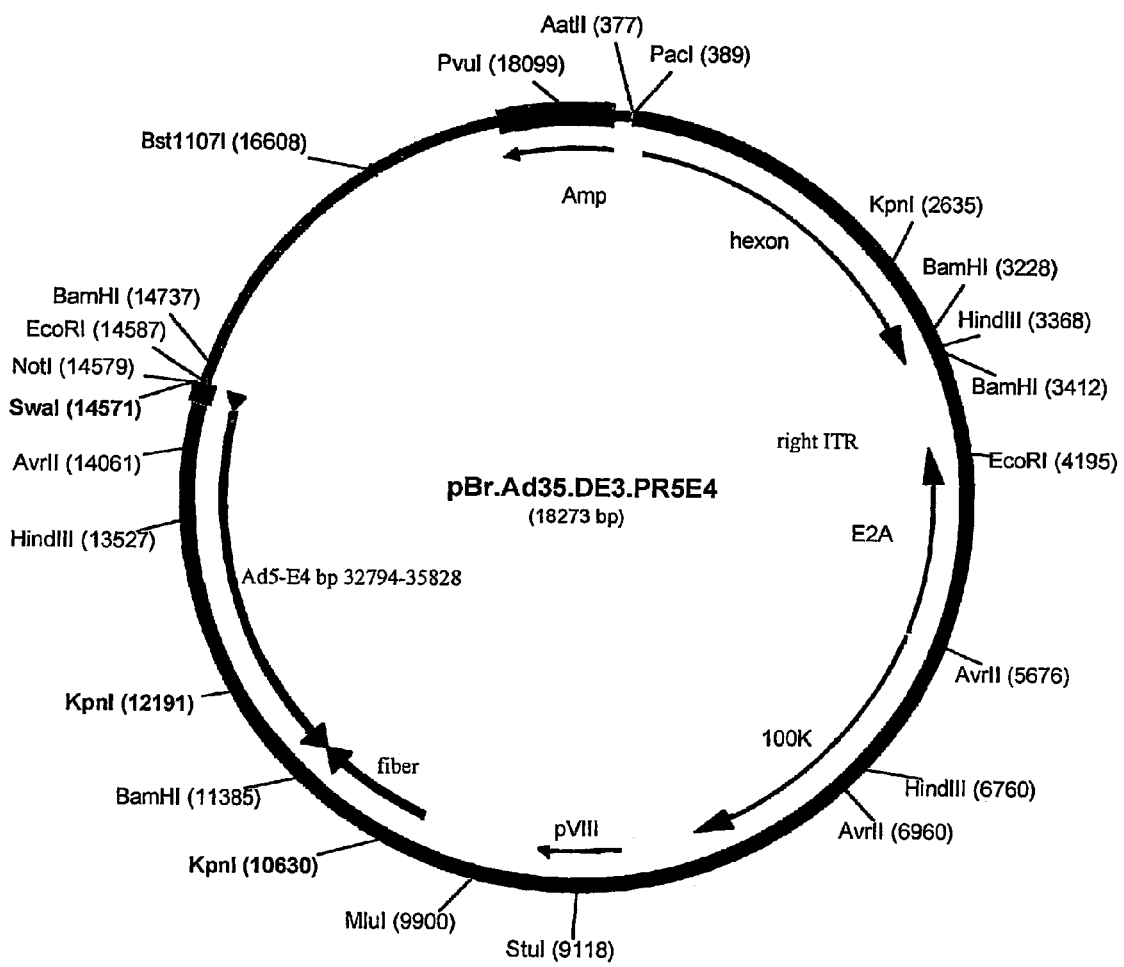

FIG. 26. Schematic representation of pBr.Ad35.ΔE3.PR5E4.

Figure 27:
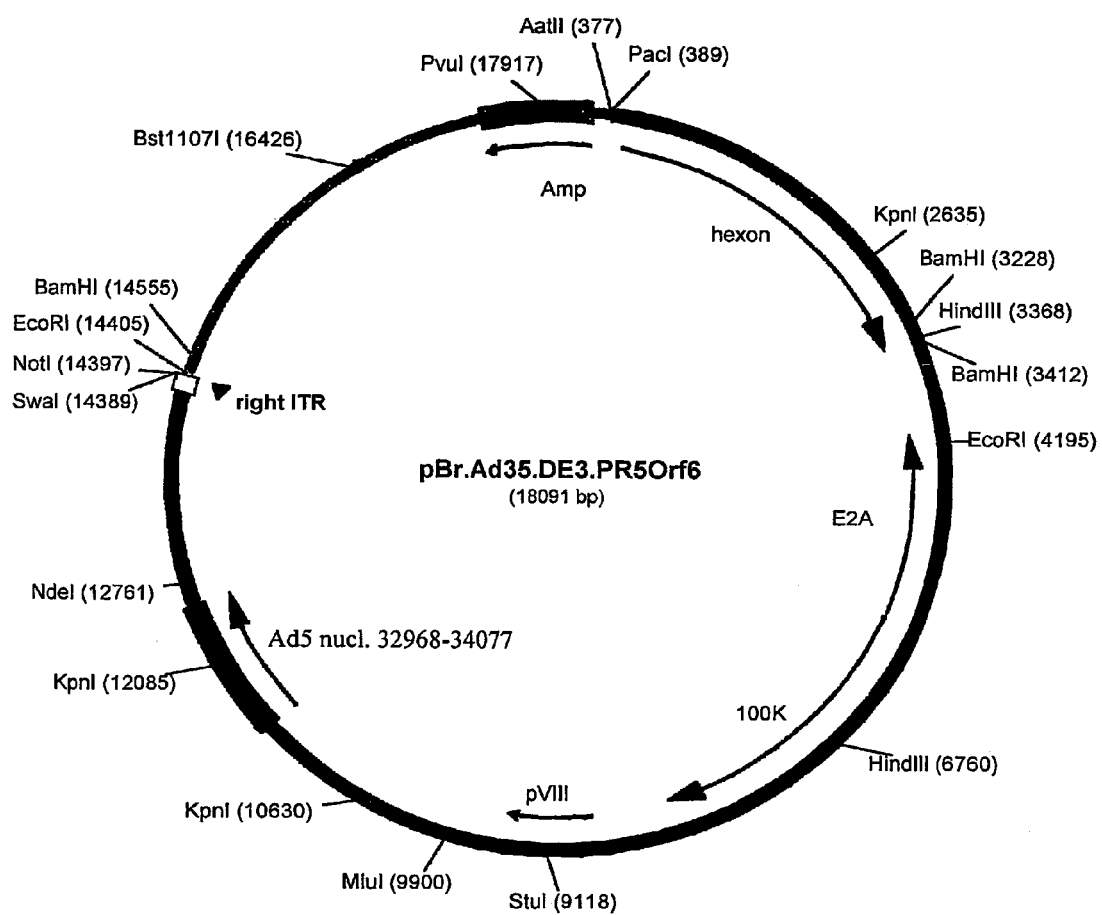

FIG. 27. Schematic representation of pBr.Ad35.ΔE3.PR5Orf6.

FIG. 28. Schematic representation of the system for producing recombinant adenoviral particles in cells, such as PER.C6™, through a double-homologous recombination event.

Figure 29:
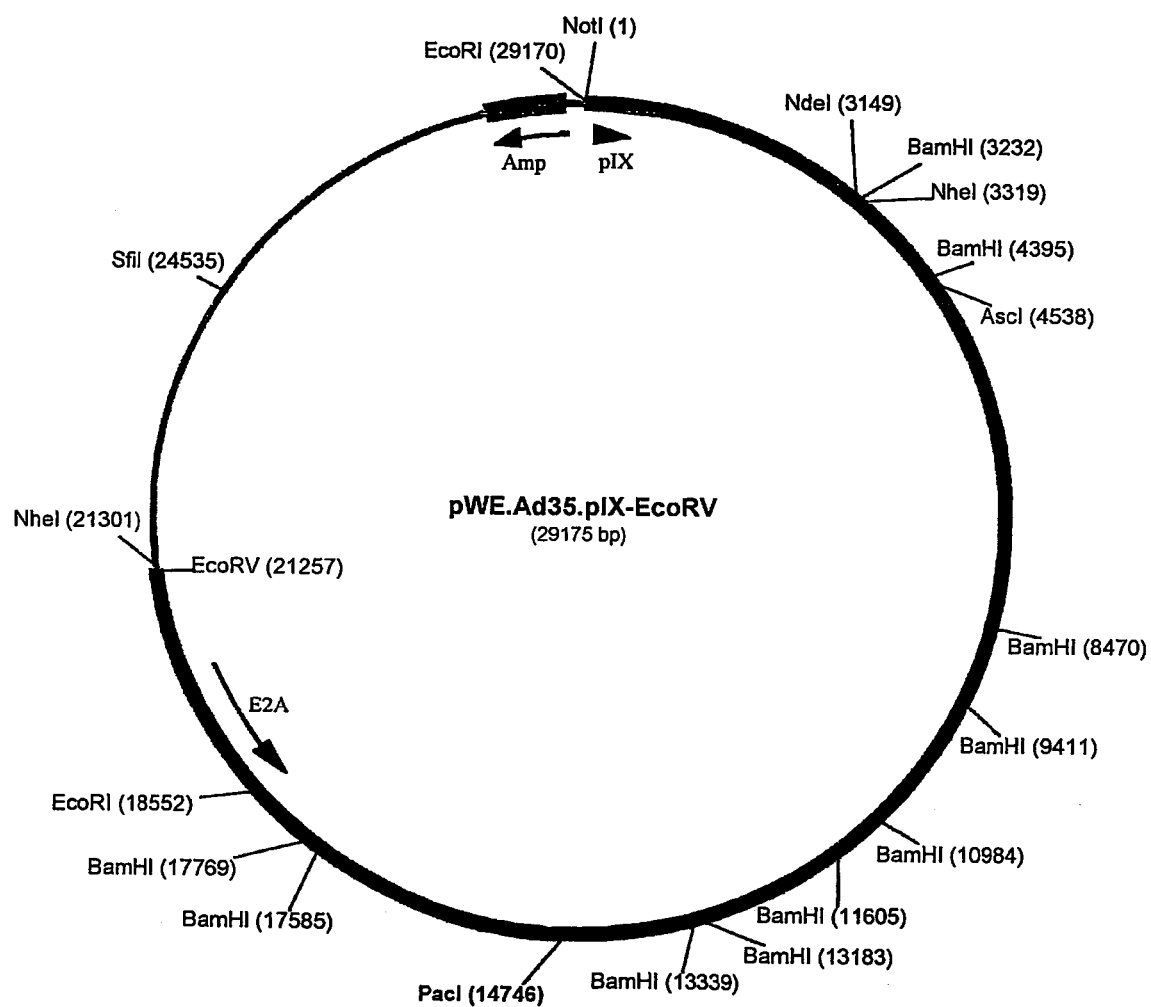

FIG. 29. Schematic representation of pWE.Ad35.pIX-EcoRV.

Figure 30:
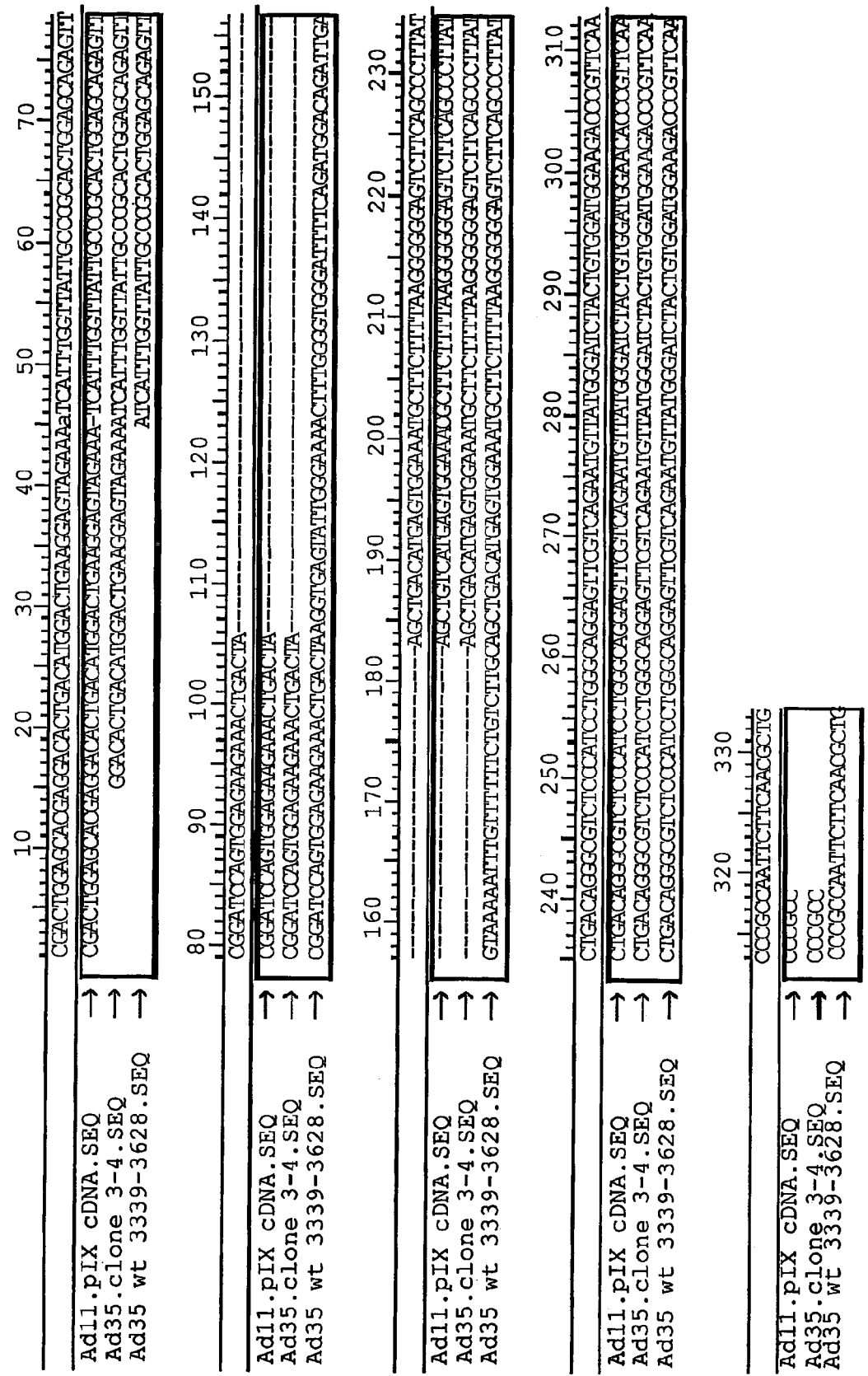

FIG. 30. Alignment of Ad35 and Ad11 pIX-cDNA sequences with wild-type Ad35 sequence (SEQ ID NO:58-60). The sequences obtained from cloned cDNA fragments as described in Example 18 were aligned using SeqMan software from DNAstar. Ad35 cDNA sequences were derived from RNAs isolated from wild-type Ad35- or Ad35E1B+Luc-infected cultures (sequence of one out of seven clones is shown), the Ad11 cDNA sequence from RNA isolated from a wild-type AD11-infected culture. The sequence numbering is arbitrary. For the Ad35 wild-type sequence, nucleotide 3339 to nucleotide 3628 of the wild-type Ad35 sequence is shown. The intron sequence (seen as a gap in the cDNA sequences) is flanked by splice donor (SD) and splice acceptor (SA) sites closely matching the known consensus sequences. The SeqMan software has placed the first two nucleotides from the SD (AG) in the cDNA sequences at the 3' end of the intron sequence instead of the 5' end.

Figure 31:
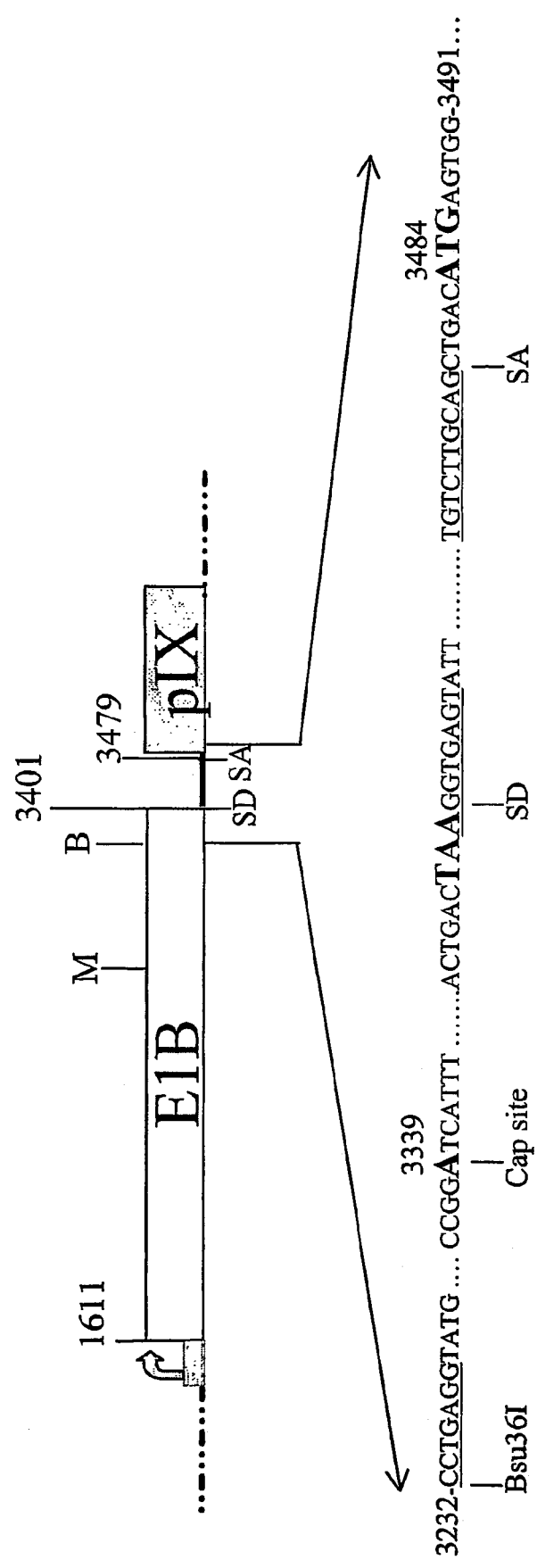

FIG. 31. Location of the pIX cap site in Ad35 viruses (nts 565-1992 of SEQ ID NO:55). Schematic representation of the genome organization around the E1B gene and pIX sequences in Ad35 depicts the transcription start site and intron boundaries in the pIX mRNA. Nucleotide sequences are according to wild-type Ad35 DNA (WO 00/70071). M=MunI, B=Bsu36I, SD=splice donor and SA=splice acceptor. The transcription start site (nucleotide 3339, cap site), the stop codon of 55K (TAA) and the start codon of pIX (nucleotide 3484, ATG) are in bold. A dotted line indicates that sequences are not shown.

Figure 32:
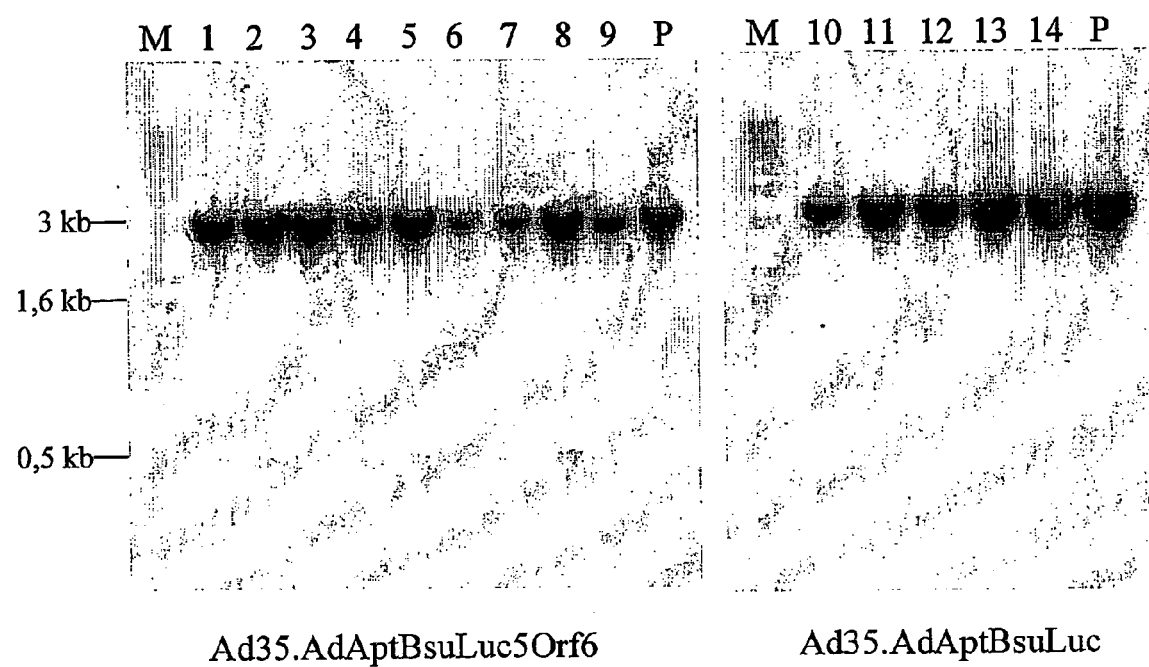

FIG. 32. Transgene PCR results from Ad35 viruses with a 166 bp 3' E1B sequence retained. A representative example of the results of the transgene PCR assays on Ad35.AdAptBsuLuc5Orf6 (lanes 1-9) and Ad35.AdAptBsuLuc viruses (lanes 10-14). M=1 kb+marker (Invitrogen), P=pAdAptBsuLuc control plasmid.

SUMMARY OF THE INVENTION

It is shown in the present invention that a recombinant group B adenovirus that has a deletion in the E1 region up to the stop codon of E1B-55K, can accommodate less exogenous sequences than a similar Ad5-recombinant adenovirus. It appears that this is due to a relative underexpression of the pIX gene in the group B virus in a given packaging cell, when the pIX-coding region is preceded by sequences between the E1B-55K stop codon and the pIX start codon only. It is shown that such viruses can be rendered more stable and/or capable of accommodating more exogenous sequences when either the pIX promoter is at least partly restored by including sequences from the E1B-55K-coding region into such a virus or by using a heterologous promoter to regulate pIX, such that a normal, or even a relative overexpression, of pIX is achieved in a given packaging cell.

The present invention provides a recombinant adenovirus having at least a deletion in the E1 region, characterized in that at least part of the sequences encoding the E1B-55K gene product that increase the expression of the pIX gene are present in the adenovirus, with the proviso that the recombinant adenovirus does not express a functional E1B-55K gene product. Such adenoviruses are more stable and/or can harbor more exogenous DNA than the corresponding adenovirus that lacks all E1B-coding sequences. Preferably, the adenovirus comprises about 700 base pairs or less of the sequences that are directly upstream of the pIX-coding sequence. In preferred embodiments, the adenovirus is a group B adenovirus, more preferably, an adenovirus derived from or based upon Ad35 or Ad11. The invention further provides a method for increasing the stability and/or the packaging capacity of a recombinant adenovirus having at least a deletion in the E1-region, the method comprising retaining or reintroducing at least part of the sequences that encode the E1B-55K gene product and increasing the expression of the pIX gene in the adenovirus.

Instead of, or in addition to, the presence of E1B-55K sequences increasing the expression of the pIX gene, it is also possible to change the sequences preceding the pIX-coding sequence into a stronger promoter to increase the expression of pIX, resulting in an increase of the stability of a recombinant adenovirus and/or an increase of the packaging capacity of the adenoviral particle produced by the method of the invention. Hence, the present invention further provides methods and means for increasing the stability and/or the packaging capacity of a recombinant adenoviral vector lacking at least the E1-region and comprising exogenous genetic information, comprising the step of expressing the elements necessary for production and assembly of the recombinant adenoviral vector into virus particles in a packaging cell in the presence of an elevated level of pIX gene product in the packaging cell, wherein the elevated level of pIX gene product is brought about by the overexpression of genetic information encoding the pIX protein, by the use of a modified pIX gene in the vector, the modification causing the pIX gene product to be overexpressed. In a preferred embodiment, the modified pIX gene comprises a heterologous promoter driving the expression of the genetic information encoding pIX, the heterologous promoter being a promoter causing the genetic information encoding pIX to be overexpressed in the packaging cell. In one embodiment, the heterologous promoter is, at least in part, derived from or based upon the pIX promoter of an adenovirus serotype that confers higher levels of pIX expression than the endogenous proximal pIX upstream sequence of the recombinant adenoviral vector. In one embodiment, the heterologous promoter is, at least in part, derived from or based upon the pIX promoter of Ad5. In one aspect, the invention provides a recombinant adenoviral vector lacking at least the E1-region and comprising a gene of interest, wherein the pIX gene is modified, and wherein the recombinant adenoviral vector is not derived from an adenovirus serotype 5. It is yet another aspect of the present invention to provide a recombinant nucleic acid sequence comprising a modified adenoviral pIX gene, wherein the genetic information encoding the pIX protein is not derived from an adenovirus serotype 5 or an adenovirus serotype 7 pIX-encoding sequence. In a preferred embodiment, the modified pIX gene comprises a heterologous promoter driving the expression of the genetic information encoding pIX.

The present invention further provides recombinant adenovirus vectors comprising structural and non-structural elements of an adenovirus of a first serotype, wherein the vector further comprises a sequence encoding an E4-orf6 protein, wherein the sequence is selected from the group consisting of: a) an E4-orf6-encoding sequence derived from an adenovirus of a second serotype different from the first serotype; b) an E4-orf6-encoding sequence derived from an adenovirus of the first serotype by way of a deletion, mutation, addition and/or substitution in one or more codons; and c) an E4-orf6-encoding sequence comprising a fusion between a part of an E4-orf6-encoding sequence derived from a second serotype different from the first serotype and a part of an E4-orf6-encoding sequence derived from a third serotype, wherein the third serotype may be identical to or different from the first serotype.

The invention further provides methods for the production of such recombinant adenovirus vectors comprising structural and non-structural elements of an adenovirus of a first serotype, the method comprising the steps of: a) providing a complementing cell harboring an E1B-55K-encoding sequence, derived from an adenovirus of a second serotype in expressible form, with the necessary elements of an adenovirus so as to allow assembly of the recombinant adenovirus vector by the complementing cell, wherein the elements comprise at least some structural and non-structural elements from an adenovirus of the first serotype different from the second serotype and a sequence encoding a functional E4-orf6 protein or a functional part, derivative and/or analogue thereof, which is compatible with the expressible E1B-55K protein in the complementing cell; b) culturing the complementing cell in a medium under conditions allowing for production and assembly of the adenovirus vector to take place; and c) harvesting the recombinant adenovirus vector so produced from the medium and/or the complementing cell, wherein the sequence encoding the compatible E4-orf6 protein is present in the recombinant adenovirus vector so produced.

The invention further provides a recombinant adenovirus comprising a recombinant nucleic acid molecule derived from an adenovirus, the recombinant nucleic acid molecule having at least a deletion in the E1 region, characterized in that at least part of the sequence encoding the E1B-55K gene product is present in the recombinant nucleic acid molecule and/or that the pIX-coding sequence is under the control of a heterologous promoter, the recombinant adenovirus further comprising structural and non-structural elements of an adenovirus of a first serotype, wherein the recombinant adenovirus further comprises a sequence encoding a functional E4-orf6 protein or a functional part, derivative and/or analogue thereof, wherein the sequence is chosen from the group of: a) an E4-orf6-coding sequence derived from an adenovirus of a second serotype different from the first serotype; b) an E4-orf6-encoding sequence derived from an adenovirus of the first serotype comprising a deletion, mutation, addition and/or substitution in one or more codons; and c) an E4-orf6-encoding sequence comprising a fusion between a part of an E4-orf6-encoding sequence derived from a second serotype and a part of an E4-orf6-encoding sequence derived from a third serotype, wherein the third serotype may be identical to or different from the first serotype.

The invention also provides a packaging system comprising a recombinant adenovirus according to the invention and a packaging cell, wherein the packaging cell and the recombinant adenovirus together comprise all necessary elements to allow production and assembly of the recombinant adenovirus in the packaging cell, and wherein the packaging cell expresses nucleic acid encoding at least an adenoviral E1B-55K protein or a functional, part, derivative and/or analogue thereof, which is compatible with the E4-orf6 protein or a functional part, derivative and/or analogue thereof, of the recombinant adenovirus.

The invention also provides a method for producing a stable recombinant adenovirus comprising structural and non-structural elements of an adenovirus of a first serotype, wherein the recombinant adenovirus comprises a recombinant nucleic acid molecule derived from an adenovirus, which nucleic acid molecule has a deletion in the E1 region and comprises nucleic acid derived from at least part of the sequence encoding the E1B-55K gene product increasing expression of the pIX protein not leading to the expression of a functional E1B-55K protein from the nucleic acid molecule and/or has a pIX-coding sequence under control of a heterologous promoter, the method comprising the steps of: a) providing a complementing cell expressing an E1B-55K-encoding sequence or a functional part, derivative and/or analogue thereof, derived from an adenovirus of a second serotype in expressible form, with the necessary elements of an adenovirus as to allow assembly of the recombinant adenovirus vector by the complementing cell, wherein the elements comprise at least some structural and non-structural elements from an adenovirus of the first serotype different from the second serotype and a sequence encoding a functional E4-orf6 protein or a functional part, derivative and/or analogue thereof, which is compatible with the expressible E1B-55K protein in the complementing cell; and b) culturing the complementing cell in a medium under conditions allowing for production and assembly of the recombinant adenovirus to take place; and c) harvesting the recombinant adenovirus so produced from the medium and/or the complementing cell.

The invention further provides a method of producing stable adenoviral vectors containing exogenous genetic information without the generation of replication-competent adenovirus, wherein the vectors are of a serotype other than adenovirus 5, comprising the steps of growing cells under conditions conducive to adenoviral vector production, the cells, or an ancestor thereof, having been provided with and expressing nucleic acid coding for all elements essential for adenoviral vector production and packaging, the elements essential for generating replication-competent adenoviral vectors being present on at least two separate nucleic acid molecules not giving rise to intermolecular recombination, the essential elements comprising at least one serotype determining structural and one non-structural element from an adenovirus of a first serotype other than Ad5, and comprising an E1B-55K gene product from a second serotype different from the first serotype and an E4-orf6 gene product compatible with the E1B-55K gene product. In certain embodiments, the nucleic acid coding for all essential elements essential for adenoviral vector production and packaging comprise a recombinant pIX gene. In one embodiment, a recombinant pIX gene is a pIX-coding sequence under control of a heterologous promoter.

In another aspect, the present invention provides methods for treating or preventing diseases or disorders in human or animal subjects, comprising a step of administering recombinant adenoviral vectors according to the invention to a human or animal subject. In other aspects, the invention provides vaccines and pharmaceutical compositions comprising the adenoviral vectors according to the invention. In another aspect, the invention provides for the use of recombinant adenoviral vectors according to the invention for the preparation of a medicament for the prevention or treatment of diseases or disorders in human or animal subjects. The invention also relates to a kit of parts comprising cell lines and adenoviral vectors provided by the invention for executing the methods provided by the invention.

DETAILED DESCRIPTION OF THE INVENTION

It is one aspect of the invention to provide a method for increasing the stability and/or the packaging capacity of a recombinant adenovirus having at least a deletion in the E1-region, comprising the step of expressing the elements necessary for production and assembly of the recombinant adenovirus into virus particles in a packaging cell in the presence of an elevated level of pIX gene product in the packaging cell, relative to the level of pIX gene product obtained when the pIX-coding sequence is behind its endogenous proximal upstream sequence without E1B-55K sequences. In certain embodiments of the method of the invention, the elevated level of pIX gene product is brought about by retaining or reintroducing part of the E1B-55K sequences in the adenovirus. In other embodiments, the elevated level of pIX gene product is brought about by the expression of the pIX-coding sequences under control of a heterologous promoter.

The invention further provides a recombinant adenovirus comprising a functional pIX-coding sequence under control of an expression sequence, the expression sequence comprising part of an E1B-55K sequence capable of increasing expression of the pIX-coding sequence in a given packaging cell, relative to the expression of the pIX-coding sequence behind its endogenous proximal pIX upstream sequence without the part of the E1B-55K sequence, with the proviso that the part of an E1B-55K sequence does not code for a functional E1B-55K gene product. It is shown in the present invention that pIX-promoter sequences can be present in the E1B-55K sequences, and including these sequences in the expression sequence can, therefore, increase pIX expression. The presence of the E1B-55K sequences increases the stability and/or packaging capacity of the recombinant adenovirus, compared to the situation where the pIX-coding sequence is behind its endogenous proximal pIx upstream sequence without the part of the E1B-55K sequence.

An adenovirus of serotype 35 with a deletion in the E1 region but with an intact E1B-55K-coding region (pBr.Ad35.leftITR.ΔE1AΔ21K) has been disclosed in WO 02/40665. However, a functional 55K gene product, such as is present in the disclosed vector, inhibits apoptosis and, hence, it is desired to obtain recombinant adenovirus that lacks functional E1B-55K expression, e.g., by mutating the E1B-55K gene or, preferably, by including only part of the E1B-55K sequences; more preferably, including only sequences downstream of the E1B-55K start codon. It will be clear to the skilled person in the art that it is beneficial to minimize the amount of E1B-55K sequences in the vector in order to generate viruses with a maximal E1 deletion to accommodate more foreign nucleic acid, while at the same time retaining sufficient E1B-55K sequences to have the benefit according to the present invention of an increased stability and/or increased packaging capacity within the recombinant adenovirus. With the teachings of the present invention, the person skilled in the art will be able to find the minimally required sequences within E1B-55K that lead to the stabilization and/or increase in packaging capacity of the recombinant adenovirus, e.g., by using standard molecular cloning techniques to obtain serial deletions within the E1B-55K region starting from the disclosed vector (pBr.Ad35.leftITR.ΔE1AΔ21K) and determining the stability or packaging capacity. It is, therefore, an object of the present invention to provide a recombinant adenoviral vector according to the invention wherein the sequences encoding the E1B-55K gene product comprise about 0.7 kb or less of the adenovirus sequences that are directly upstream of the pIX open reading frame. In other embodiments, the sequences comprise not more than about 680, 600, 550, 500, 450, 400, 350, 300, 250, 200, 150, or 100 nucleotides of the adenovirus sequences that are directly upstream of the pIX open reading frame. In one embodiment, such a recombinant adenoviral vector retains 166 bp of the 3' end of the 55K-coding sequence. As will be clear to the person skilled in the art, the invention is not limited to the presence of a sequence that is found in a contiguous stretch directly upstream of the pIX-coding sequences in the natural adenovirus. Instead, it will also be possible according to the invention to have sequences that are more upstream, i.e., from the E1B-55K region (e.g., a restriction or PCR fragment; see, e.g., Example 10 and FIG. 9), fused to the more proximal pIx regulatory sequences, thereby creating an artificial combination of regulatory sequences, as long as this results in increased pIX expression in a given packaging cell, when compared to the absence of any E1B-55K sequences. In a preferred embodiment, the adenovirus is a subgroup B adenovirus, more preferably, an Ad35 or Ad11 adenovirus. Adenoviruses of serotypes 35 or 11 have been shown to be particularly useful for administration to humans, since there are much less individuals that have neutralizing antibodies to these serotypes than to the serotype 5 hitherto most used (WO 00/70071). It is another aspect of the invention to provide the nucleic acid that can act as the genome of the adenovirus according to the present invention.

As an alternative or in addition to the presence of E1B-55K sequences that increase the expression of the pIX gene, it is also possible to overexpress pIX itself by mutating the pIX gene, preferably its promoter, to increase the stability and/or packaging capacity of a recombinant adenovirus. A modified pIX gene is a pIX gene having a different promoter, transcription terminator, and/or mutated coding sequences, e.g., obtained by codon optimization, introduction of introns that stabilize RNA, and the like. A pIX gene, according to the invention, comprises genetic information encoding pIX and includes nucleic acid, such as the pIX gene found in natural adenoviruses, cDNA and information encoding mutant pIX in the form of allelic variants or nucleic acid encoding mutant pIX that has at least part of the function of pIx, which may differ from normal pIX in quantitative or qualitative aspects, derived from or based on pIX by mutation, deletion, addition, or translocation of amino acids, or combinations thereof.

If a recombinant adenovirus has a deletion of at least the E1B-55K region, up to and including the stop codon of the E1B-55K gene product, the pIX open reading frame will be preceded by sequences between the E1B-55K stop codon and the start codon of pIX. These sequences are herein referred to as the "endogenous proximal pIX upstream sequences" (e.g., the Ad35-pIX upstream sequence in Ad35-based recombinant adenoviral vectors, the Ad11-pIX upstream sequence in Ad11-based recombinant adenoviral vectors, etc., are referred to as endogenous in this respect; the definition includes allelic variants that may be found in nature and which are not created in the laboratory; see FIG. 3A for some proximal pIX upstream sequences).

A "heterologous promoter," as used herein, is defined as any sequence different from the sequences naturally found upstream of the pIX gene, including the sequences of the E1B-55K region and the endogenous proximal pIX upstream sequences, and being capable of acting as a promoter and thereby regulating transcription of pIX-coding sequences. In one aspect, a heterologous promoter may be a sequence, at least in part, derived from or based upon a proximal pIX upstream sequence (i.e., the sequences between the E1B-55K stop codon and the start codon of pIX) from an adenovirus from another serotype other than the serotype from which the recombinant adenoviral vector is derived (e.g., an Ad5-pIX upstream sequence in an Ad35-recombinant adenoviral vector). This is referred to herein as a "non-endogenous proximal pIX promoter."

In one embodiment of the invention, Ad35-derived pIX expression is driven by an Ad5 non-endogenous proximal pIX promoter. Any non-endogenous proximal pIX promoter derived from or based upon the proximal pIX upstream sequence from a serotype that confers higher levels of pIX expression than the endogenous pIX proximal sequences of the adenoviral vector may be used. Identification of such non-endogenous proximal pIX promoters may be based upon sequence information, such as will be evident to the person skilled in the art from Example 4. In particular embodiments, the adenoviral vector, according to the invention, is derived from or based upon an adenovirus subgroup E serotype or, preferably, of subgroup B serotype. In specific embodiments, the adenoviral vector is derived from or based upon an adenovirus serotype 35 (Ad35), Ad11, Ad7, or Ad4. In alternative embodiments, the non-endogenous proximal pIX promoter is, at least in part, derived from or based upon a proximal pIX upstream sequence of an adenovirus classified in subgroups C, A, D, or F. In particular embodiments, the non-endogenous proximal pIX promoter is, at least in part, derived from or based upon a proximal pIX upstream sequence of an adenovirus serotype 12 (Ad12), Ad9, or Ad40, or, more preferably, of Ad5 or Ad2. Alternatively, sequences acting as non-endogenous proximal pIX promoters can be found empirically, by general molecular biology methods known to persons skilled in the art, such as by transcription assays wherein promoters can be routinely tested for strength. It will be clear to the skilled person that elements from a promoter may be swapped without exchanging the whole promoter, e.g., adding, deleting, or mutating known transcription factor-binding sequences to a promoter may influence its strength. Mutating at least part of promoter sequences can be done by changing the sequence by mutations, such as by additions, deletions, or exchanging of one or more nucleotides, including stretches of nucleotides with a known function. Substituting promoter sequences is done by replacing part or all of these sequences by a different promoter. Such replacing can be done according to standard molecular biology techniques all well known to the person skilled in the art. Any promoter can be constructed in operable association with the pIX gene of choice and tested for its effect.

In another aspect, a heterologous promoter is unrelated to adenoviral non-endogenous proximal pIX promoters. Therefore, heterologous promoters may also be viral promoters, including but not limited to, promoters based upon or derived from Cytomegalovirus (CMV, e.g., the human CMV-immediate early gene promoter, further herein referred to as the CMV promoter), Rous Sarcoma Virus (RSV, e.g., the RSV long terminal repeat promoter, further referred to herein as the RSV promoter), TK, HBV, SV40 and the like. In one embodiment, an adenoviral E1B promoter is used as a heterologous promoter. Cellular promoters can also be used as heterologous promoters, and these include, but are not limited to, promoters from PGK, metallothionein, EF1-α, β-actin, and the like. Synthetic or hybrid promoters comprising elements from more than one promoter, can also be used for the invention and are all included within the scope of the term "heterologous promoter." Promoters used may be constitutive or inducible. In the context of an inducible promoter, a promoter is considered suitable for the invention if it gives overexpression in its induced state. Any promoter sequence resulting in overexpression of pIX, according to the invention, can be used as a heterologous promoter. Besides promoter strength, one other aspect determining the usefulness of a particular promoter when present in the recombinant adenoviral vector itself, is its size, as longer promoters will take up space available for the transgene. A person skilled in the art will be able to use the present invention to allow for optimizing the vector experimentally with respect to promoter length and strength with regard to insert size, to find the most stable recombinant vector.

It will be clear to one skilled in the art that a heterologous promoter may still contain or include part or all of the endogenous proximal pIX upstream sequences or, alternatively, wholly replace these sequences, as long as the heterologous promoter according to the invention can cause the overexpression of genetic information encoding pIX in a packaging cell of choice. It will also be clear to the person skilled in the art that when an endogenous non-pIX adenoviral promoter (e.g., the E1A, E2A, etc., promoter) or a heterologous promoter that, for instance, regulates the transgene, is used for driving expression of pIX by use of an internal ribosome entry site (IRES) between the non-pIX adenovirus gene or the transgene and the pIX-coding sequence (in either order), this is to be regarded as being within the scope of the term "heterologous promoter" according to the invention.

An elevated or increased level of pIX gene product in the invention is the result of overexpression of the pIX gene in a packaging cell of choice. "Overexpression of the pIX gene," as used herein, is defined as an expression level of pIX, either an RNA or protein level, or both, that is higher than the pIX-expression level obtained when the coding region of pIX is behind the "endogenous proximal pIX upstream sequences," as defined herein, in a given packaging cell. "Overexpression" is meaningful in the context of the present invention for a particular heterologous promoter-pIX combination of an adenovirus in combination with a particular packaging cell of choice. Methods to determine expression levels are generally well known to persons skilled in the art and include, but are not limited to, RT-PCR, Northern blotting, Western blotting, and the like. For the present invention, overexpression would be measured by determining the expression levels in a recombinant adenovirus with a given insert (e.g. luciferase) in a given packaging cell of choice, wherein the genetic information encoding pIX is behind the endogenous proximal pIX upstream sequences without E1B-55K sequences, and comparing these expression levels to those in a recombinant adenovirus that is the same except that the pIX-coding region is regulated by a heterologous promoter or by sequences from the endogenous E1B-55K gene (its "natural" promoter that has been at least partly reconstituted). Overexpression of pIX is indicated by a ratio higher than one for the expression level obtained by the heterologous or "natural" promoter over that obtained by the endogenous proximal pIx upstream sequences without E1B-55K sequences. The choice of a packaging cell is determined by factors such as the serotype of the elements of the recombinant adenovirus that interact with the complementing adenoviral functions in the packaging cell, product purity (such as absence of replication-competent adenovirus from the generated batch), ease of use, growth characteristics, and the like. Examples of packaging cells are known to the person skilled in the art, and include 293 cells, 911 cells, and PER.C6™ cells as used herein, as well as derivatives thereof, adapted for complementation of adenoviral vectors of specific serotypes, such as PER55K.

It will be clear that in all embodiments of the invention, the pIX-coding sequences and regulatory sequences driving the expression of pIX can be positioned on their natural location within the adenovirus genome, as well as in different parts of the adenovirus genome, e.g., in the region that originally contained the E3 sequences.

Recombinant adenoviruses with increased stability are capable of incorporating larger genomes into virus particles (virions). Hence, increasing the stability of recombinant adenoviruses as used herein will allow the recombinant adenoviruses, according to the invention, to include more foreign genetic information comprising a gene of interest. Furthermore, recombinant adenoviruses with increased stability, according to the invention, may be capable of being propagated for more passages without signs of instability. Stability can be measured by several methods known to people skilled in the art, including, but not limited to, PCR on recombinant virus to demonstrate the presence of desired recombinant adenoviral vectors. Instability will lead to by-products, which can also be visualized by PCR methods and the like. Restriction analysis of viral DNA, determination of the relative infectivity of virus particles, and determination of the thermostability of adenoviral particles also can be used to determine the stability of recombinant adenoviral vectors (Caravokyri and Leppard, 1995). Methods to determine stability/instability of recombinant adenoviral vectors are also given in Example 3 of this application. A "recombinant adenovirus," also called "recombinant adenoviral vector" or "adenoviral vector," as used herein, is derived from or based upon an adenovirus, lacks at least part of the E1 region (comprising the E1A and E1B genes) of an adenovirus and can comprise foreign genetic information of which delivery and/or expression by the vector is desired. "Exogenous (or foreign) genetic information," as used herein, is any genetic information that is not naturally present in an adenovirus and is also referred to as a "transgene." This includes, but is not limited to, genes of interest, expression cassettes, and the like. Such exogenous genetic information can fill the space in the genome that has become available by the deletion of adenoviral E1 sequences. Recombinant adenoviral vectors are useful for various purposes, such as in gene therapy applications, vaccine preparation, and the like. In addition to the E1 region deletion, E3 sequences can also be deleted from such adenoviral vectors to increase the capacity for foreign genetic information in certain preferred embodiments. Other deletions and various combinations of part or complete deletions of E2, E3, and E4 regions, combined with the E1 deletion, can be used, if necessary, in combination with a packaging cell comprising the genetic information lacking in the adenoviral vector when necessary for replication of the adenoviral vector. All recombinant adenoviruses having a deletion in the E1-region optionally combined with any other deletions in the adenovirus genome, are meant to be included within the scope of the present invention. The adenoviruses of the present invention can be used in different settings, such as gene therapy or prophylactic and/or therapeutic vaccination, including tumor vaccination and anti-viral vaccination. For this, the adenoviral vector functions as a gene delivery vehicle, wherein a non-native gene is incorporated into the adenoviral genome. Subsequently, the adenoviral particle can be targeted specifically to target cells of interest; the adenovirus binds to that specific cell either through capsid-receptor binding or through other means and delivers the transgene. Targeting of adenoviruses can be performed in many different ways. Persons skilled in the art of adenoviral vector targeting will be aware of all the different possibilities that are applied to deliver the adenoviral vectors to the cells of interest. Such possibilities include, but are not limited to, capsid alterations (fiber, hexon and/or penton modifications, such as deletions, swaps between fibers of different serotypes, and additions of peptides and/or other binding moieties), wherein chimeric fibers are produced that recognize a receptor present on the cell of interest or wherein the binding of the penton-base is utilized. Other possibilities are linking targeting moieties to the capsid proteins wherein, for instance, binding peptides, known and strong binding proteins, or antibodies or parts thereof, are linked to the capsid proteins to achieve specific targeting. Such vectors can all be produced using the methods and means provided by the present invention. Therefore, the present invention also discloses recombinant adenovirus vectors, according to the invention, further comprising a sequence encoding a non-adenoviral protein. Such sequences can be present on different locations within the adenoviral backbone, but, preferably, they are located in the E1 region, which is lacking in the recombinant adenoviral vectors of the invention. The E1 region is complemented by the complementation elements present in the complementing cells. The direction of the promoter, transgene and other regulatory sequences can be directed towards the left-, as well as to the right-inverted terminal repeat.

The present invention can also be used for the production of viral vectors based on adenovirus and/or on other viruses such as the Adeno-Associated Virus (AAV), wherein the combination, such as an Ad-AAV chimeric virus, can integrate into the host-cell genome. Several methods are known in the art for generating integrating adenoviruses. Generally, the invention is also useful for the production of adenovirus forms that (specifically or non-specifically) can integrate.

As mentioned, several non-adenoviral transgenes can be cloned into the recombinant adenoviral vectors of the present invention. These do not only include regulatory nucleic acid sequences such as enhancers, promoters (e.g. strong non-adenoviral promoters such as the cytomegalovirus promoter, the SV40 promoter and the RSV promoter) and polyadenylation signals, but also heterologous genes for therapeutic purposes. Therefore, in one aspect of the invention, recombinant adenovirus vectors according to the invention are provided, wherein the non-adenoviral protein is selected from the group consisting of: a cell-death-inducing polypeptide, a tumor-specific antigen, a viral protein, a hormone and a cytokine. Non-limiting examples of non-adenoviral factors, proteins, polypeptides and peptides are transcription factors, intracellular signaling proteins, phosphatases, kinases, apoptosis-inhibiting factors, receptor antagonists, soluble forms of membrane-bound receptors, RNA inhibitors, anti-sense RNA's, decoy factors, ribozymes, and more specifically, thymidine kinase, erythropoietin, novel-erythropoiesis-stimulating protein (NESP), IL3, ceNOS, gamma-interferon and gp100. Non-adenoviral viral proteins can be cloned into the recombinant adenoviral vectors provided by the methods and means of the present invention for vaccination purposes. Such viral proteins include, but are not limited to, gag, pol, env, nef, etc., for HIV vaccines, E6 and E7 proteins for Human Papilloma Virus vaccines, circumsporozoite proteins from Plasmodium protozoa for malaria vaccines, rotavirus components for rotavirus vaccines, ebola proteins for ebola vaccines, the F and G gene products from Respiratory syncytial virus for Respiratory Syncytial virus vaccines, and HA and NA for influenza vaccines, etc.

Adenoviruses according to the invention are preferably human adenoviruses, i.e., derived from or based upon adenovirus that is capable of infecting human cells, but the invention is equally useful for non-human adenoviruses. A person skilled in the art will be aware of the fact that, in addition to all human adenoviruses, numerous non-human adenoviruses have been identified in the art. Obviously, non-human adenoviruses can also be applied to reach the same results as disclosed by the present invention. Non-limiting examples of non-human adenoviruses that can be produced using the methods and means of the present invention are canine, bovine, monkey, and avian adenoviruses. "Serotypes," as used herein, therefore, goes beyond species-restricted serotypes.

"Derived from," as used herein, means that nucleic acid sequences, genes, or proteins that are normally found in an adenovirus, are used for the generation of recombinant adenoviruses according to the invention. Methods to generate such recombinant adenoviruses are well known to persons skilled in the art, and include, but are not limited to, general molecular biology methods such as cloning of genetic information into desired constellations by use of restriction enzymes and the like. Recombinant adenoviruses can also be based upon adenoviral sequences. "Based upon," as used herein, is meant to include the synthetic construction of genetic information based upon knowledge of such genetic information. Such methods include, but are not limited to, the use of adenoviral genetic material as a template for PCR to construct a new adenoviral construct that is based upon the sequence of the template adenovirus, the construction of completely synthetic genetic information with a desired sequence, e.g., by linking synthetic oligonucleotides to a desired construct and the like. It is to be understood that "derived from" does not necessarily mean a direct cloning of the wild-type DNA. A person skilled in the art will also be aware of the possibilities of molecular biology to obtain mutant forms of a certain piece of nucleic acid. These mutations may render a different functionality, but they may also be silent in a way that certain mutations do not alter the functionality of that particular piece of DNA and its encoded protein. Therefore, the terms "functional part, derivative and/or analogue thereof" are to be understood as equivalents of the nucleic acid they are related to. A person skilled in the art will appreciate the fact that certain deletions, swaps, (point)mutations, additions, etc., may still result in a nucleic acid that has a similar function as the original nucleic acid. It is, therefore, to be understood that such alterations that do not significantly alter the functionality of the proteins, such as the pIX protein, E4-orf6 and E1B-55K gene product, are within the scope of the present invention. It will be clear to those skilled in the art, that the method for obtaining the genetic information encoding the recombinant adenovirus can be varied without departing from the scope of the present invention.

Human adenoviruses have been classified into subgroups A-F, which encompass 51 serotypes (see, e.g., EP 0978566). For some applications, it can be beneficial to use adenoviral vectors derived from or based upon adenoviruses from specific subgroups or from certain serotypes that have a tissue tropism for a desired cell type, e.g., dendritic cells (WO 02/24730). The general absence of neutralizing antibodies in the population against adenoviruses from certain subgroups or from a specific serotype is also an important parameter to determine the serotype of choice (WO 00/70071). Because of the similarity between the subgroup B viruses (see, e.g., Examples 4 and 11), it is expected that the invention is particularly suitable for the adenoviruses of subgroup B. Hence, preferred embodiments of the present invention relate to adenoviral vectors derived from or based upon an adenovirus classified in subgroup B. Subgroup B of human adenoviruses comprises Ad3, Ad7, Ad11, Ad14, Ad16, Ad21, Ad34, Ad35, and Ad50. Preferred embodiments of the present application relate to recombinant adenoviral vectors derived from or based upon Ad35 or Ad11 serotypes. Besides choosing from a serotype for specific applications, so-called chimeric adenoviruses can be used. These comprise parts or all of genetic sequences coding for coat proteins, such as fiber, penton, or hexon, from one or more adenoviral serotypes linked to the remaining genetic information (the "main" adenoviral vector part) from other serotypes, which can be used to decrease immunogenicity or change the tissue tropism of the "main" adenoviral vector (EP 0978566). The "main" part, as used herein, means that it contributes most of the genetic information to the chimeric virus and a chimeric adenovirus will, therefore, be included in the serotype group of the "main" part of such a virus. It will be clear to those skilled in the art that the present invention can also be used for such chimeric adenoviruses when these could face similar instability problems. It can, for instance, be expected that a chimeric adenovirus comprising Ad35 sequences as the main part and comprising a fiber that is derived from or based on, e.g., an Ad11 adenovirus may have similar instability upon propagation as is reported for the Ad35-recombinant adenoviral vectors described here. Hence, when recombinant adenoviruses are mentioned in this application, chimeric adenoviral vectors are also meant to be included in the present invention.

The elements necessary for production and assembly of recombinant adenoviral vectors are well known to the person skilled in the art (described supra; U.S. Pat. No. 5,994, 128; Russell, 2000). Production of E1-deleted recombinant adenoviruses in the form of virions is done in packaging cells, also called complementing cells. Such cells provide in trans the genetic information of the adenovirus lacking in the recombinant adenoviruses necessary to produce recombinant virus (recombinant virions). Well-known packaging cells are 293 cells, 911 cells and PER.C6™ cells (supra). For most purposes, it is preferable to use a packaging cell and a recombinant adenoviral vector that lack overlapping sequences that would otherwise lead to homologous recombination resulting in replication-competent adenovirus (U.S. Pat. No. 5,994,128). PER.C6™, as deposited under no. 96022940 at the European Collection of Animal Cell Cultures at the Center for Applied Microbiology and Research, is, therefore, a very suitable packaging cell for propagating recombinant adenoviruses. Other methods to decrease the generation of replication-competent adenovirus have also been envisaged and concern, for instance, manipulation of adenoviral sequences to reduce the homology between sequences present in the packaging cell and the vector (e.g., Hehir et al., 1996; Robert et al., 2001). Packaging cells can, besides the obligatory E1 region, comprise other adenoviral sequences to complement other adenoviral functions when these are functionally lacking in the recombinant adenovirus used, such as parts or all of E2, E4, and the like. The complementing information in packaging cells can be present either integrated in the genome or as extrachromosomal copies, e.g., on plasmids, vectors, cosmids, and the like. Other methods make use of so-called helper viruses, which comprise genetic information lacking in the recombinant adenovirus. Recombinant adenoviral vectors are also used as so-called helper viruses used for the production of recombinant adenoviruses that contain a genome deleted for most or all adenoviral genes (gutless vectors or helper-dependent adenoviruses). In the final production of such gutless adenoviruses, it is necessary to avoid packaging of the helper adenovirus. A person skilled in the art is familiar with the methods to achieve this, for example, using a site-specific recombinase on an engineered site in the packaging signal to delete this packaging signal. Often, it is necessary to separate remaining helper virus from the desired gutless virus using CsCl-gradient separation. This is easier to achieve when the genome lengths of the helper and gutless virus differ maximally. Therefore, a large helper virus is preferred above a smaller one. As will be clear to the person skilled in the art, the present invention can equally be applied to increase the stability of the recombinant adenovirus by use of a recombinant helper virus having the increased pIX expression, which can be accomplished by the methods described in the present invention. Any cell containing genetic information that can be used to complement the recombinant adenovirus to generate recombinant virus particles, is meant to be included in the scope of the meaning of "packaging cell." It will be clear to the person skilled in the art that the advantage gained by the present invention is not dependent on the packaging cell used.

The genetic information encoding pIX can either be present on the recombinant adenoviral vector or independent from the recombinant adenoviral vector, and such extraviral genetic information can be present either integrated in the genome or as extrachromosomal copies, e.g., on plasmids, vectors, cosmids, and the like. Introducing genetic information into a packaging cell can be done according to a variety of methods, such as transfection by lipofectamine, calcium phosphate precipitation, viral infection, and the like. Such methods are generally well known to the person skilled in the art and the method used for introduction of genetic information is not critical for the scope of the invention. "Functional pIX in expressible format," as used herein, means genetic information encoding pIX in operable linkage to a promoter or other regulatory sequence capable of driving expression of the genetic information encoding pIX in the packaging cell. Introduction of genetic information into the packaging cell can be done either prior to, concomitantly with, or after the introduction of the recombinant adenoviral vector. It was found that constitutive episomal expression of pIX in a 293-based packaging cell line complements the deficiency of pIx mutant adenovirus type 5 (Caravokyri and Leppard, 1995). However, for such applications, special episomal plasmids containing an EBNA1-expression cassette are required and propagation of adenoviral vectors in such cell lines suffers from the disadvantage that parts of the episome very likely will become part of the recombinant adenoviral vector. Hence, in preferred embodiments of the present invention, genetic information encoding functional pIX is present on the adenoviral vector.

In attempts to decrease the amount of recombination leading to replication-competent adenovirus, some authors have used a pIX gene derived from Ad7, a group B virus, which was driven by a mutated pIX promoter of Ad5, to diminish the overlap between the nucleic acids of the Ad5-derived sequence-containing packaging cell and the recombinant adenoviral vector (Robert et al., 2001). However, those experiments were not done to increase the stability of the viral vector and this stability was not measured in those experiments. In the current application, the transcription-regulating sequences of pIX in the adenoviral vector are changed with the purpose of increasing the stability of the virus and/or increasing the capacity for foreign genetic material in virions. The invention demonstrates that a recombinant adenoviral vector derived from Ad35 comprising a pIX gene under the control of an Ad5-derived proximal pIX promoter derived from Ad5 is more stable and can harbor more foreign genetic information than the corresponding virus with the endogenous (i.e., Ad35-derived) proximal pIX upstream sequences. Therefore, the present invention also provides a recombinant adenovirus comprising a functional pIX-coding sequence and having at least a deletion in the E1-region, wherein the pIX-coding sequence is under control of a heterologous promoter, and wherein the recombinant adenovirus is derived from or based upon an adenovirus other than an adenovirus serotype 5. In certain embodiments, the heterologous promoter is a non-endogenous proximal pIX promoter. In preferred embodiments, the genetic information encoding pIX is derived from or based on Ad35 or Ad11. In such embodiments, a preferred non-endogenous pIX promoter is an Ad5 promoter.

In another aspect, the invention provides a recombinant adenoviral vector obtainable by a method according to the invention. Such recombinant adenoviral vectors are useful, e.g., in the preparation of vaccines (WO 00/70071; WO 01/38362; WO 02/24730), as gene delivery vehicles, and the like. Choosing a desired main serotype for such recombinant adenoviral vectors can be used for obtaining vectors with an altered tissue tropism as compared to the much-used Ad5 adenoviral vectors, and/or can be used because they are less immunogenic than such Ad5-derived vectors (WO 00/70071).

For the generation of recombinant adenoviral vectors, it is convenient to clone the transgene into a plasmid (adapter plasmid) containing the left part of an adenovirus lacking E1 sequences and having restriction enzyme sites for cloning. The recombinant adenoviral vector is then generated by homologous recombination with a cosmid comprising the right part of the adenovirus having at the 5' end overlapping sequences with the 3' end of the adapter plasmid (see, Examples in the present application; method described in WO 99/38362). Thus, it is another aspect of the present invention to provide a recombinant nucleic acid sequence comprising an adenoviral left ITR, a packaging signal, other adenoviral sequences with a deletion in the E1 region, at least part of the E1B-55K open reading frame and pIX-coding sequences. In yet another aspect, the invention provides a modified adenoviral pIX gene, wherein the genetic information encoding the pIX protein is not derived from an adenovirus serotype 5 or an adenovirus serotype 7 pIX-encoding sequence. In preferred embodiments, the modified pIX gene comprises a heterologous promoter.

The present invention also relates to a pharmaceutical composition comprising a recombinant adenoviral vector according to the invention or obtainable by a method provided by the invention. The pharmaceutical composition further comprises an acceptable pharmaceutical carrier, generally applied by persons skilled in the art of preparation of pharmaceuticals. Furthermore, the present invention relates to a method of treating a human body comprising administering to a human body a recombinant adenoviral vector according to the invention or a pharmaceutical composition provided by the invention.

The invention further provides a recombinant adenovirus packaging cell comprising a recombinant adenovirus according to the invention. In one embodiment, the recombinant adenovirus packaging cell comprises a nucleic acid capable of complementing an E1B-55K deficiency of the recombinant adenovirus and wherein the recombinant adenovirus comprises a nucleic acid molecule comprising a part of the sequence encoding a E1B-55K gene product increasing the expression of the pIX gene, with the proviso that the latter recombinant nucleic acid molecule does not encode a functional E1B-55K gene product, and wherein the cell and the recombinant adenovirus do not comprise sequence overlap leading to the formation of a recombinant adenovirus comprising a nucleic acid encoding a functional E1B-55K protein. This embodiment is particularly useful for preventing the formation of recombinant adenoviruses comprising additional adenovirus function.

The present invention furthermore discloses methods and means that solve certain difficulties related to diminished complementation of non-group C adenoviral vectors in Ad5-packaging/complementing cells. Although in the Ad5-complementing cell lines functional Ad5-E1B-55K expression is present, it was found that only very low titers of adenoviral vectors could be produced when the adenoviral backbone was of a non-group C adenoviral origin; this finding implies a serotype-specificity in the interaction of E1B-55K with another (viral) protein. It is disclosed herein that this serotype-dependency can be circumvented by providing E4-orf6 protein compatible with the E1B-55K protein provided by the complementing cell line. As discussed herein, E1B-55K and E4-orf6 form a complex that is involved in inhibiting transport of cellular mRNAs from the nucleus to the cytoplasm, while the complex is also involved in stimulation of transport of viral mRNAs from the nucleus to the cytoplasm (reviewed in Leppard 1997 and 1998). It has been observed by the present inventors that proper complementation of viral vectors in packaging cells requires the presence of E1B-55K and E4-orf6 gene products that are compatible. Packaging cells are also referred to as complementing cells if the cells comprise certain sequences encoding proteins that complement functions not provided by the vector that should be packaged. "Compatible," as used herein, therefore, means that a complex between the available E1B-55K gene product is able to form a functional complex with the available E4-orf6 gene product in a sense that this protein complex supports viral replication, propagation and/or packaging to a level that is comparable to the wild-type situation or that is comparable to the situation found when a recombinant adenovirus serotype 5 vector is produced on a Ad5-complementing cell line such as 293 or PER.C6™. Vector replication in packaging cells is efficient if, during the production period in which the virus is formed, the cell comprises at least an E1B-55K protein and an E4-orf6 protein that are compatible. Preferably, the E1B-55K and E4-orf6 sequences are from adenoviruses within the same adenovirus subgroup (such as A, B, C, D, E or F). More preferably, the E1B-55K and E4-orf6 sequences are from the same serotype. Since established cell lines are available in the art that are capable of supporting the growth of adenoviruses of subgroup C, such as serotype 5, it is even more preferred that the E1B-55K and E4-orf6 genes are derived from adenovirus serotype 5. As will be understood by the skilled person, compatibility may be determined in complementation tests or assays as such are in the realm of those skilled in the art of adenoviral vector production. The person skilled in the art will also understand that the present invention can also be used for the production of any adenovirus serotype on any complementing cell line as long as the E1B-55K and E4-orf6 proteins are compatible.

It has further been observed that the E4-orf6 gene product "matching" with the E1B in the complementing cell line can be provided by the adenoviral vector by replacing the E4-orf6 in the adenoviral vector of choice with an E4-orf6-encoding sequence that is compatible with the E1B gene present within the packaging cell line. This modification was surprisingly found not to have a severe effect on the stability, replication, packaging, assembly and production of the vector.

It is a specific aspect of the invention that one is now able to efficiently produce adenovirus serotypes different from those in subgroup C on cell lines normally applied for the production of adenovirus serotype 5 or other serotype from subgroup C, such as serotypes 1, 2 and 6. The present invention provides methods for the production of non-group C adenoviruses without the necessity of separately providing the complementing (packaging) cell with E4-orf6 because the E4-orf6 sequence that is compatible with the complementing E1B-55K sequence is incorporated in the adenoviral backbone.

The present invention provides a recombinant adenovirus vector comprising structural and non-structural elements of an adenovirus of a first serotype, wherein the vector further comprises a sequence encoding a functional E4-orf6 protein or a functional part, derivative and/or analogue thereof, wherein the sequence is selected from the group consisting of: a) an E4-orf6-encoding sequence derived from an adenovirus of a second serotype different from the first serotype; b) an E4-orf6-encoding sequence derived from an adenovirus of the first serotype comprising a deletion, mutation, addition and/or substitution in one or more codons; and c) an E4-orf6-encoding sequence comprising a fusion between a part of an E4-orf6-encoding sequence derived from a second serotype different from the first serotype and a part of an E4-orf6-encoding sequence derived from a third serotype, wherein the third serotype may be identical to or different from the first serotype. In one embodiment, the present invention provides a recombinant adenovirus vector according to the invention, wherein the first serotype and the second serotype are from different adenovirus subgroups. In a preferred embodiment, a recombinant adenovirus vector according to the invention is provided, wherein the first serotype is from a subgroup other than subgroup C and wherein the E4-orf6-encoding sequence is derived from an adenovirus serotype of subgroup C. More preferred is a recombinant adenovirus according to the invention, wherein the first serotype is from subgroup B and the second serotype is from subgroup C. Even more preferably, the E4-orf6-encoding sequence is derived from adenovirus serotype 5. The recombinant adenoviruses of the invention comprise structural and non-structural elements. Examples of structural elements are the genes encoding the capsid proteins, such as fiber, hexon and penton proteins, as well as the gene products itself. Examples of non-structural elements are the early genes that are expressed upon infection into a cell and that are down-regulated when the infection cycle proceeds. Other examples of non-structural elements are the genes encoding the proteins active during replication, such as pol and pTP.

Some alterations in the nucleic acid, such as a deletion, mutation, addition and/or substitution in one or more codons may significantly change the structure and/or functionality of the encoded gene product. The present invention, therefore, also relates to E4-orf6-encoded sequences that are derived from the same adenovirus serotype as the backbone harboring the genes, for instance, the structural and non-structural elements, but wherein the E4-orf6-encoding sequence has been mutated such that it has become compatible with the E1 proteins (such as the E1B-55K gene product) present in the complementing cell in which the adenoviral vector is to be produced. The codon may be altered completely to change the encoded amino acid, but it may also be mutated partly to change the encoded amino acid. Deletions of nucleic acids may result in loss of one or more encoded amino acids, while it may also result in frame shifts. The present invention also relates to E4-orf6 sequences present in the adenoviral nucleic acid that comprise different parts derived from different serotypes, wherein the domains that render the protein functional in compatibility may be used from one serotype, while the remainder of the E4-orf6 sequence or a part thereof is derived from another (un)related serotype (for instance, from the same subgroup, from different subgroups or from different species, or combinations thereof). It is, therefore, also within the scope of the present invention to apply E4-orf6-fusion proteins that are compatible. Such fusion protein may be the product of several pieces of nucleic acid.

A person skilled in the art will be aware of the fact that besides all human adenoviruses, numerous non-human adenoviruses have been identified in the art. Obviously, non-human adenoviruses can also be applied to reach the same results as disclosed by the present invention. It will be clear to the skilled person that compatibility between E1B-55K and E4-orf6 may not be limited to human adenoviruses but also elements from adenoviruses specific for different species can be compatible. Thus, it is also another aspect of the invention that non-human adenoviruses can be produced to high titers on known packaging cell lines available in the art as long as the E1B-55K and E4-orf6 gene products are compatible. Non-limiting examples of non-human adenoviruses that can be produced using the methods and means of the present invention are canine, bovine, ovine, frog, porcine, equine, monkey and avian adenoviruses. Serotypes, as used herein, therefore, go beyond species-restricted serotypes. If, for instance, a monkey adenovirus E4-orf6 gene product is compatible with the E1B-55K provided by the packaging cell, then this combination is within the scope of the present invention. Also, when fusions are applied between different serotypes or between E4-orf6 sequences derived from, for instance, a human and an avian adenovirus that is compatible with the E1B gene of the packaging cell, then that particular combination is also within the scope of the present invention.

The present invention provides a method for producing a recombinant adenovirus vector comprising structural and non-structural elements of an adenovirus of a first serotype, the method comprising the steps of: a) providing a complementing cell harboring an E1B-55K-encoding sequence or a functional part, derivative and/or analogue thereof, derived from an adenovirus of a second serotype in expressible form, with the necessary elements of an adenovirus so as to allow assembly of the recombinant adenovirus vector by the complementing cell, wherein the elements comprise at least some structural and non-structural elements from an adenovirus of the first serotype different from the second serotype and a sequence encoding a functional E4-orf6 protein or a functional part, derivative and/or analogue thereof, which is compatible with the expressible E1B-55K protein in the complementing cell; b) culturing the complementing cell in a medium under conditions allowing for production and assembly of the adenovirus vector to take place; and c) harvesting the recombinant adenovirus vector so produced from the medium and/or the complementing cell, wherein the sequence encoding the compatible E4-orf6 protein is present in the recombinant adenovirus vector so produced.

In one aspect of the invention, a method according to the invention is provided, wherein the E4-orf6-encoding sequence is selected from the group consisting of: i) an E4-orf6-encoding sequence derived from an adenovirus of the second serotype; ii) an E4-orf6-encoding sequence derived from an adenovirus of a third serotype different from the first and second serotypes; iii) an E4-orf6-encoding sequence derived from an adenovirus of the first serotype comprising a deletion, mutation, addition and/or substitution in one or more codons; and iv) an E4-orf6-encoding sequence comprising a fusion between a part of an E4-orf6-encoding sequence derived from a third serotype and a part of an E4-orf6-encoding sequence derived from an adenovirus of the second serotype, wherein the third serotype may be identical to or different from the first serotype. In a preferred embodiment, the first and second serotypes are from different subgroups. In a more preferred embodiment, the second serotype is an adenovirus serotype of subgroup C. In an even more preferred embodiment, the second serotype is adenovirus serotype 5. In another particular aspect of the invention, the first serotype is an adenovirus serotype of subgroup B. Preferably, the first serotype is selected from the group consisting of adenovirus serotypes 11, 14, 16, 21, 34, 35 and 50.

There are several packaging cells known in the art that are used for complementing recombinant adenoviral vectors and to produce, assemble and package the adenoviral particles. Non-limiting examples of such cell lines are HEK-293, 911 and PER.C6™ cells. It is preferred to use cell lines that have already been proven to deliver high titers of adenoviral stocks. Such cell lines express E1 proteins in a stable manner. It is, therefore, a preferred aspect of the invention to use cell lines and methods, wherein the E1B-55K-encoding sequence is integrated into the genome of the complementing cell. More preferred are complementing cells that are derived from a primary, diploid human cell, or a progenitor cell thereof. Even more preferred, the complementing cell is derived from a primary human retinoblast cell, a primary human embryonic kidney cell, a primary human neuronal cell or a primary human amniocyte. Highly preferred is the use of a complementing cell in the methods provided by the present invention, wherein the complementing cell is a PER.C6™ cell or a derivative thereof. PER.C6™ cells are well known in the art for not giving rise to replication-competent adenovirus when adenoviral DNA is used that has no overlap with the nucleic acid provided by the cells. Many of the adenoviral vectors used in the art lack the E1 region. Therefore, in one aspect of the invention, the complementing cell comprises, integrated into its genome, a nucleic acid encoding at least one adenovirus E1A protein. Preferably, the nucleic acid encoding at least one adenovirus E1A protein is derived from an adenovirus serotype of a subgroup different than subgroup B. More preferably, the nucleic acid encoding at least one adenovirus E1A protein is derived from an adenovirus serotype of subgroup C. Highly preferred are embodiments wherein the nucleic acid encoding at least one adenovirus E1A protein is derived from an adenovirus serotype 5. In another embodiment of the invention, the invention provides a method, wherein the E4-orf6-encoding sequence and the E1B-55K-encoding sequence are derived from different adenovirus serotypes and wherein the different adenovirus serotypes are members of the same adenovirus subgroup. Preferably, the E4-orf6-encoding sequence and the E1B-55K-encoding sequence are derived from different adenovirus serotypes and wherein the different adenovirus serotypes are both members of subgroup C. More preferably, the E4-orf6-encoding sequence and the E1B-55K-encoding sequence are derived from the same adenovirus serotype. Highly preferred are methods wherein the E4-orf6-encoding sequence and the E1B-55K-encoding sequence are derived from adenovirus serotype 5.

The invention also relates to methods in which adenoviral vectors can be produced using the proper complementing/packaging cells and the adenoviral vector of interest. For an efficient production process, it is useful to apply the correct cells with the proper adenoviral vector. Therefore, the invention also relates to a kit of parts (also referred to as "packaging system") comprising: a) a complementing cell for producing a recombinant adenovirus vector comprising structural and non-structural elements of an adenovirus of a first serotype, the cell harboring an E1B-55K-encoding sequence or a functional part, derivative and/or analogue thereof, derived from an adenovirus of a second serotype in expressible form; and b) on one or more replicable nucleic acid vectors, all necessary adenoviral elements so as to allow assembly of the recombinant adenovirus vector by the complementing cell, wherein the elements comprise at least some structural and non-structural elements from an adenovirus of the first serotype different from the second serotype and a sequence encoding a functional E4-orf6 protein or a functional part, derivative and/or analogue thereof, which is compatible with the expressible E1B-55K protein in the complementing cell. Preferably, a kit of parts is used, wherein the E4-orf6-encoding sequence is selected from the group consisting of: a) an E4-orf6-encoding sequence derived from an adenovirus of the second serotype; b) an E4-orf6-encoding sequence derived from an adenovirus of a third serotype different from the first and second serotypes; c) an E4-orf6-encoding sequence derived from an adenovirus of the first serotype comprising a deletion, mutation, addition and/or substitution of one or more codons; and d) an E4-orf6-encoding sequence comprising a fusion between a part of an E4-orf6-encoding sequence derived from a third serotype and a part of an E4-orf6-encoding sequence derived from an adenovirus of the second serotype, wherein the third serotype may be identical to or different from the first serotype.

The invention is particularly useful for the replication of E1-deleted chimeric adenoviruses that are derived almost entirely from a serotype other than adenovirus 5. Such vectors need only to be provided with a nucleic acid encoding adenovirus 5 E4-orf6 or a functional part, derivative and/or analogue thereof. Once provided therewith, the vector can be efficiently replicated on normal adenovirus 5 E1-complementing packaging cell lines. Stability of the vectors is improved and vectors may be complemented for deletions in both E1A and E1B. By providing such vectors with a nucleic acid encoding adenovirus E4-orf6, it is possible to enable efficient plaque purification and good yields in the absence of an additional wild-type contamination problem, when grown on 293 or 911 cells. In PER.C6™, of course, wild-type adenovirus contamination can also be prevented in other ways.

An additional advantage of a recombinant vector of the invention is that there is no need to generate special cell lines of adenovirus E4-orf6 from a nucleic acid integrated into the genome. Although such cell lines exist, production parameters such as scaling up and the like, and/or regulatory issues may not have been resolved up to the same degree as for cell lines such as PER.C6™. This may, at least in part, be due to the fact that with more and more foreign genes inserted into the genome of a cell line, it is difficult to maintain stability of all foreign sequences (or the expression thereof). In the present invention, it was found that at least some of the problems associated with low yields of non-adenovirus serotype 5-based vectors and stability of adenovirus serotype vectors from subgroup B, such as adenovirus serotypes 7, 11 and 35 on adenovirus serotype 5, packaging cell lines can be overcome with a recombinant adenovirus vector of the invention.

It will also be clear that the two main aspects of the invention can be combined to provide for stable recombinant adenoviruses that can grow on convenient packaging cells that are readily available. The invention thus provides a recombinant adenovirus comprising a recombinant nucleic acid molecule having at least a deletion in the E1 region, characterized in that at least part of the sequence encoding the E1B-55K gene product increasing the expression of the pIX gene is present in the recombinant nucleic acid molecule, with the proviso that the recombinant nucleic acid molecule does not encode a functional E1B-55K gene product; the recombinant adenovirus further comprising structural and non-structural elements of an adenovirus of a first serotype, wherein the adenovirus further comprises a sequence encoding a functional E4-orf6 protein or a functional part, derivative and/or analogue thereof, wherein the sequence is an E4-orf6-coding sequence derived from an adenovirus of a second serotype different from the first serotype. Alternatively, or in addition to having at least part of E1B-55K sequences, the nucleic acid may have a pIX gene product that is regulated by a heterologous promoter. Preferably, the second serotype and, hence, the E4-orf6 sequence, is derived from a group C adenovirus, more preferably from an adenovirus serotype 5. Preferably, the first serotype is from a subgroup other than group C, preferably a subgroup B serotype such as Ad11, Ad14, Ad16, Ad21, Ad34, Ad35 or Ad50. In one embodiment, the recombinant adenovirus further comprises a sequence encoding a non-adenoviral protein, polypeptide or peptide. Such recombinant adenoviruses are stable and can grow on readily available packaging cells, such as Ad5-E1-containing packaging cells, preferably PER.C6™ cells, when E4-orf6 in the recombinant adenovirus is compatible with Ad5-E1 gene products, for instance, when E4-orf6 in the adenovirus is derived from Ad5. The prevention of the generation of replication-competent adenovirus or functional E1 protein containing adenoviral particles is a recognized problem in the art and has been solved by preventing overlap between the E1 sequences present in the adenovirus with those in the packaging cell (U.S. Pat. No. 5,994,128). In embodiments of the invention, the combination of e.g., an Ad35-derived adenovirus comprising E1B-55K sequences that increase the stability of the virus by influencing pIX expression with a packaging cell comprising E1 regions from Ad5, will not lead to homologous recombination with the concomitant formation of a recombinant adenovirus comprising a nucleic acid encoding a functional E1B-55K protein. It is, thus, another aspect of the present invention to provide a packaging system comprising a packaging cell and a recombinant adenovirus comprising structural and non-structural elements of an adenovirus of a first serotype, wherein the packaging cell expresses nucleic acid encoding at least an E1B-55K protein or a functional part, derivative and/or analogue thereof, derived from an adenovirus of a second serotype, and wherein the recombinant adenovirus can be replicated in the packaging cell to generate stable recombinant adenovirus, the adenovirus comprising a nucleic acid molecule having a deletion in the E1-region and further comprising a part of the sequence encoding an E1B-55K gene product, the nucleic acid further comprising sequences encoding a functional E4-orf6 protein or a functional part, derivative and/or analogue thereof, which is compatible with the expressible E1B-55K protein in the packaging cell. Preferably the first serotype is Ad 35 or Ad11. Preferably the second serotype is Ad5. More preferably, the packaging cell is PER.C6™. Preferably, the sequences encoding a functional E4-orf6 protein or a functional part, derivative and/or analogue thereof, are derived from an adenovirus of the first serotype. This system will allow replication of the recombinant adenovirus without the concomitant generation of functional E1 protein-containing adenovirus. Alternatively, or additionally, the nucleic acid could contain pIX-coding sequences under the control of an exogenous promoter. It is another aspect of the invention to provide a method for producing a stable recombinant adenovirus comprising structural and non-structural elements of an adenovirus of a first serotype, wherein the recombinant adenovirus comprises a recombinant nucleic acid molecule derived from an adenovirus, which nucleic acid molecule has a deletion in the E1 region and comprises nucleic acid derived from at least part of the sequence encoding the E1B-55K gene product increasing expression of the pIX protein not leading to the expression of a functional E1B-55K protein from the nucleic acid molecule and/or has a pIX-coding sequence under control of a heterologous promoter, the method comprising the steps of: a) providing a complementing cell expressing an E1B-55K-encoding sequence or a functional part, derivative and/or analogue thereof, derived from an adenovirus of a second serotype in expressible form, with the necessary elements of an adenovirus so as to allow assembly of the recombinant adenovirus vector by the complementing cell, wherein the elements comprise at least some structural and non-structural elements from an adenovirus of the first serotype different from the second serotype and a sequence encoding a functional E4-orf6 protein or a functional part, derivative and/or analogue thereof, which is compatible with the expressible E1B-55K protein in the complementing cell and wherein; b) culturing the complementing cell in a medium under conditions allowing for production and assembly of the recombinant adenovirus to take place; and c) harvesting the recombinant adenovirus so produced from the medium and/or the complementing cell. The invention further provides methods for using the recombinant adenoviruses from the invention for treatment of the human or animal body, vaccination, gene therapy, and the preparation of medicaments for treatment of diseases or disorders. The invention also provides pharmaceutical preparations comprising the adenoviruses according to the invention.

The invention will now be illustrated with some examples, which are not intended to limit the scope of the invention.

EXAMPLES

Standard molecular biology methods were used (e.g., Sambrook and Russell, 2001), unless otherwise indicated. Primer sequences are provided in Table IV.

Example 1

PER.C6™-Based Complementing Cell Lines for E1-Deleted Ad35 Viruses

PER.C6™ cells were seeded in 10 cm culture dishes at a density of $3\times10^6$ cells/dish in PER.C6™ culture medium (DMEM (Gibco BRL) complemented with FBS (Gibco BRL) up to 10% and 10 mM $MgCl_2$ (4.9 M stock solution, Sigma)). Two days later, nine dishes were transfected with 1 µg ScaI linearized pIG35.55K DNA (described infra) and nine dishes were transfected with 1.5 µg ScaI linearized pIG35.55K DNA. Separate control dishes were transfected with 1 or 1.5 µg ScaI linearized pAdApt35.LacZ (described in WO 00/70071) to monitor transfection efficiency and with 1 or 1.5 µg ScaI linearized pcDNA.nlsLacZ. pcDNA.nlsLacZ (described in WO99/55132) is a pcDNA3-based plasmid (Invitrogen) with the nlsLacZ gene driven by the CMV promoter. pcDNA.nlsLacZ also contains a $neo^r$-expression cassette. As a negative control, one extra dish was transfected with linearized pAdApt35.LacZ, a construct that lacks the $neo^r$-selection gene. All transfections were performed with the LipofectAmine transfection kit (Invitrogen/Life Technologies) according to the manufacturer's instructions using 5 ml LipofectAmine reagent/µg DNA. Cells were incubated for four hours with the transfection mixture, after which the medium was replaced with PER.C6™ culture medium. The next day, medium was replaced with culture medium containing 0.5 mg/ml G418 (Gibco BRL) except in the two dishes that were transfected with 1 or 1.5 µg pAdApt35.LacZ. These latter dishes were used to monitor LacZ expression two days following transfection. After X-gal staining of these cultures, transfection efficiency was estimated at approximately 40% with slightly more blue cells in the dish transfected with 1.5 µg DNA. Selection medium was refreshed twice weekly in the remaining transfected dishes. Within two weeks following first addition of selection medium, most cells in the negative control dish (transfected with 1.5 µg pAdApt35.LacZ) were dead. In the dishes transfected with pcDNA.nlsLacZ, cell clones were becoming visible. Since the cells transfected with pIG35.55K seemed to be more resistant to G418, the concentration was raised to 0.75 mg/ml three weeks following transfection. Three days and seven days later, a total of 196 cell clones were picked from the dishes transfected with pIG35.55K and seeded in separate wells of 96-well plates.

Cells remaining after colony picking of two 10 cm dishes of the transfection with 1 µg pIG35.55K DNA were trypsinized, pooled and expanded to give pool PER55K (1.0). The same was done for two dishes of the 1.5 µg transfection. The PER55K(1.0) cell pool was expanded and seeded in four T25 flasks at a density of $3.5\times10^6$ cells/flask for transfection to test virus generation. In addition, three T25 flasks with parental PER.C6™ cells were seeded at the same density. pAdApt35.eGFP (an adapter plasmid based on pAdApt35IP1 (described in WO 00/70071) but also containing the green fluorescent protein as marker gene, which was cloned into pAdApt35IP1 as HindIII-BamHI fragment derived from pIPspAdapt.eGFP (described in WO 02/24933)) was digested with PacI to liberate the adenoviral sequences from the plasmid backbone. pWE.Ad35.pIX-rITR (described in WO 00/70071) was digested with NotI to liberate the adenoviral sequences from the cosmid backbone. Two flasks with PER.C6™ cells and two flasks with PER55K(1.0) cells were transfected with 2 µg digested pAdApt35.eGFP and 6 µg digested pWE.Ad35.pIX-rITR each. One flask of each cell line was transfected with 8 µg pAdApt35.LacZ to monitor transfection efficiency. The remaining flask with PER55K(1.0) cells served as a negative control and was treated as the others but did not receive the transfection mixture. All transfections were performed with LipofectAmine (Invitrogen/Life Techn.) according to the manufacturer's instructions using for each transfection a total of 8 µg DNA and 40 µl LipofectAmine reagent. The transfection mixture was removed and after four hours incubation, fresh culture medium was added. Transfections were done the day after seeding of the cells and again two days later. Cells in the T25 flasks were transferred to a T80 flask except for the LacZ control transfections. These were stained with X-gal solution after mild fixation. After five hours incubation with staining solution, the percentage of blue cells was estimated at approximately 90% in both flasks showing that transfection went well for both cell lines. Four days following the passage to the T80 flasks, the transfected PER55K(1.0) cultures showed starting CPE (cytopathogenic effect, indicative of virus replication) with approximately 100 events/flask. The untransfected PER55K(1.0) cells were grown confluent with no evidence of CPE. In the transfected PER.C6™ cultures, only three CPE events were visible in the confluent monolayer of cells. Again three days later, the transfected PER55K(1.0) cultures showed full CPE, with all cells rounded and detached in clumps. In contrast, in the PER.C6™ cultures, the few events of CPE had not progressed and cells were still in monolayer. This confirms earlier observations that generation of E1-deleted Ad35-based viruses on PER.C6™ is very inefficient. Also, the untransfected PER55K(1.0) cultures showed, as expected, a confluent monolayer with no CPE. The cells and medium in the PER55K(1.0) flasks with full CPE were harvested and subjected to two freeze/thaw cycles, after which the cell debris was removed by centrifugation at 3000 rpm for ten minutes in a table centrifuge. One of the resulting crude lysates was used to infect a fresh culture of PER55K(1.0) cells in a T175 flask (1.5 ml/flask). Cells and medium were harvested at full CPE four days later. This shows that infectious virus had formed in the initial transfections. GFP expression was confirmed by fluorescent microscopy of A549 cells infected with the crude lysate. The crude lysate was then used to analyze complementation of this E1-deleted Ad35.AdApt.eGFP virus in the individual clones as described below.

The above-described clones that were picked from the pIG35.55K-transfected PER.C6™ cells were expanded and functionally tested for the ability to sustain replication of Ad35.AdApt.eGFP. Hereto, the clones were seeded at two densities in 6-well plates and one day later infected with 15 ml of the above-described crude lysate. CPE was monitored the day after. Of the 146 clones tested in this way, 19 gave full CPE at day two or three and 68 gave full CPE at day five or six. The remaining clones had only partial CPE or showed a few non-progressing events. The latter were indistinguishable from PER.C6™ cells that were taken along as a negative control.

Based on these results, a selection of 24 clones was made that were further screened for the ability to generate recombinant E1-deleted viruses following transfection of the pAdApt35.GFP adapter plasmid and the large pWE.Ad35.pIX-rITR cosmid clone. Hereto, clones were plated in T25 flasks and transfected with 2 µg of the adapter and 6 µg of the backbone plasmid using LipofectAmine as described above. Two days following the transfection, cells were transferred to T80 flasks to prevent overconfluency of the cultures. Of the 24 clones, five gave full CPE three days after passage to T80 and another 13 clones gave progressing to full CPE the day after. The remaining 6 clones showed no CPE or only starting. In comparison: routine generation of E1-deleted Ad5 vectors on PER.C6™ cells generally results in full CPE four to six days after transfer to T80 flasks.

This shows that the new clones efficiently complement E1-deleted adenovirus vectors. One of the clones (clone #16) described above was used to generate and produce multiple batches of E1- and E1/E3-deleted Ad35 viruses containing different transgenes. Hereto, virus in crude lysates resulting from transfections as described above but using different adapter plasmids, were plaque-purified on the new cell line. Single plaques were tested for transgene activity and then amplified for medium-scale production in four to eight triple layer flasks (3×175 cm/flask). Cells were harvested at full CPE and the virus was released and purified as routinely done for adenoviruses. The amount of virus particles was determined by HPLC (Shabram et al., 1997). Table I presents the yields after downstream processing of medium-scale productions of E1- and E1/E3-deleted Ad35 viruses on triple layer flasks with PER55K clone #16 cells. The amount of purified virus particles is comparable with the yields of Ad5-based vectors on PER.C6™ cells.

We conclude that we have generated multiple cell lines that efficiently complement fully E1-deleted Ad35-based vectors. Thus, Ad35-E1B-55K expression in an Ad5-complementing cell line facilitates replication of Ad35 vectors.

Example 2

Generation of pWE.Ad.pIX-rITRΔE3

The early region-3 of human adenoviruses contains multiple coding regions for proteins that interfere with the host immune response to adenoviral infection. When adenoviral vectors are used as vaccine carriers, such interference is unwanted. Therefore, we constructed an Ad35 backbone cosmid lacking the E3 region.

Figure 15:
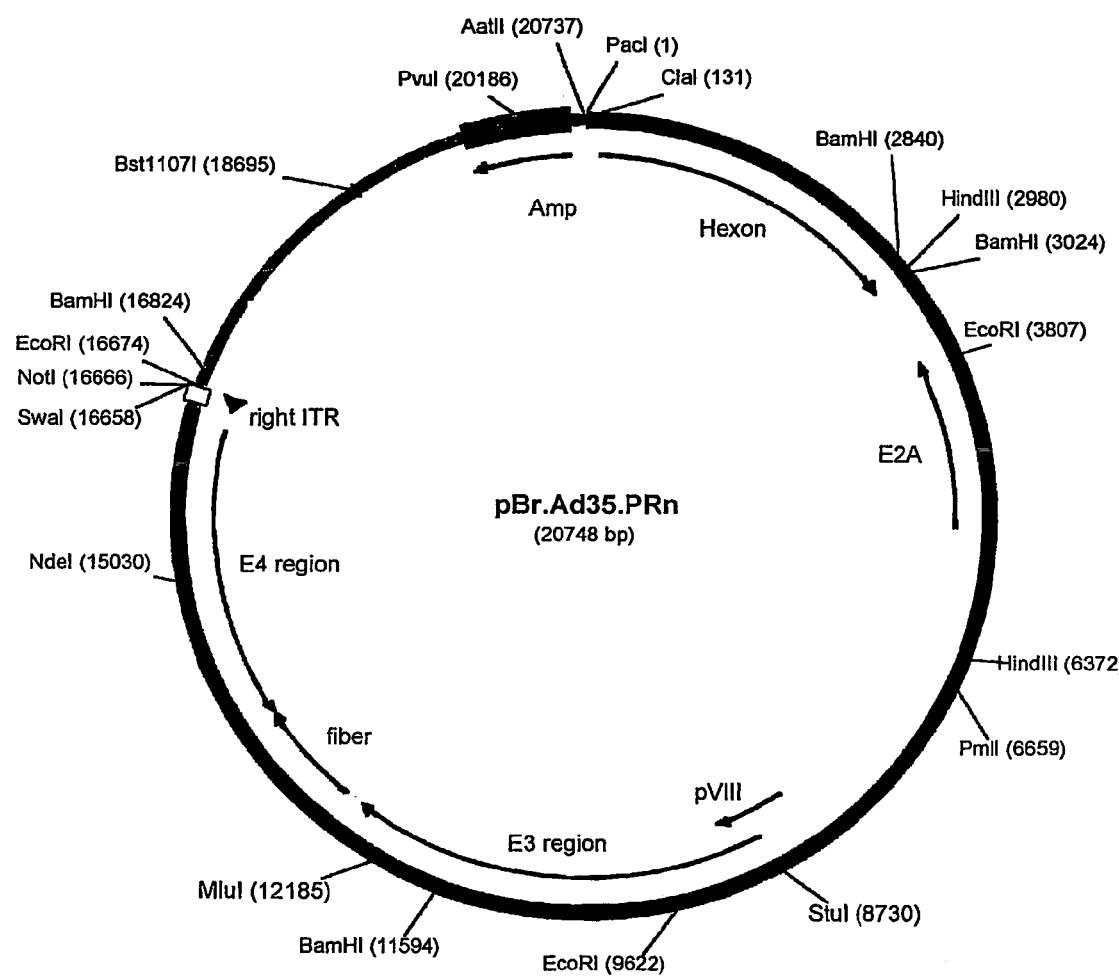
FIG. 15. Schematic representation of pBr.Ad35.PRn.

Hereto, construct pBr.Ad35.PRn (FIG. 15; described in Example 13 in publication EP1054064) was digested with StuI and MluI and the 17.3 kb vector fragment was purified from low melting-point (LMP) gel using agarase enzyme (Roche) according to the manufacturer's instructions. Next, a PCR fragment was generated on pBr.Ad35.PRn using primers 35E3for and 35E3rev. For the amplification Pwo DNA polymerase (Roche) was used according to the manufacturer's instructions and program set at 94° C. for two minutes, 30 cycles of (94° C. for 30 seconds, 58° C. for 30 seconds and 72° C. for one minute) and a final incubation at 68° C. for eight minutes. The 833 bp PCR product was purified using the QIAquick PCR purification kit (Qiagen) and digested with MluI and StuI. The digested DNA was purified from gel using the QIAquick gel extraction kit (Qiagen). Both isolated fragments were ligated and transformed into DH5α-competent cells (Invitrogen/Life Technologies) to give pBr.Ad35.PRnΔE3 (FIG. 25). The plasmid was checked by restriction analysis and sequencing of the PCR-amplified insert. The E3 deletion was then cloned into the pWE.Ad35.pIX-rITR cosmid backbone. Hereto, pWE.Ad35.pIX-rITR was digested with PacI and the DNA was purified by precipitation with isopropanol and washing with 70% EtOH. Following resuspension in milliQ water, the DNA was digested with SwaI and the 22.8 kb vector-containing fragment was purified from LMP gel using agarase enzyme as above. Construct pBr.Ad35.PRnΔE3 was digested with PacI and SwaI in the same manner and the 16.6 kb fragment was also isolated using agarase enzyme. Both isolated fragments were ligated using 0.5 to 0.6 µg of each fragment. Ligated fragments were then packaged using λ-phage packaging extracts (Stratagene) according to the manufacturer's instructions and mixed with STBL-2 cells. Bacteria were plated on LB+Amp plates and resulting colonies were analyzed for the presence of the correct construct. This gave construct pWE.Ad35.pIX-rITRΔE3

Figure 1:
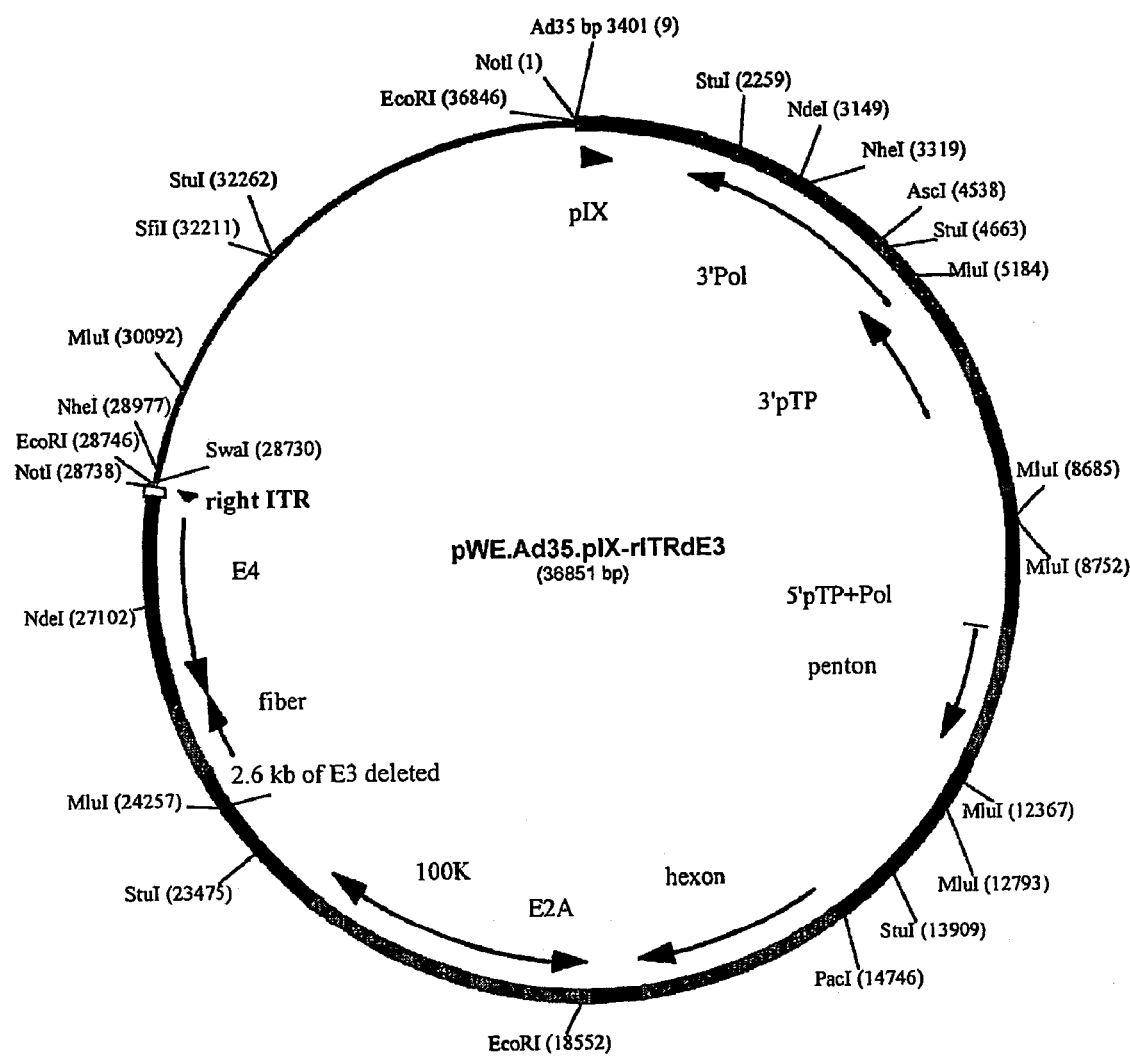
FIG. 1. Map of pWE.Ad35.pIX-rITRΔE3.

(FIG. 1). The E3 deletion extends from nucleotide 27648 to nucleotide 30320 of the Ad35 sequence (described in WO 00/70071) and thus spans a 2.6 kb region.

Co-transfection of NotI-digested pWE.Ad35.pIX-rITRΔE3 and pIPsp-1-(New England Biolabs) digested pAdApt35.eGFP onto PER55-clone #16 cells (described supra) gave rise to GFP-expressing Ad35-based viruses. Upon isolation of viral DNA from these viruses, PCR amplification of the E3 region showed that the viruses were deleted for 2.6 kb of E3 sequences as expected.

Example 3

Limits in Packaging Size of E1-Deleted Ad35-Based Vectors

Ad35-based E1-deleted and E1/E3-deleted vectors containing different inserts were generated by transfection of PER55K-clone #16 cells (see Example 1) with:

1.5 µg of an Ad35 adapter plasmid carrying a specific transgene digested with PacI or pIPsp-1 enzyme to liberate the adenovirus insert from the plasmid vector sequences and, 0.5 µg of either pWE.Ad35.pIX-rITR digested with NotI or with pWE.Ad35.pIX-rITRΔE3 digested with NotI enzyme.

The right flank of the adapter plasmids and the left end of the backbone plasmid contain homologous sequences mediating recombination events that lead to a complete E1-deleted viral genome (as described in WO 00/70071).

Transfections were done with 30 µl Lipofectamine reagent (Invitrogen/Life Technologies) for each set of constructs according to the manufacturer's instructions. Transfection mixtures were added to PER55K clone 16 cells at 70% confluency in T25 flasks. The following combinations were transfected:

1. pAdApt35IP1+pWE.Ad35.pIX-rITR
2. AdApt35IP1+pWE.Ad35.pIX-rITRΔE3
3. pAdApt35eGFP+pWE.Ad35.pIX-rITR
4. pAdApt35eGFP+pWE.Ad35.pIX-rITRΔE3
5. pAdApt35Luc+pWE.Ad35.pIX-rITR
6. pAdApt35Luc+pWE.Ad35.pIX-rITRΔE3
7. pAdApt35LacZ+pWE.Ad35.pIX-rITR
8. pAdApt35LacZ+pWE.Ad35.pLX-rITRΔE3

Adapter plasmids were digested with pIPsp-1 enzyme to liberate the adenovirus sequences from the plasmid vector backbone. pWE.Ad35.pIX-rITR and pWE.Ad35.pIX-rITRΔE3 were digested with NotI prior to transfection for the same reason. Generation of the adapter plasmids and of the pWE.Ad35.pIX-rITR backbone cosmid is described previously in WO 00/70071. Generation of pWE.Ad35.pIX-rITRΔE3 is described supra.

Figure 2:
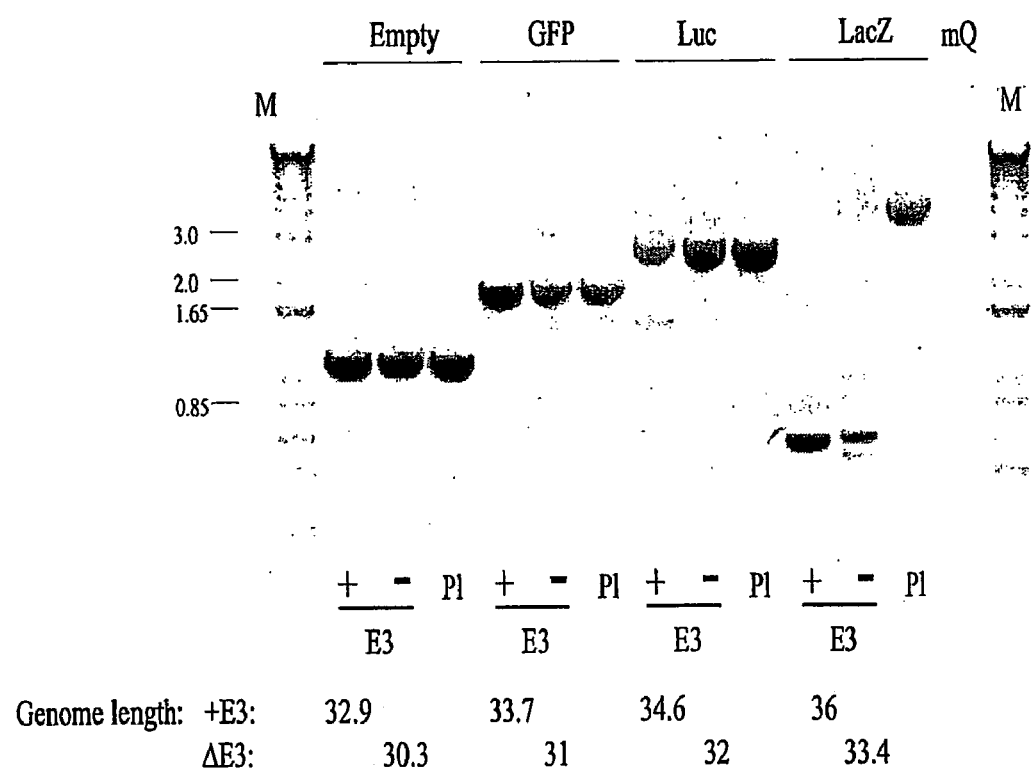
FIG. 2. Gel analysis of PCR fragments generated on Ad35-E1-deleted viruses with and without the E3 region. P1=plasmid control; M=marker: 1 kb plus ladder (Invitrogen); mQ=H$_2$O. Indicated genome lengths are in kb.

Two days following transfection, cells were passaged to T80 and further incubated until full CPE was obtained. Cells and medium were harvested one to two days after full CPE was noticed. The mixtures were subjected to one freeze/thaw cycle and spun down at 1500 rpm for 15 minutes to pellet cell debris, after which supernatants were collected. The crude lysates obtained in this way were used to isolate viral DNA. Hereto, 275 µl of crude lysate material was incubated with 10 µl 10 mg/ml DNaseI at 37° C. for 30 minutes. Subsequently, 6.0 µl 0.5 M EDTA (pH 8.0), 7.5 µl 20% SDS and 1.5 µl 20 mg/ml Proteinase K was added and mixed by vortexing. The mixture was then incubated at 50° C. for one hour. Finally, the viral DNA was isolated using the GeneClean Spin Kit (Bio 101, Inc.). Following elution of the viral DNA in 20 µl milliQ $H_2O$, the transgene region was analyzed by PCR amplification. Hereto, primers AdApt35CMVF and 35pIXR were used. The amplifications were done with 2 µl of the isolated viral DNA using Taq DNA polymerase (Invitrogen). The reaction mixtures contained 5 µl 10× buffer (Invitrogen), 2 µl 50 mM$MgCl_2$, 5 µl 2 mM dNTPs, 3 µl of each primer (10 µM stock) and 2.5 units Taq enzyme in a total volume of 50 µl. The program was set at 94° C. for two minutes followed by 30 cycles of (94° C. for 30 seconds, 60° C. for 30 seconds and 72° C. for four minutes). Control reactions were done on 5 ng of adapter plasmids. After completion of the PCR, 5 µl of the reaction was loaded on gel for analysis. FIG. 2 shows the results for the above-mentioned transfections. The primers amplify sequences from the 5' end of the CMV promoter to the 5' end of the pIX-coding region. As can be seen in FIG. 2, viruses without transgene or with GFP insert show the expected band (compare with the plasmid controls; lanes PL for each virus). Smaller fragments are seen with the larger inserts, luciferase and LacZ, and these deletions become more prominent with larger total length of the virus (compare LacZ or Luc viruses with and without E3). Thus, increasing genome length corresponds with the occurrence of deletions in the transgene region. The fact that the total genome length (also indicated in FIG. 2) of Ad35.AdApt.eGFP and Ad35.AdApt.LacZΔE3, 33.7 and 33.4 kb, respectively, are comparable, while deletions are only found in the LacZ virus sample, indicates that either the sequence or the size of the insert in the former E1 region can also influence the occurrence of the deletions.

Example 4

Sequence Comparison of the pIX Gene Region of Adenovirus Serotypes 5 and 35

The finding that with increasing genome length of recombinant Ad35 viruses, deletions occur in the transgene region could suggest, in analogy with the pIX-deficient Ad5 viruses (Ghosh-Choudhury et al., 1987), that there is a problem with the stability of the capsids.

Figure 3B:
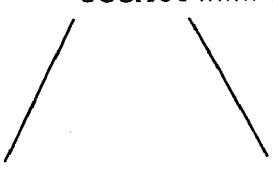
FIG. 3B. Schematic comparison of putative Sp1- and TATA-boxes in proximal pIX regions from sequences given in 3A (SEQ ID NOs:45-54, respectively).

The fact that Ad35.E1B+.AdApt.Luc viruses (where E1A sequences are replaced by the AdApt.Luc cassette) with a total length of 36.7 kb can be made, indicates that the deletion of E1B plays a role. This might be either through a function of one of the E1B proteins itself or through a function of unknown regulatory sequences in this region having influence on expression of other adenoviral proteins. It has, to our knowledge, not been described that the E1B protein itself influences the packaging capacity of adenoviruses. However, it has been described that the E1B-21K protein non-specifically stabilizes transfected DNA (Herrman and Mathews, 1989) and that mutations in the 21K protein result in degradation of cellular and viral DNA during infection (Pilder et al., 1984; White et al., 1984). Since the Ad5-E1B-21K protein is expressed in PER.C6™ cells, these findings do not provide an explanation for our observations. The pIX gene is located directly 3' of the E1B-55K-coding region. For Ad5, it is known that the pIX-promoter and -coding sequences are located within the E1B transcription region since pIX and E1B share the polyadenylation signal. The minimal promoter sequences necessary for pIX expression have been studied in the case of Ad5 (Babiss and Vales, 1991). It was shown that a promoter fragment containing the upstream Sp1 site and the TATA-box sequence was sufficient for pIX expression. The spacing between the Sp1 site and the TATA-box as well as the sequence of the TATA-box itself, were shown to influence the level of pIX expression. Whether the corresponding region in Ad35 is also sufficient to drive pIX expression to a level high enough for stable viruses, is not known. Sequence comparison revealed that both the Sp1 site and the TATA sequence are different from those found in the Ad5-pIX promoter. Using sequence information available from Genbank, a comparison was made of the proximal pIX upstream sequences (i.e., between the stop codon of E1B-55K and the start codon of the pIX gene) of serotypes from different subgroups. The following adenoviruses with SEQ. ID. NOs. and Genbank reference sequences were used for the comparison: Ad2 (SEQ. ID. NO. 45; Genbank NC_001405), Ad5 (SEQ. ID. NO. 46; Genbank M73260), Ad12 (SEQ. ID. NO. 47; Genbank NC_001460), Ad9 (SEQ. ID. NO. 48; Genbank AF099665), Ad40 (SEQ. ID. NO. 49; Genbank L19443), Ad4 (SEQ. ID. NO. 50; NC_003266), Simian 25 (SEQ. ID. NO. 51; Genbank AF394196), Ad7 (SEQ. ID. NO. 54; Genbank AD7001). The Ad35 sequence (SEQ. ID. NO. 52) was as published in WO 00/70071. The Ad11 sequence (SEQ. ID. NO. 53) was not published before and is provided herein. FIG. 3A shows an alignment of the above-mentioned sequences between the stop codon of the E1B-55K protein (first three nucleotides in all sequences) and the start codon of the pIX protein (last three nucleotides). The Sp1 site and the TATA sequence in Ad2 and Ad5 are boxed. In most cases, there is insufficient homology to directly point out the Sp1 and TATA boxes in the other sequences. Therefore, the consensus sequences for GC- and TATA-boxes as published by P. Bucher (1990), was used to identify the putative Sp1 and TATA-box in the various sequences. FIG. 3b shows the putative Sp1 and TATA-box sequences and the spacing between them. Ad12, Ad9 and Ad40, belonging to, respectively, subgroups A, D and F, have Sp1 and TATA sequences that fairly match the consensus sequence. However, the distance between the two boxes is smaller than for Ad5 and Ad2. This is not unusual since the Ad5-E1B promoter also contains an Sp1 box and a TATA sequence with a spacing of 11 nucleotides. However, a deletion of nine nucleotides (of the 20) in the Ad5-pIX-promoter sequence between the Sp1- and TATA-boxes gave reduced pIX levels (Babiss and Vales, 1991). The subgroup B serotypes Ad35, Ad11 and Ad7, as well as the subgroup E virus Ad4, have divergent TATA-box sequences and different spacing between the putative Sp1 sequence and the TATA-box. The proximal pIX region in human adenovirus type 4 is identical to that in the simian adenovirus 25 (CV68), a serotype that recently was proposed as a therapeutic vector (Farina et al., 2001). Thus, for replication-deficient vectors based on non-human adenoviruses, pIX expression may also be insufficient for stable capsids.

It may well be that pIX expression is regulated differently in Ad35 viruses and other human and non-human adenoviruses and that regulatory sequences, or even the promoter sequences themselves, are located further upstream in the E1B sequences, or even more upstream. Alternatively, it is also possible that, since pIX expression is activated by E1A proteins, high levels of pIX expression are obtained in the presence of E1A proteins belonging to the same serotype or subgroup.

We tested whether changing the endogenous proximal pIX upstream sequences into a heterologous promoter to increase pIX expression in the vector, leads to more stable viruses and a better packaging capacity (infra). Alternatively, the pIX function may be delivered in trans via the packaging cell line. As a non-limiting example, we describe recombinant Ad35-based viruses that have a non-endogenous proximal pIX promoter as found in Ad5 viruses and show that these viruses have a better stability than the unchanged recombinant vectors.

Example 5

Generation of Adapter Plasmids with an Ad5-pIX Promoter pAdApt535 is an Ad35 adapter plasmid having part of the Ad5-pIX-promoter sequences but is otherwise identical to Ad35 adapter plasmid pAdApt351P1 (see WO 00/70071). Its construction is described below:

A first PCR fragment was generated with primers SV40for and pIX5Rmfe. The reaction was done with Pwo DNA polymerase (Roche) according to the manufacturer's instructions but with 3% DMSO in the final mix. pAdApt, an adapter plasmid for Ad5-E1-deleted viruses (100 ng; see WO 00/70071) was taken as template. The program was set as follows: two minutes at 94° C. and then 30 cycles of (94° C. for 30 seconds (melting), 52° C. for 30 seconds (annealing) and 72° C. for 30 seconds (elongation)) followed by eight minutes at 72° C. The resulting PCR fragments contain the 3' end of the SV40 polyadenylation signal from pAdApt and the Ad5-pIX-promoter region as present in Genbank Accession number M73260 from nucleotide 3511 to nucleotide 3586 and an MfeI site at the 3' end.

A second PCR fragment was generated as described above but with primers pIX35Fmfe and 35R4. 100 ng pAdApt35IP1 was taken as template, the annealing was set at 58° C. for 30 seconds and the elongation of the PCR program was set at 72° C. for 90 seconds. This PCR amplifies Ad35 sequences from nucleotide 3467 to nucleotide 4669 (sequence numbering as in WO 00/70071) and adds an MfeI site to the 5' end.

Both PCR fragments were then digested with MfeI and purified using the Qiagen PCR purification kit (Qiagen) according to the manufacturer's instructions. Concentration of the purified fragments was estimated by running a sample on agarose gel and approximate equimolar amounts of the two fragments were mixed in a ligation reaction containing 5 μg DNA, 4 μl 10× ligase buffer and 2 μl ligase enzyme (New England Biolabs) in a 40 μl volume. Following an incubation of greater than two hours at room temperature, the mixture was loaded on a 1.2% agarose gel in TAE and the DNA fragments of 1.4 kb length were isolated with the GeneClean II kit (BIO 101, Inc.) according to the manufacturer's instructions.

Figure 4:
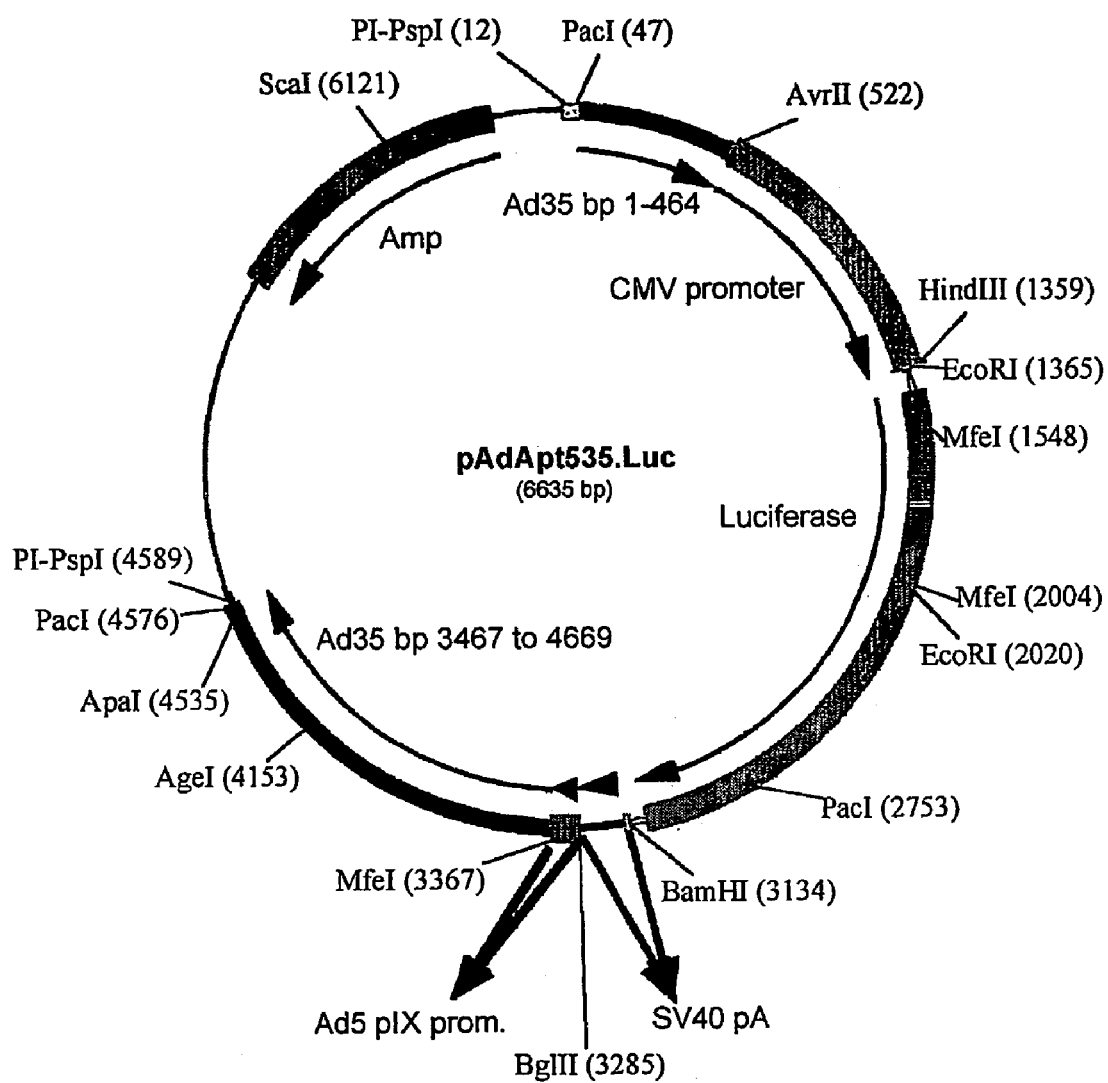
FIG. 4. Map of pAdApt535.Luc.

The DNA was eluted in 30 μl sterile $H_2O$ and 1 μl was used in a PCR amplification reaction with primers SV40for and 35R4 as described above. The PCR was done as described above with an annealing temperature of 52° C. and an elongation time at 90 seconds. The resulting product was isolated from gel using the Qiagen gel extraction kit and digested with AgeI and BglII. The resulting 0.86 kb band was isolated from gel using the GeneClean II kit according to the manufacturer's instructions.

pAdApt35.Luc (described in WO 00/70071) was also digested with BglII and AgeI and the 5.8 kb vector fragment was isolated from gel using the GeneClean II kit as above. This fragment was ligated with the isolated BglII-AgeI fragment described supra containing the Ad5-Ad35 chimeric pIX promoter, to give pAdApt535.Luc (FIG. 4).

Figure 5:
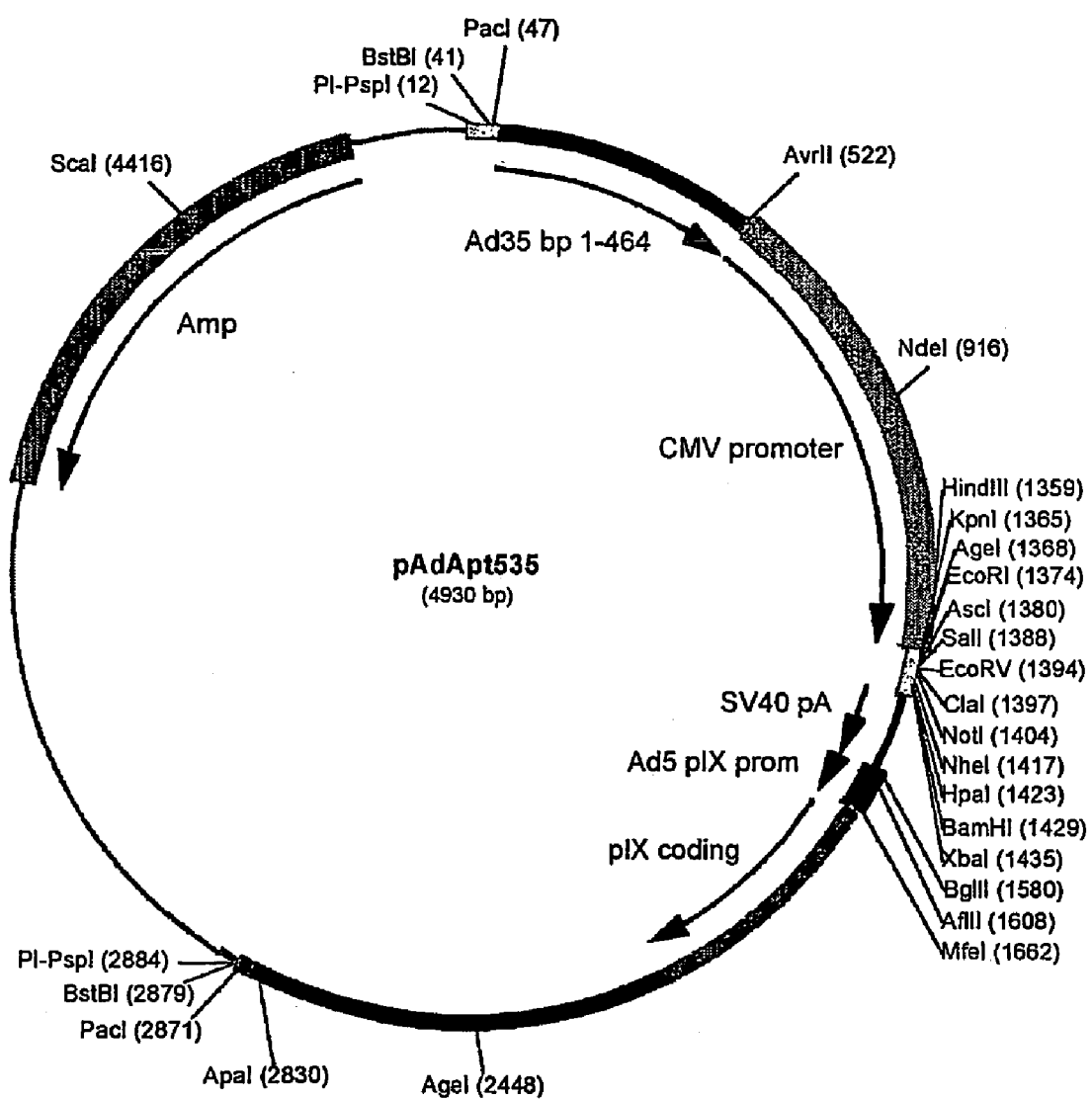
FIG. 5. Map of pAdApt535.

Other adapter plasmids containing the Ad5-pIX promoter were then made as follows:

pAdApt535.Luc was digested with BglII and ApaI and the 1.2 kb insert was purified from gel using the GeneClean II kit according to the manufacturer's instructions.

pAdApt35IP1 was also digested with BglII and ApaI and the 3.6 kb vector fragment was isolated as above. Ligation of both isolated fragments resulted in pAdApt535 (FIG. 5). Next, pAdApt535 was used to clone other marker genes like eGFP (derived from pAdApt35.eGFP) and LacZ (derived from pAdApt35.LacZ) into the multiple cloning site using standard cloning techniques giving rise to pAdApt535.eGFP and pAdApt535.LacZ.

Example 6

Generation of E1-Deleted Ad35-Based Vectors with Adapter Plasmids Containing the Ad5-pIX Promoter Recombinant viruses were generated by transfection of adapter plasmids and Ad35 vector backbone cosmids on PER55K clone 16 cells as described above. Hereto, the following set of plasmids were used:

T1. pAdApt535eGFP+pWE.Ad35.pIX-rITR
T2. pAdApt535eGFP+pWE.Ad35.pIX-rITRΔE3
T3. pAdApt35Luc+pWE.Ad35.pIX-rITR
T4. pAdApt535Luc+pWE.Ad35.pIX-rITR
T5. pAdApt535Luc+pWE.Ad35.pIX-rITRΔE3
T6. pAdApt535LacZ+pWE.Ad35.pIX-rITR
T7. pAdApt535LacZ+pWE.Ad35.pIX-rITRΔE3
T8. pAdApt35LacZ+pWE.Ad35.pIX-rITR
T9. pAdApt35LacZ+pWE.Ad35.pIX-rITRΔE3

AdApter plasmids were digested with PacI except pAdApt535.Luc and pAdApt35.Luc, which were digested with pIPsp-1 enzyme and pWE.Ad35.pIX-rITR and pWE.Ad35.pIX-rITRΔE3, which were digested with NotI prior to transfection. 2 μg of each adapter plasmid and 6 μg of the backbone DNA were mixed with 40 μl Lipofectamine (Invitrogen/Life Technologies) according to the manufacturer's instructions and incubated with PER55K clone 16 cells in T25 flasks at 70% confluency. Transfection medium was removed after four hours and cells were further incubated at 37° C./10% $CO_2$. Two days after transfection, cells were passaged to a T80 flask and scored for occurrence of cytopathogenic effect (CPE) the days after. Five days later, all cultures showed progressing or full CPE except T6 (no CPE) and T8 (CPE events). Again two days later, T6 and T8 showed starting CPE and all others full CPE. All cultures were harvested by collecting medium and cells. The mixtures were stored at −20° C. Upon thawing of the samples, the mixtures were spun down at 1500 rpm for 15 minutes to pellet cell debris and supernatant were collected. In some of the samples (the four LacZ-expressing viruses, T6 to T9), 2 ml was used to infect again PER55K clone 16 cells at 80% confluency in a T80 flask to further amplify the virus titer. Cells and medium were harvested upon progressing (T6+T8) or full CPE (T7+T9) and crude lysates were prepared as described above.

The crude lysates obtained in this way were used to isolate viral DNA. Hereto, 275 μl of crude lysate material was incubated with 10 μl 10 mg/ml DNaseI at 37° C. for 30 minutes. Subsequently, 6.0 μl 0.5 M EDTA (pH 8.0), 7.5 μl 20% SDS and 1.5 μl 20 mg/ml Proteinase K was added and mixed by vortexing. The mixture was then incubated at 50° C. for one hour. Finally, the viral DNA was isolated using the GeneClean Spin Kit (Bio 101, Inc.). Viral DNA was eluted in 50 μl milliQ $H_2O$ and 5 μl samples were used to analyze the transgene region. It should be noted that the pWE.Ad35.pIX-rITR+/−E3 backbone cosmids were unchanged and, therefore, still contain the Ad35-pIX promoter. Since this promoter is located at the very 5' end of the cosmid, the chances for a recombination event resulting in the wild-type Ad35 promoter were considered to be small. However, it could not be excluded in this set-up that viruses would be generated that still contain the Ad35-pIX promoter. Therefore, two specific PCR amplifications were performed on each virus preparation. The first was done with primer set 1 (Ad35-specific): AdApt35CMVF and AdApt35pIXrev. This PCR specifically amplifies the transgene region in viruses containing the Ad35-pIX promoter. The PCR reaction was done on 5 μl of the isolated viral DNA samples with recombinant Taq polymerase (Invitrogen) according to the manufacturer's instructions but with using 4 mM MgCl2 and 4 units Taq enzyme in the reactions. The PCR program was set at 94° C. for two minutes followed by 30 cycles of (94° C. for 30 seconds, 60° C. for 30 seconds and 72° C. for five minutes) and ended with a final step of eight minutes at 68° C.

The second was done with the primers AdApt35CMVF and pIX5Rmfe and, thus, specifically amplifies the transgene region in viruses containing the Ad5-pIX promoter (primer set 2).

PCR amplification was done on 5 μl of the isolated viral DNA using Pwo DNA polymerase (2.5 units/μl Genaxis) in 50 μl volume containing 0.3 μl of each primer (100 μM stock), 5 μl 2 mM dNTP mixture, 5 μl 10× complete buffer (incl. Mg2+), 1.5 μl DMSO and 0.8 μl Pwo enzyme. The PCR program was set at 94° C. for two minutes followed by 30 cycles of (94° C. for 30 seconds, 60° C. for 30 seconds and 72° C. for five minutes) and ended with a final step of eight minutes at 68° C. During PCR the heating and cooling ramps were set at 2° C./second. Then, 5 μl loading buffer was added to the samples and 8 μl of the mixture was loaded on gel for analysis.

Figure 6A:
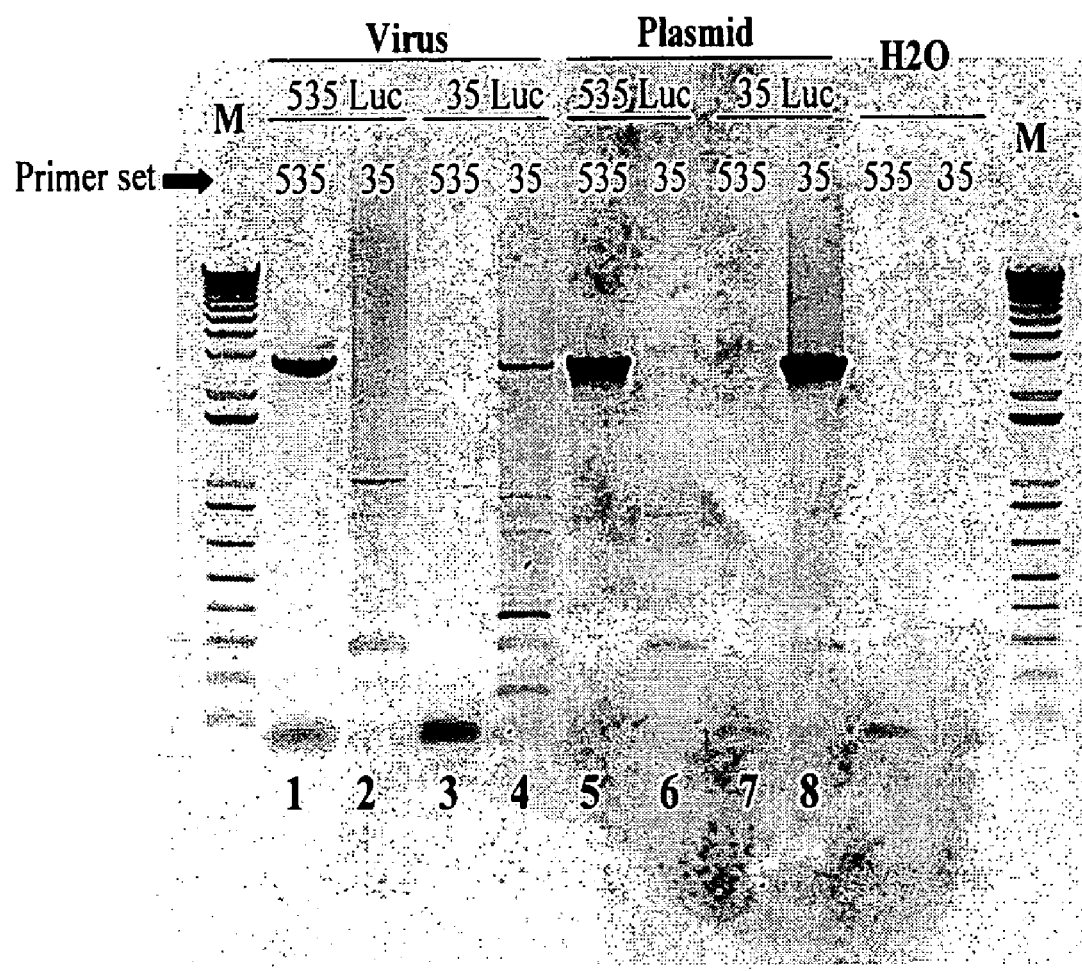
FIG. 6A. Gel analysis of PCR fragments generated on DNA isolated from Ad35.AdApt.Luc and Ad35.AdApt535.Luc viruses or generated on plasmid controls. M=Marker (1 kb plus ladder, Invitrogen). Each virus preparation or plasmid control is analyzed with two specific PCR amplifications.
Figure 6B:
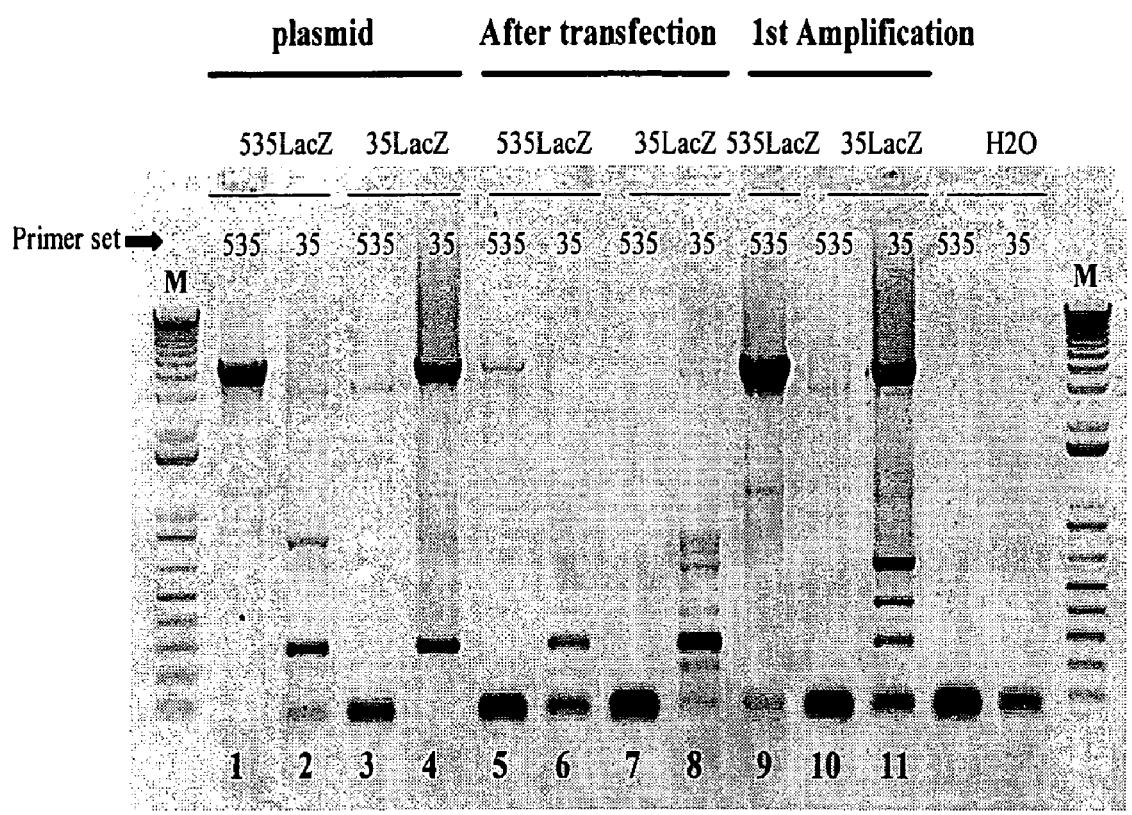
FIG. 6B. Gel analysis of PCR fragments generated on Ad35.AdApt.LacZΔE3 (35LacZ) and Ad35.AdApt535.LacZΔE3 (535LacZ) viruses or generated on plasmid controls.

The E1- and E1/E3-deleted Ad35 viruses containing the Ad5-pIX-promoter sequence and eGFP transgene (transfections T1 and T2) had PCR-amplified bands at the expected height with no shorter fragments. FIG. 6a shows the results for the PCR amplifications on the E1-deleted Luciferase carrying viruses (transfections T3 and T4). Lanes 5-8 are the control PCRs on AdApt535Luc (lanes 5 and 6) and AdApt35Luc plasmids (lanes 7 and 8) with both primer sets. Lanes 1-4 are PCRs on the viral DNA isolates. Primer set 1 (specific for Ad35-pIX region) amplifies a band of the expected length and shows, in addition, shorter fragments on Ad35.AdApt35.Luc viruses (lane 4; compare also FIG. 2 Luciferase+E3). In contrast, primer set 2 (specific for the Ad5-pIX promoter) only shows a band of the expected length with no deletion fragments when viruses are made with the AdApt535.Luc plasmid (lane 1). From this, we conclude that the insertion of Ad5-piX-promoter sequences increases the stability and the packaging capacity of Ad35-E1-deleted viruses. FIG. 6b confirms these results for Ad35-E1/E3-deleted viruses carrying LacZ as transgene. Lanes 1-4 are the control PCRs on AdApt535.LacZ and AdApt35.LacZ plasmids with each primer set. Some background bands are seen especially with primer set 1 (lanes 2 and 4) but a strong specific band is also seen at the expected height for each primer set on the homologous samples (lanes 1 and 4). Viral DNA was isolated after transfection and after one amplification round as described above. Strikingly, primer set 2 generates the expected fragment on Ad35.AdApt535.LacZ viruses with no deletion fragments (lanes 5 and 9), whereas, the sample with viruses containing the Ad35-pIX-promoter sequence clearly shows deleted fragments in addition to a fragment of the correct length (visible after amplification (lane 11).

Altogether, these results show that substitution of the Ad35-pIX-promoter sequences for Ad5-pIX-promoter sequences increase the stability of the transgene region in viruses with larger genomes. Stronger promoters or additional promoter elements may even enhance this effect.

Example 7

Generation of pWE.Ad35-3481

As indicated above, the adenovirus insert in the cosmid pWE.Ad35.pIX-rITR contains the Ad35-pIX promoter at its 5' end. This could lead to re-insertion of the Ad35-pIX promoter into viruses generated with the pAdApt535-based adapter plasmids. Therefore, a new version of the Ad35 backbone cosmid is made that lacks pIX-promoter sequences. Hereto, a PCR fragment was generated with the pIXcosF-2 and Adapt35-3 primers. The amplification was done with Pwo DNA polymerase (2.5 units/µl; Genaxis) in 50 µl volume containing 3 µl of each primer (10 µM stock), 5 µl 2 mM dNTP mixture, 5 µl 10× complete buffer (incl. Mg2+), 1.5 µl DMSO, 0.5 µl Pwo enzyme and 10 ng pAdApt351 P1 template. The PCR program was set at 94° C. for two minutes followed by five cycles of (94° C. for 30 seconds, 58° C. for 30 seconds and 72° C. for 1.5 minutes) and then 25 cycles of (94° C. for 30 seconds, 60° C. for 30 seconds and 72° C. for 1.5 minutes) and ended with a final step of eight minutes at 68° C. The resulting 1.2 kb PCR product contains Ad35 sequences from nucleotide 3481 to nucleotide 4663 (numbering according to Ad35 sequence as published in WO 00/70071) with an AatII and NotI site attached to the 5' end. The PCR product was purified using the PCR purification kit (Qiagen) according to the manufacturer's instructions and cloned into the pPCR-Script Amp vector (Stratagene) according to the manufacturer's instructions. The sequence of the cloned fragment is then verified by sequencing and subsequently removed from the construct by digestion with AatII and AgeI. The resulting 780 bp fragment is purified from gel using the GeneClean spin kit (BIO 101, Inc.) according to the manufacturer's instructions.

Construct pWE.Ad35ΔNdeI (described infra) is also digested with AatII and AgeI and the resulting 12 kb vector fragment is isolated from gel using the GeneClean spin kit (BIO 101, Inc.) according to the manufacturer's instructions. Ligation of both isolated fragments results in construct pWE.Ad35-3481 ΔNdeI.

Figure 13:
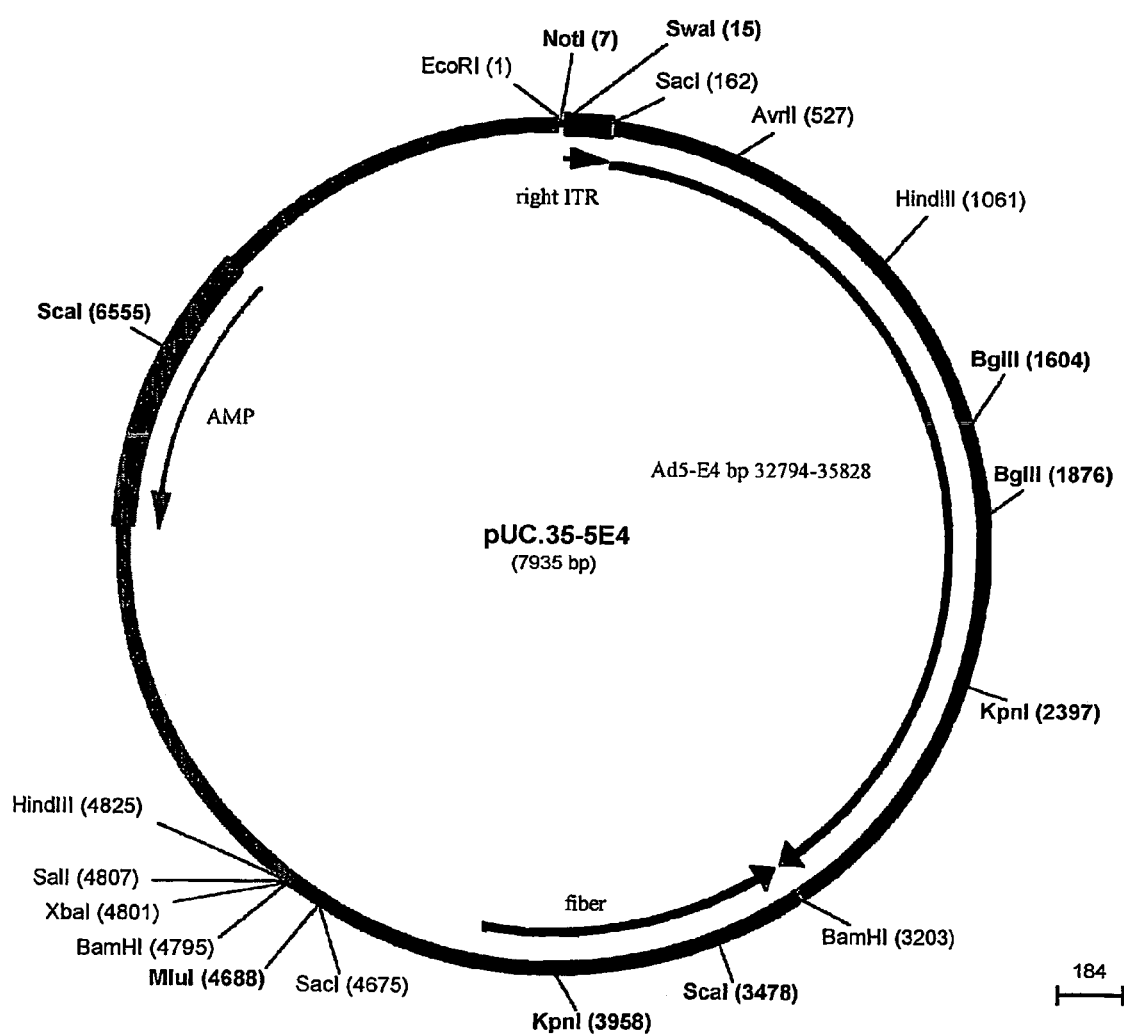
FIG. 13. Schematic representation of pUC.35-5E4.

The construction of construct pWE.Ad35ΔNdeI is described in WO 00/70071 and contains Ad35 sequences from nucleotide 3401 to the NdeI site at nucleotide 6541 and Ad35 sequences from the NdeI site at nucleotide 33167 to the end of the right ITR whereby both Ad35 fragments are linked via the NdeI site (see also FIG. 13 in WO 00/70071).

pWE.Ad35-3481ΔNdeI is then linearized with NdeI, dephosphorylated with CIP enzyme (New England Biolabs) and purified from gel using the GeneClean spin kit (BIO 101, Inc.) according to the manufacturer's instructions. This vector fragment is then ligated to a 26.6 kb NdeI fragment isolated from Ad35 wild-type DNA after which the mixture is used to package the cosmid using λ-phage packaging extracts (Stratagene) according to the manufacturer's instructions. The resulting mixture is used to transform STBL-2 bacteria (Invitrogen), giving rise to pWE.Ad35-3481.

Example 8

Construction of pIG35.55K

Construct pIG35.55K contains the coding sequences of the Ad35-E1B-55K gene operatively linked to the human phosphoglycerate kinase promoter (hPGK) and the HBV polyadenylation sequence. In addition, it contains the neomycin-resistant gene operatively linked to the RSV promoter and HBV pA. The construction of pIG35.55K is described below.

Construct pIG270 (described in WO 00/70071) was digested with EcoRI, treated with Klenow enzyme and purified using a PCR purification kit (Qiagen) according to the manufacturer's instructions. The recovered DNA was then digested with AgeI and the ~5 kb vector fragment was isolated from gel using the GeneClean kit (BIO 101, Inc.) according to the manufacturer's instructions. Next, Ad35-E1B-55K sequences were amplified by PCR on pIG270 template DNA using the 35D21 and 35B3 primers. The PCR amplification was done with Pwo DNA polymerase (Roche) on 2 ng template DNA according to the manufacturer's instructions but with using DMSO at a final concentration of 3% in the PCR mixture. The program was set at: 94° C. for two minutes followed by 25 cycles of (94° C. for 30 seconds, 56° C. for 30 seconds and 72° C. for 30 seconds) and ended by a final incubation of 72° C. for ten minutes. The resulting PCR fragment was purified using the PCR purification kit (Qiagen) and digested with NcoI. Following Klenow treatment to fill in the protruding ends, the DNA was further digested with AgeI and again column purified. The thus treated PCR fragment was then cloned into the above-prepared EcoRI/AgeI-digested vector fragment to give pIG270.ΔE1AΔ21K. pIG270.ΔEIAΔ21K was digested with AvrII and XbaI and protruding ends were filled in using Klenow enzyme. The 2.9 kb fragment containing the PGK promoter and Ad35-E1B-55K sequences was isolated from gel as described above. Next, pRSVneo4 (construction described infra) was digested with BglII, blunted with Klenow enzyme, dephosphorylated and isolated from gel. The blunted AvrII/XbaI fragment from pIG270.ΔE1AΔ21K was then ligated into the above-prepared pRSVneo4 vector fragment to give pIG35.55K.

pRSVneo4 was generated as follows: Construct pRSVh-bvNeo (described in WO 00/70071) was digested with ScaI and BamHI and protruding ends were filled in using Klenow enzyme. The 1070 bp fragment containing part of the Ampicillin gene and the RSV promoter was isolated from gel using the GeneClean kit (BIO 101, Inc.). Next, pRSVh-bvNeo was digested with ScaI and EcoRI, blunted with Klenow and the 3.2 kb fragment containing the neo gene, HBVpA, vector and part of the Ampicillin gene was isolated as above. The two fragments were then ligated to give pRSVneo4.

Example 9

Increased pIX Expression Mediated by the RSV Promoter Increases Stability of Ad35 Viruses As an example of a heterologous promoter driving expression of the pIX gene, the RSV promoter was inserted into the Ad35 adapter plasmids containing the LacZ or Luciferase reporter gene. The RSV promoter corresponds to an NruI/ApaLI fragment obtainable from pRc-RSV (Invitrogen). Protruding ends were filled in using Klenow enzyme (New England Biolabs) according to the manufacturer's instructions. The 388 bp fragment containing the RSV promoter was isolated from agarose gel using the QIAquick Gel Extraction kit (Qiagen). Adapter plasmids pAdApt35.Luc and pAdApt35.LacZ were linearized with BglII followed by Klenow treatment to blunt the ends. BglII digests just behind the SV40 polyadenylation sequence of the transgene-expression cassette. For a description of pAdApt35-based adapter plasmids, see WO 00/70071. The treated adapter plasmids were then dephosphorylated using Shrink Alkaline Phosphatase (SAP) according to the manufacturer's (Roche) instructions. The isolated RSV-promoter fragment was then ligated with each of the treated vectors and transformed into DH5α-competent bacteria (Invitrogen). Colonies were analyzed for forward oriented insertion of the RSV promoter relative to the pIX gene resulting in pAdApt35.Luc.rsv and pAdApt35.LacZ.rsv.

In addition, an adapter plasmid was generated from sequences that were isolated by PCR from an Ad35-recombinant virus that resulted after deletion of the transgene region. Analysis of a crude lysate preparation resulting from a transfection of pAdApt35.LacZ and the pWE.Ad35.pIX-rITR Ad35 backbone constructs and subsequent plaque purification showed that the virus had a deletion in the transgene region of approximately 2.8 kb. The 5' sequences from this virus were PCR amplified from isolated DNA using primers 35F1 and 35R4. The reaction was performed with Pwo polymerase (Roche) according to the manufacturer's instructions. Program settings were as follows: 94° C. for two minutes then five cycles of (94° C. for 30 seconds, 48° C. for 30 seconds, 72° C. for 2.5 minutes) followed by 25 cycles of (94° C. for 30 seconds, 56° C. for 30 seconds, 72° C. for 2.5 minutes), and ended by eight minutes at 68° C.

The resulting 2 kb fragment was purified by the PCR purification kit (Qiagen) and cloned into the pCR-Script-Amp vector (Stratagene) according to the manufacturer's instructions, resulting in pCR.Ad35Δ2.8 kb. This plasmid was sequenced to determine the extent of the deletion. The deletion affected most of the CMV promoter, the transgene and SV40 polyA. This resulted in linking of the 5' 317 bp of the CMV promoter to the Ad35 sequences upstream of the pIX gene. This CMV fragment contains three GC-boxes and a 21-bp repeat (Boshart et al., 1985). Possibly, the remaining sequences of the CMV promoter could augment the pIX expression resulting in a more stable virus. An alternative possibility was that the virus genome being smaller resulted in increased stability. To investigate this, a complete expression cassette was cloned back in the following manner and viruses with this new adapter plasmid were generated. The pCR-Script-based vector containing the amplified sequences (renamed in pCR.C4) had a unique AvrII site preceding the ΔCMV-pIX sequences. The vector was linearized with AvrII, blunted with Klenow enzyme and dephosphorylated using SAP enzyme (Roche) as described above. Adapter plasmids pAdApt535.LacZ (Example 5) and pAdApt.Luc (WO 00/70071) were digested with AvrII and BglII and DNA was treated with Klenow to fill protruding ends. The fragments corresponding to LacZ- and Luciferase-expression cassettes (CMV-TG-pA) were isolated from gel as above and ligated with the AVRII-linearized pCR.C4 vector. Transformation in competent cells as above and selection of colonies that had the cassettes in the forward orientation relative to the left ITR, resulted in pCR.C4.LacZ and pCR.C4.Luc.

Ad35 viruses were generated as described in Example 6 using the new adapter plasmids: pCR.C4.LacZ digested with PacI, pCR.C4.Luc digested with ApaI and pAdApt35.LacZ.rsv and pAdApt35.Luc.rsv each digested with PI-PspI.

The adapter plasmids were co-transfected onto PER55K cells (WO 02/40665) with pWE.Ad35.pIX-rITR or pWE.Ad35.pIX-rITRΔE3 digested with NotI. In addition, adapter plasmid pBr.Ad35.ΔE1AΔ21K.Luc (construction described below) was digested with PI-PspI and co-transfected with pWE.Ad35.pIX-rITR digested with NotI. Upon full cytopathogenic effect (CPE), cultures were harvested by one freeze/thaw cycle and centrifugated to remove cell debris. 300 µl of the resulting cleared lysates were then used to re-infect PER55K cells seeded the day before in T80 flasks. Upon full CPE, crude lysates were prepared and used to infect A549 cells to test for transgene expression and to perform a plaque assay on PER55K cells.

A549 cells were seeded in 6-well plates at $5\times10^5$ cells/well and after five hours infected with 10, 1 or 0.1 µl of each of the LacZ virus stocks and incubated for two days. A549 cells were then stained for LacZ activity and blue cells were counted. The percentage of blue cells is given in Table II.

LacZ-expressing viruses are clearly more stable when the RSV promoter is driving expression of the pIX gene as compared to the deleted CMV promoter. These results are confirmed with the Luciferase viruses. To measure activity of the Luciferase viruses, A549 cells were seeded in 24-well plates at $1\times10^5$ cells/well and infected with 10, 1, 0.1, or 0.01 µl of the virus stocks and incubated. After two days, cells were washed with PBS twice and resuspended in 100 µl lysis buffer (Promega) and stored at −20° C. until use. Luciferase was measured using the Steady-Glo luciferase assay system (Promega) according to the manufacturer's instructions. Results are presented in Table III.

In Example 3, we described that fully E1-deleted Ad35 viruses containing the E3 region and an AdApt.Luc- or AdApt.LacZ-expression cassette were not stable. Apparently, in the newly described constructs, the deleted CMV promoter in front of pIX did not prevent the deletion of the transgene region. With the RSV promoter driving the pIX gene, however, we now are able to generate viruses of more than wild-type length. The Ad35.AdApt.Luc.rsv and Ad35.AdApt.LacZ.rsv are 35 kb and 36.5 kb, respectively (see also FIG. 2). Ad35.ΔE1AΔ21K.Luc (36.4 kb) also showed high transgene activity.

We next tested whether viruses would be intact after a plaque purification. Hereto, PER55K cells were seeded in 6-well plates at $0.9\times10^6$ cells/well and infected with different 10-fold dilutions of the Ad35.AdApt.LacZ crude lysates. Dilutions from $10^5$ to $10^8$ were plated and the next day an agar overlay was added. Hereto, cells were first washed with PBS and then 3 ml of a pre-warmed agar solution prepared by mixing 2×MEM (GibcoBRL; 9.14 ml), FBS (Gibco; 0.36 ml), MgCl (4.9 M; 0.037 ml) with agarose (SeaPlaque GTG; 2.5% in $H_2O$, 7.2 ml) was added. After solidification plates were further incubated at 37° C./5% $CO_2$. Four days later, plaques were visible and LacZ staining solution was added to the wells on top of the agar and allowed to drain. All viruses showed clear, separate plaques in the range of $10^7$ to $10^9$. In the case of the viruses with the RSV promoter driving the pIX gene, all plaques stained blue. In both cases where the deleted CMV promoter drives pIX, at least part of the plaques did not stain. This clearly shows that the packagable genome size/stability is increased in viruses that have the RSV promoter-regulating pIX.

This invention, for the first time, provides a stable recombinant adenovirus derived from or based upon an adenovirus serotype 35 lacking expression of a functional E1B gene.

Such an adenovirus has at least a deletion in the E1-region. In particular embodiments provided by the invention, the stable recombinant adenoviruses have foreign insert sequences of more than 4.2 kb and a packaged genome size of more than 33.4 kb, using methods according to the invention. It is, therefore, an object of the present invention to provide a stable recombinant adenovirus that: a) harbors a foreign nucleic acid sequence of more than 4.2 kb, and/or b) has a packaged genome size of more than 33.4 kb. In particular embodiments, the invention provides an Ad35- or Ad11-based recombinant adenovirus that: a) harbors a foreign nucleic acid sequence of at least 4.6 kb, and/or b) has a packaged genome size of more than 33.8 kb. Alternatively, or in addition thereto, the packaged genome sizes are at least 34.6, 35.0, 36.1 and 36.5 kb, respectively. The foreign sequences in these embodiments may include a heterologous promoter driving expression of pIX. In another aspect, the stable recombinant adenovirus is of serotype 11. A stable adenovirus, according to this aspect of the invention, can be passaged on a packaging cell to provide a batch of the recombinant adenoviruses with less than 10%, preferably less than 5%, and, preferably, none of the separate clones giving rise to deletions in the foreign sequences in the recombinant adenovirus as can be measured, e.g., by the PCR method exemplified in Example 3.

pBr.Ad35.ΔE1AΔ21K.Luc (see above) was made as follows. Construct pBr.Ad35.ΔE1AΔ21K (WO 02/40665) was digested with HpaI, dephosphorylated with CIP (New England Biolabs) and the 5 kb vector fragment was isolated from gel. Construct pBr.Ad35.ΔE1A.Luc was also digested with HpaI and the 3.3 kb insert was isolated from gel and ligated with the isolated vector fragment. Following transformation into competent STBL-2 cells (Invitrogen), a colony was selected with the insert in the correct orientation. This gave construct pBr.Ad35.ΔE1AΔ21K.Luc. pBr.Ad35.ΔE1A.Luc (also called pBr.Ad35.E1B+.Luc, because it still contains the E1B region) was made by inserting the AdApt.Luc cassette, taken from pAdApt.Luc after AvrII and BglII digestion and blunting with Klenow enzyme, into the vector fragment pBr.Ad35.leftITR-pIX (WO 02/40665) digested with SnaBI and HindIII and blunted with Klenow. Colonies with the expression cassette in the forward orientation were selected, giving pBr.Ad35.ΔE1A.Luc.

Example 10

Identification of pIX Regulatory Sequences

Figure 7:
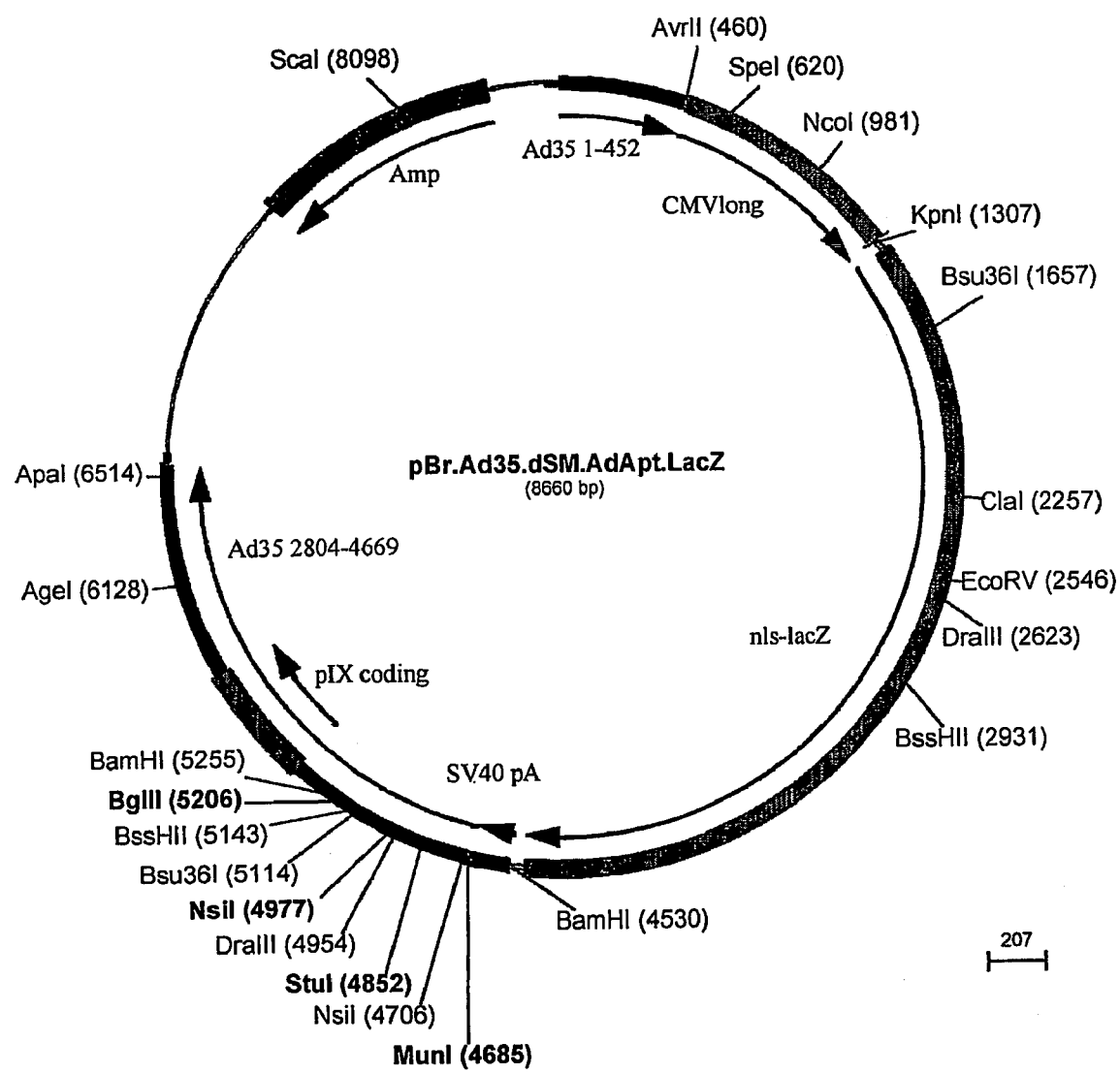
FIG. 7. Map of pBr.Ad35.ΔSM.AdApt.LacZ.

The previous examples show that Ad35-recombinant viruses in which the coding regions for E1A and E1B are completely removed become progressively more unstable if the genome size is increased. We show in this application that addition of a heterologous promoter driving pIX expression can overcome the instability. In WO 02/40665 and supra we disclosed that Ad35 viruses that retain the complete E1B-55K-coding sequence can be produced on PER.C6™ and are stable. The same is true for viruses that retain the full E1B-coding sequence (WO 00/70071; Abrahamsen et al., 1997). Together, these results raise the possibility that expression of the pIX gene is regulated differently in subgroup B viruses as compared to the pIX gene in subgroup C. Since the viruses that retain the E1B-55K gene driven by the E1B promoter are stable (see above), pIX regulatory sequences will probably be located in this region. To investigate this, we generated a series of constructs that retain different lengths of the 3' end of the 55K sequence. Hereto, pBr.Ad35ΔSM.AdAptLacZ is first generated as follows. Construct pBr.Ad35.1ITR-pIX (described in WO 00/70071) is digested with SnaBI and MfeI, blunted with Klenow and dephosphorylated with SAP enzyme (Roche). The 4.4 kb vector fragment is then isolated from agarose gel. Construct pAdApt.LacZ (an Ad5-based adapter plasmid pAdApt with LacZ transgene insert; WO 99/55132) is digested with AvrII and BglII (and, optionally, SalI to increase the difference in fragment size) and blunted with Klenow enzyme. The 4.2 kb CMV.LacZ.pA insert is then isolated from gel. Both isolated fragments are then ligated to give pBr.Ad35ΔSM.AdAptLacZ (FIG. 7). The orientation can be checked by restriction digestion since ligation in the correct orientation restores both the AvrII site and the MfeI site. Construct pBr.Ad35ΔSM.AdAptLacZ retains the 0.6 kb 3' E1B-55K sequences (wild-type Ad35 nucleotides 2804 to 3400) in the wild-type position relative to the pIX gene. Previously, we have shown that these 55K sequences do not lead to expression of a functional E1B-55K protein since propagation on PER.C6™ cells appeared impossible (pBr.Ad35ΔSM; WO 02/40665). Starting from pBr.Ad35ΔSM.AdAptLacZ, different deletions can be made of the 680 bp (0.7 kb) E1B-55K region by digestion with MfeI (isoschizomer of MunI) and either StuI, NsiI or BglII, followed by blunting of the protruding ends using Klenow or T4 DNA polymerase in the case of 5' or 3' overhang, respectively. Religation of the digested DNA gives functional adapter plasmids that are then used to generate recombinant viruses on PER55K cells by co-transfection with pWE.Ad35.pIX-rITR as described above. Additional constructs are made by using enzymes DraIII, Bsu36I, BssHII or BamHI, and digesting the vector partially (the LacZ gene also contains a recognition site for these enzymes) using methods known in the art, followed by selection of the correct clone. The stability is tested as described above for the Ad35.AdApt.LacZ.rsv construct. Constructs that are stable (i.e., do not acquire deletions in the transgene region) contain proper regulatory regions for pIX expression. In addition, it is possible to directly test promoter activity in a given sequence by inserting the sequence upstream of a reporter gene. pGL3basic (Promega) is such a reporter gene construct. The region between MunI and the start of the pIX gene was amplified using primer set Ad3555 KmfeF and Ad35pIXNcoR. This PCR (two minutes at 94° C.; then 30 cycles of [30 seconds at 94° C., 30 seconds at 59° C., 60 seconds at 72° C.]; followed by eight minutes at 68° C.; enzyme: Pwo (Genexis) according to the manufacturer's instructions, with additional 3% DMSO) amplified Ad35 sequences from 2804 to 3491 (numbering as in wild-type Ad35), thereby changing the sequence around the start codon of pIX into an NcoI site and introducing an HindIII site at the 5' end. This amplified fragment is digested with HindIII and NcoI and cloned into pGL3basic digested with the same enzymes generating pGL3-MN. pGL3-MN is then used to delete sequences upstream of the Luciferase-coding region by combining HindIII digestion with, e.g., PacI, NsiI, StuI, Bsu36I, BssHII or BglII, followed by blunting of the protruding ends and religation. Promoter activity is tested by transient transfection of the obtained constructs into PER.C6™ cells using lipofectamine reagent according to the manufacturer's instructions. Luciferase activity is analyzed two days after transfection using the Steady-Glo luciferase assay system (Promega) according to the manufacturer's instructions.

Alternatively, into the pGL3basic vector different regions are inserted, which regions are generated by PCR amplification using a 5'(forward) primer directed to a specific sequence in the Ad35-E1B-55K region and having a HindIII site attached at the 5' end combined with the Nco-pIXrev primer. In this way, one is not limited to the presence of a unique restriction site for cloning.

Figure 8:
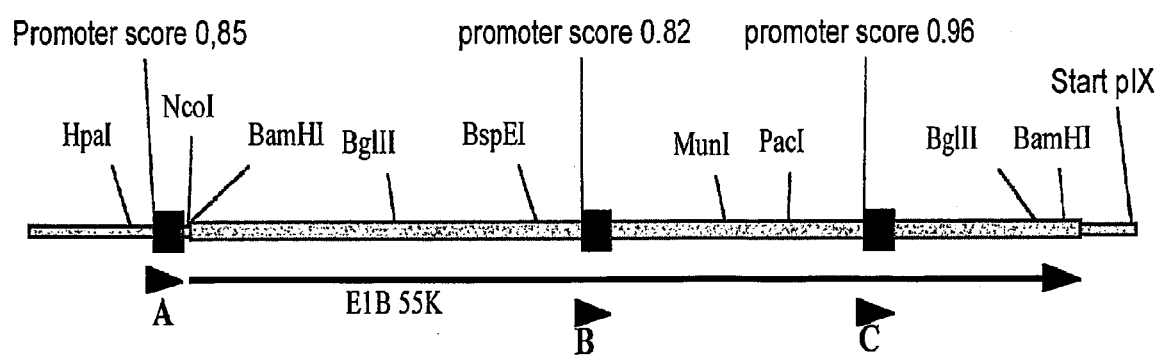
FIG. 8. Schematic representation of the putative promoters in the E1B promoter and 55K-coding region.

The location of the pIX promoter was further investigated by using software to find putative promoter sequences (Reese and Eeckman, 1995). FIG. 8 shows the promoter scores (minimum set at 0.65) for the E1B promoter directly linked to the 55K-coding sequence (as in pBr.Ad35.ΔE1AΔ21K). The regions marked A correspond to the E1B promoter and regions B and C are located within the 55K-coding region. The pIX upstream region is not recognized as a promoter sequence. Region C has the highest score (0.96) of the three (even higher than the known E1B promoter) and may, therefore, comprise sequences that influence pIX expression.

Figure 9:
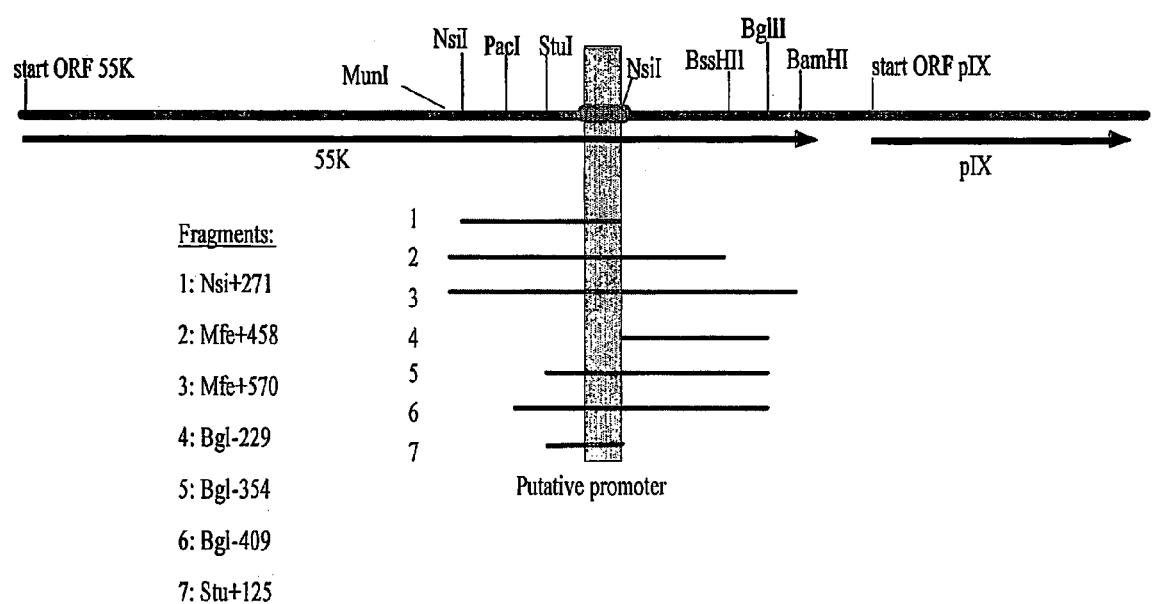
FIG. 9. Schematic representation of the restriction sites in the 55K region that can be used to generate distinct fragments for identification of a putative promoter. Numbering of the sites is according to their position in wild-type Ad35.

To locate and identify a possible pIX promoter experimentally, a series of small fragments corresponding to different (overlapping) parts of the 3'-end of the 55K-coding sequence are generated. FIG. 9 schematically depicts these fragments and their location relative to the putative promoter region and the pIX gene. The fragments are generated by restriction digestion using the indicated enzymes. Fragments are blunted with Klenow (5' protruding ends) or T4 DNA polymerase (3' protruding ends) and cloned into the NcoI site of the pGL3basic vector (Promega) also blunted by Klenow treatment and dephosphorylated by SAP treatment (Roche). Following transformation into competent bacteria, obtained plasmids are checked for the orientation of the insert by restriction digestion. Promoter activity is then analyzed by transient transfection of the obtained luciferase constructs into PER.C6™ cells using lipofectamine reagent according to the manufacturer's instructions. Empty pGL3basic plasmid serves as a negative control. Additional controls are made by cloning i) a BglII-MfeI fragment from pAdApt535 containing the Ad5-pIX promoter, ii) a 388 bp NruI-ApaLI RSV-promoter fragment (described above), or iii) the Ad35-pIX upstream region as a PCR fragment into the blunted NcoI site of pGL3basic as described above. The Ad35 upstream pIX region is amplified on pAdApt35IP1 using primers SV40-for and 5'-phosphorylated Ad35pIXrev. Following amplification, the DNA is digested with BglII and treated with Klenow.

Constructs are also transfected into human cells not containing adenovirus E1 (e.g., A549, Hela) to investigate the dependency on E1A expression.

The fragments are also cloned into an adapter plasmid pBr.Ad35ASM.AdAptLacZ (see above) to be able to generate recombinant viruses and study viral genome stability. Hereto, construct pBr.Ad35ΔSM.AdAptLacZ is digested with MfeI and BglII, blunted with Klenow enzyme and dephosphorylated. After gel isolation of the vector fragment, DNA can be ligated with the fragments described above (see FIG. 9) to give rise to a set of adapter plasmids that have varying lengths of 55K fragments upstream of the pIX gene. Viruses can be generated with the construct pWE.Ad35.pIX-rITR as described above. Control transfections are done with the pBr.Ad35ΔSM.AdAptLacZ, pAdApt35.LacZ and pAdApt35.LacZ.rsv constructs. Upon appearance of full CPE, cells and medium are harvested by one freeze/thaw cycle and used to re-infect fresh PER55K cells. Cells and medium are again harvested at full CPE and crude lysates are prepared and used to perform a plaque assay. After appearance of plaques, X-gal staining solution is added to check for LacZ expression.

The results of the above experiments aid in finding the position of pIx regulatory sequences in the Ad35-E1B-55K region.

As yet another alternative, pIX gene expression may be driven by the E1B promoter as a heterologous promoter for the generation of recombinant viruses. Hereto, pAdApt535.LacZ is digested with BglII and MfeI followed by Klenow treatment to blunt ends and dephosphorylation. The thus treated 4.8 kb vector fragment is then isolated from gel. The E1B-promoter region is isolated as a PCR fragment using pBr.Ad35.leftITR-pIX as target DNA and the Epr-F and Epr-R primers, whereby both primers are phosphorylated. PCR is done with Pwo DNA polymerase (Genaxis/Inno-train Diagnostik Gmbh) according to the manufacturer's instructions. The resulting 151 bp fragment is then cloned into the isolated vector to give pAdApt35Epr. LacZ This plasmid is then used to generate Ad35-based viruses and test stability as described before.

To identify the different transcripts that contain pIX sequences, RNA is isolated from infected cells and pIX-containing RNAs are identified by hybridization with a labeled specific probe. Hereto, PER55K cells are infected at a multiplicity of infection of 10 and 50 with the following viruses: wild-type Ad35, Ad35.E1B.AdApt.Luc, Ad35ΔE3.AdApt.Luc, Ad35ΔE3.AdApt535.Luc, Ad35.AdApt.Luc.rsv. Infected cells are harvested after eight hours (wild-type Ad35 also after two and 18 hours) and RNA is isolated using TRI-zol Reagent (Invitrogen). This RNA is size fractionated on an 1.5% agarose gel, transferred to a Northern blot and hybridized to a $^{32}$P-labeled probe derived from the pIX-coding region. Procedures are known in the art (described in Molecular Cloning: A laboratory manual, by Sambrook and Russell, 2001 or earlier versions). The length of the RNA can be determined if known RNA size markers are included and will give an indication of the RNA species that contain pIX sequences. To identify the mRNAs that start in the E1B promoter, the blot can be stripped and re-hybridized with a 5' 21K probe. pIX-containing transcripts that do not hybridize to the E1B-21K probe are likely generated by a promoter different from the E1B promoter.

Due to possible (and expected) splicing events, it is still difficult to precisely determine transcription start sites via this method. This can be achieved as follows. The isolated RNA is reverse transcribed into cDNA and the cDNA is used to specifically amplify 5' ends of pIX-containing RNAs using the GeneRacer System (Invitrogen) according to the manufacturer's instructions with the reverse primers directed to pIX-coding sequences: pIXrev and the nested primer pIXrev-N2. Cloning and sequencing of the amplified fragments gives the location of the transcription start sites and 5' sequences of mRNAs that contain pIX sequences. In this way, the possible pIX-coding mRNAs are identified. The correlation between the levels of pIX expression and stability of the corresponding recombinant adenoviruses can thus also be determined.

Example 11

E1B and pIX Sequences from Group B Adenoviruses

The above examples use the Ad35 virus as an example. Other members of the subgroup B that have considerable homology to each other could have comparable pIX regulation.

To investigate this, we aligned E1B and pIX sequences of subgroup B members. The sequence of Ad7 (SEQ. ID. NO.

57) is available via Genbank Accession number X03000. The sequence of Ad11 (SEQ. ID. NO. 56) was revealed by shotgun sequencing of DNA isolated from Ad11p wild-type viruses performed by Lark Technologies (UK), similar as described (WO 00/70071) for the Ad35 sequence (SEQ. ID. NO. 55). Ad11 and Ad35 are highly homologous to each other (overall 98.1% similarity) and the main differences are located in hexon and fiber knob.

The Ad11 sequence is also disclosed in WO 02/053759.

The sequence between the polyadenylation site (pA) of E1A and the pA downstream of the pIX gene is used in the alignment (FIG. 10). Ad35 has an overall similarity (in this region) of 98.4% to Ad11 and 82.9% to Ad7. This makes it very likely that pIX expression is regulated in the same way in these viruses.

Hence, the methods and means, according to the invention, as exemplified in the previous examples can be used accordingly to increase the stability and/or insert capacity of other recombinant adenoviruses of subgroup B, herein exemplified by Ad11 and Ad7.

Example 12

Generation of E1-Deleted Ad35 Viruses Expressing Ad5-E4/Orf6 on an Ad5-Complementing Cell Line The sequencing of the Adenovirus serotype 35 genome, as well as the construction of a plasmid-based vector system and generation of recombinant Ad35-based viruses, have been described in detail in WO 00/70071.

Figure 11:
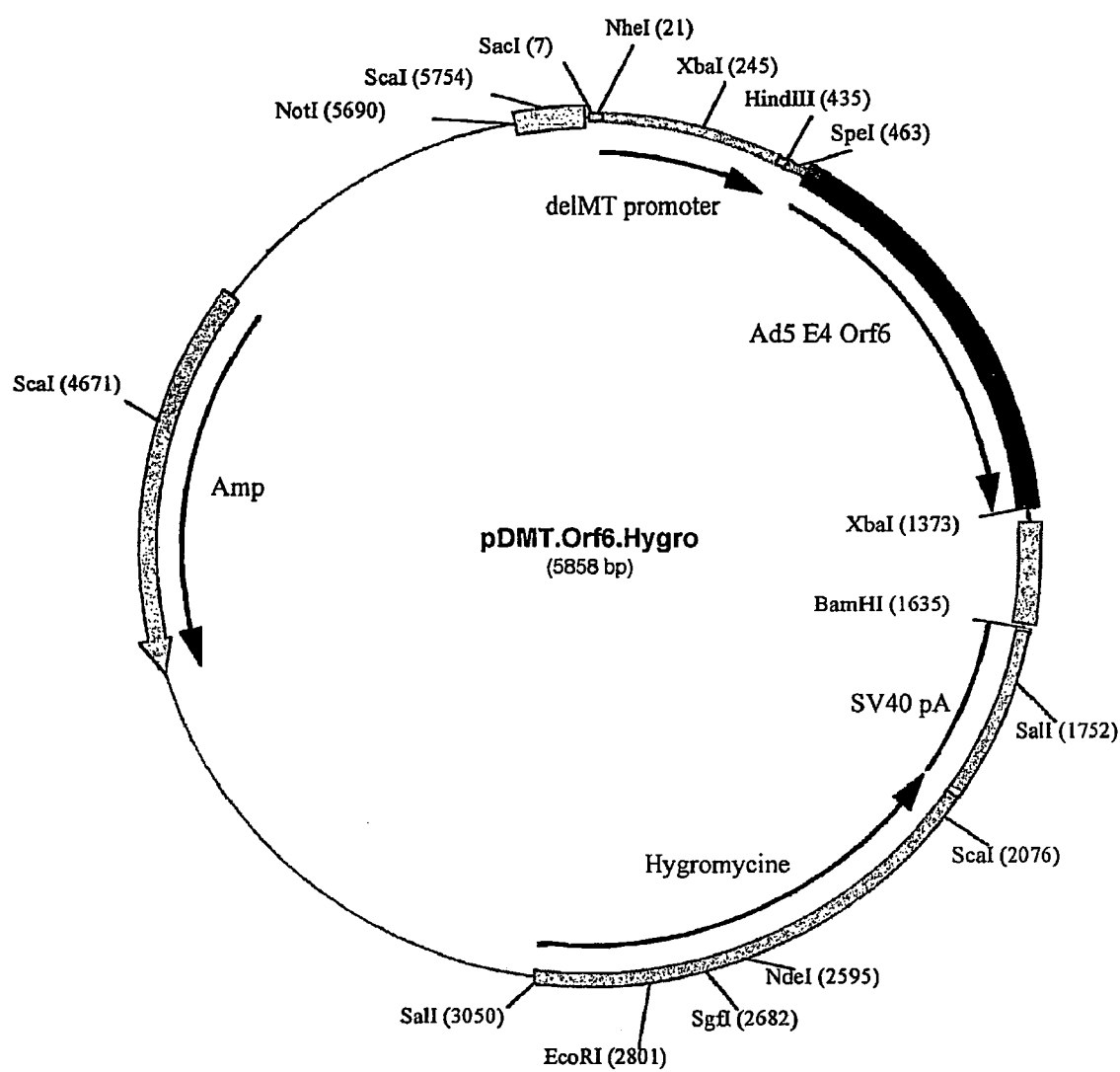
FIG. 11. Schematic representation of plasmid pΔMT.Orf6.Hygro (ECACC deposit no. P02041226).
Figure 12:
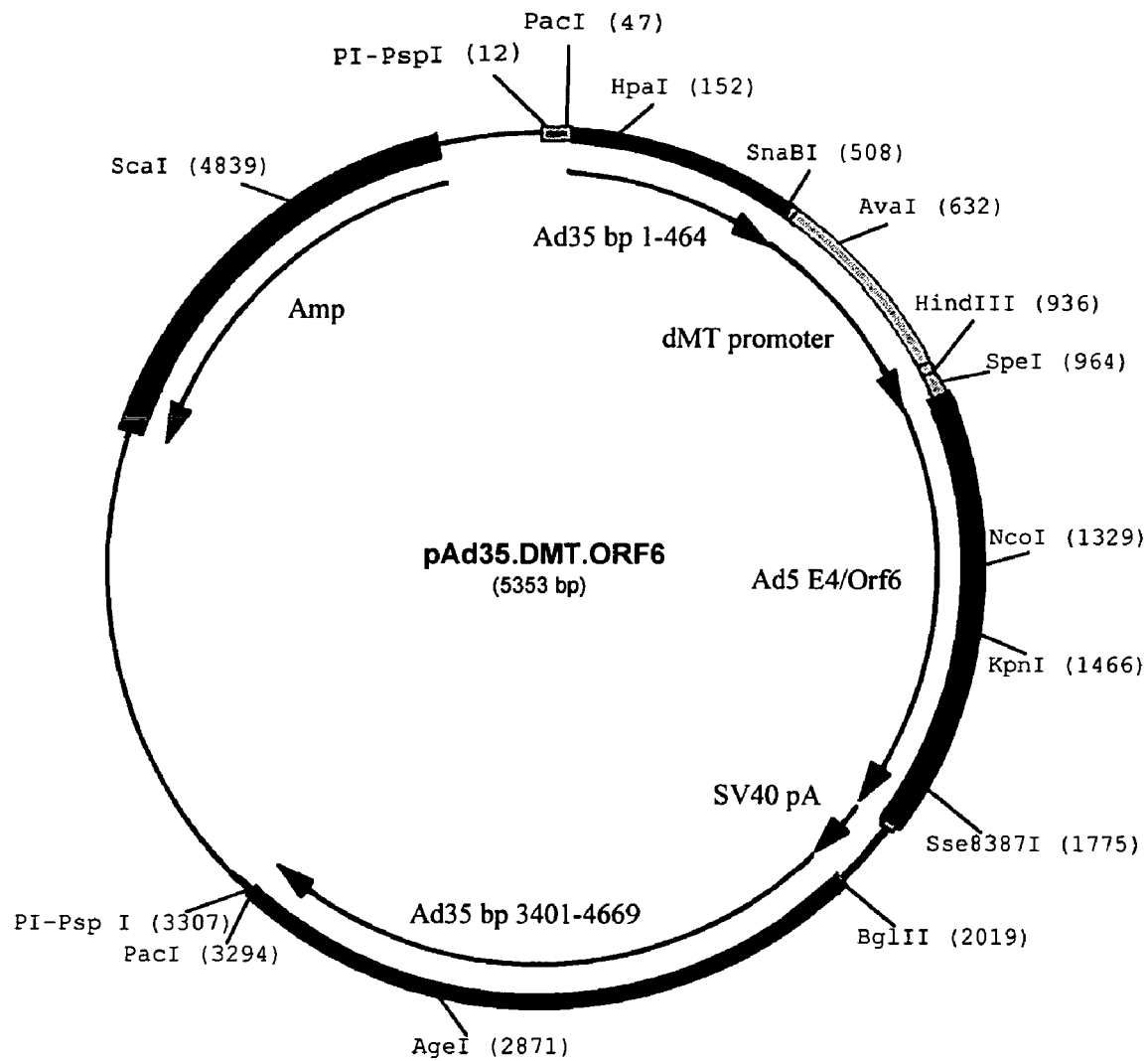
FIG. 12. Schematic representation of plasmid pAd35.ΔMT.Orf6.

The cloning of the Ad5-E4-orf6-coding sequence into pAdApt35IP1 (ECACC deposit no. P02041228; for cloning details of this plasmid, see WO 00/70071) was performed as follows. The plasmid was digested with NheI and AvrII and dephosphorylated with Calf Intestine Phosphatase (New England Biolabs). Digested DNA was isolated from gel using the GeneClean kit. Plasmid pΔMT.Orf6.Hygro (FIG. 11, ECACC deposit no. P02041226) was digested with NheI and subsequently partially digested with XbaI. After separation of the resulting bands on gel, the 1350 bp fragment corresponding to the ΔMT promoter linked to the E4-orf6 sequence was purified from gel. Next, both isolated fragments were ligated and transformed into electro-competent DH10B cells (Invitrogen/Life Technologies), after which a colony with the insert in the correct orientation with respect to the SV40 poly(A) signal was selected for large-scale DNA preparation. This resulted in construct pAd35.ΔMT.Orf6 (FIG. 12), which contains the Ad5-E4-orf6-coding sequence functionally linked to a mutated metallothionein promoter (ΔMT). The ΔMT promoter has been described by Hagmeyer et al. (1996). The Ad5-E4-orf6 sequence corresponds to nucleotide 33193 to nucleotide 34077 in the Ad5 sequence (Genbank accession number M73260). To test whether the expression of Ad5-E4-orf6 proteins would make production of fully E1-deleted Ad35 vectors possible on Ad5-complementing cells, pAd35.ΔMT.Orf6 was co-transfected with the Ad35 backbone construct pWE.Ad35.pIX-rITR onto PER.C6™ cells. Hereto, pAd35.ΔMT.Orf6 was digested with PI-Psp-1 and pWE.Ad35.pIX-rITR was digested with NotI to liberate the adenoviral inserts from the backbone. 2 μg of digested pAd35.ΔMT.Orf6 and 6 μg of digested pWE.Ad35.pIX-rITR were transfected using LipofectAmine. The transfection mixture was added to PER.C6™ cells that were seeded the day before at a density of $3.5 \times 10^6$ cells per T25 flask. The next day, the medium was changed for PER.C6™ culture medium (DMEM with 10% FBS and 10 mM $MgCl_2$) and cells were further incubated at 37° C./10% $CO_2$. Control transfections were performed with pAdApt35.Luc co-transfected with pWE.Ad35.pIX-rITR and pWE.Ad35.pIX-rITR alone. Two days after transfection, cells were passed from T25 to T80 flasks and incubated as described. Again three days later, the culture transfected with pAd35.ΔMT.Orf6, together with the Ad35 backbone, showed cytopathogenic effect (CPE) indicative of virus replication and was harvested (including cells and medium) after a further incubation of two days. The cell suspension was subjected to two rounds of freeze/thaw cycles and the resulting material (crude lysate) was kept at −20° C. until further use. The other flasks did not show CPE and were passed 1:3 in T80 flasks six days after transfer to T80. Again five days later, the pAdApt35.Luc+pWE.Ad35.pIX-rITR-transfected flask showed a few CPE-like events but this did not progress further. 0.2 and 0.5 ml of the crude lysate resulting from the pAd35.ΔMT.Orf6 transfection was used to re-infect PER.C6™ cells at approximately 85% confluency in T80 flasks. This resulted in full CPE after one day of incubation, indicating that infectious virus was present in the crude lysates. These cultures were also harvested by two freeze/thaw cycles. Additional control transfections with construct pAd35.ΔMT.Orf6 alone onto PER.C6™ were performed to confirm that orf6 expression by itself did not result in cell toxicity and CPE-like cell death. In conclusion, only the transfections with pAd35.ΔMT.Orf6, together with pWE.Ad35.pIX-rITR, did result in CPE and virus replication.

PCR analysis was performed to confirm the presence of Ad35-based viral genomes with Ad5-E4-orf6 replacing the former E1 region. Hereto, viral DNA was isolated from the crude lysate samples as follows. 275 μl of crude lysate material was incubated with 10 μl DNaseI (10 mg/ml) at 37° C. for 30 minutes. Subsequently, 6.0 μl 0.5 M EDTA (pH 8.0), 7.5 μl 20% SDS and 1.5 μl 20 mg/ml Proteinase K was added and mixed by vortexing. The mixture was then incubated at 50° C. for one hour. Finally, the viral DNA was isolated using the GeneClean Spin Kit (Bio 101, Inc.). Two μl of the isolated DNA was then PCR amplified using primers 35 psi-For and 35R4. The program was set at 94° C. for two minutes followed by 30 cycles at 94° C. for 30 seconds, 58° C. for 30 seconds and 72° C. for five minutes, and ended by an incubation at 72° C. for ten minutes. The primers are specific for Ad35 sequences and generate a fragment of 2.9 kb ranging from the packaging sequence to nucleotide 4669 (numbering as in wild-type Ad35 sequence), thus including the Ad5-orf6 transgene cassette. Electrophoresis of the obtained PCR fragments showed that the fragments had the expected length matching with the control PCR fragments generated on the adapter plasmid pAd35.ΔMT.Orf6. Thus, fully E1-deleted Ad35-based vectors can be made on Ad5-complementing cells if the virus also expresses Ad5-E4-orf6.

Example 13

Construction of pWE.Ad35.pIX-rITR5E4

Figure 14:
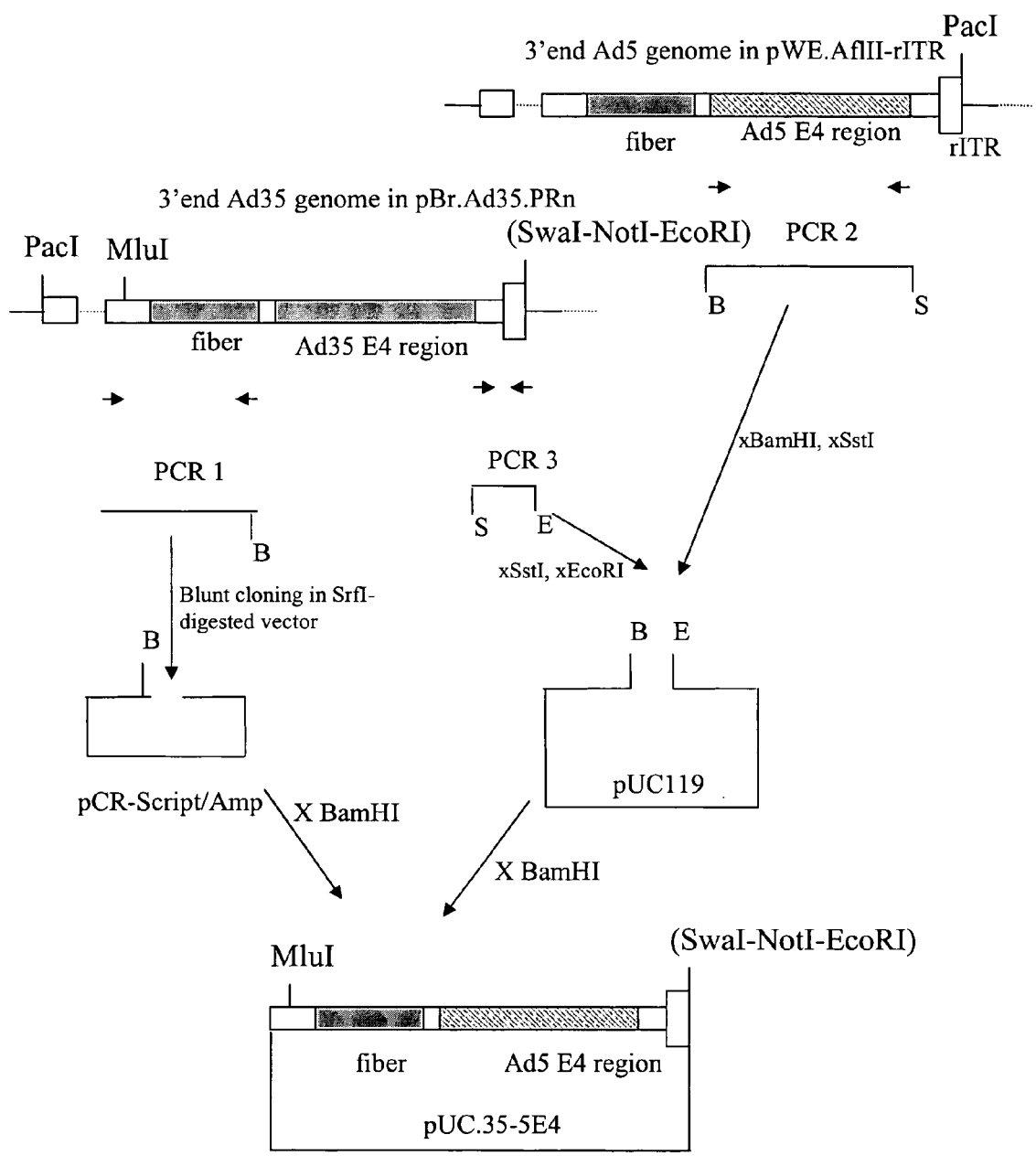
FIG. 14. Cloning steps leading to pUC.35-5E4.
Figure 16:
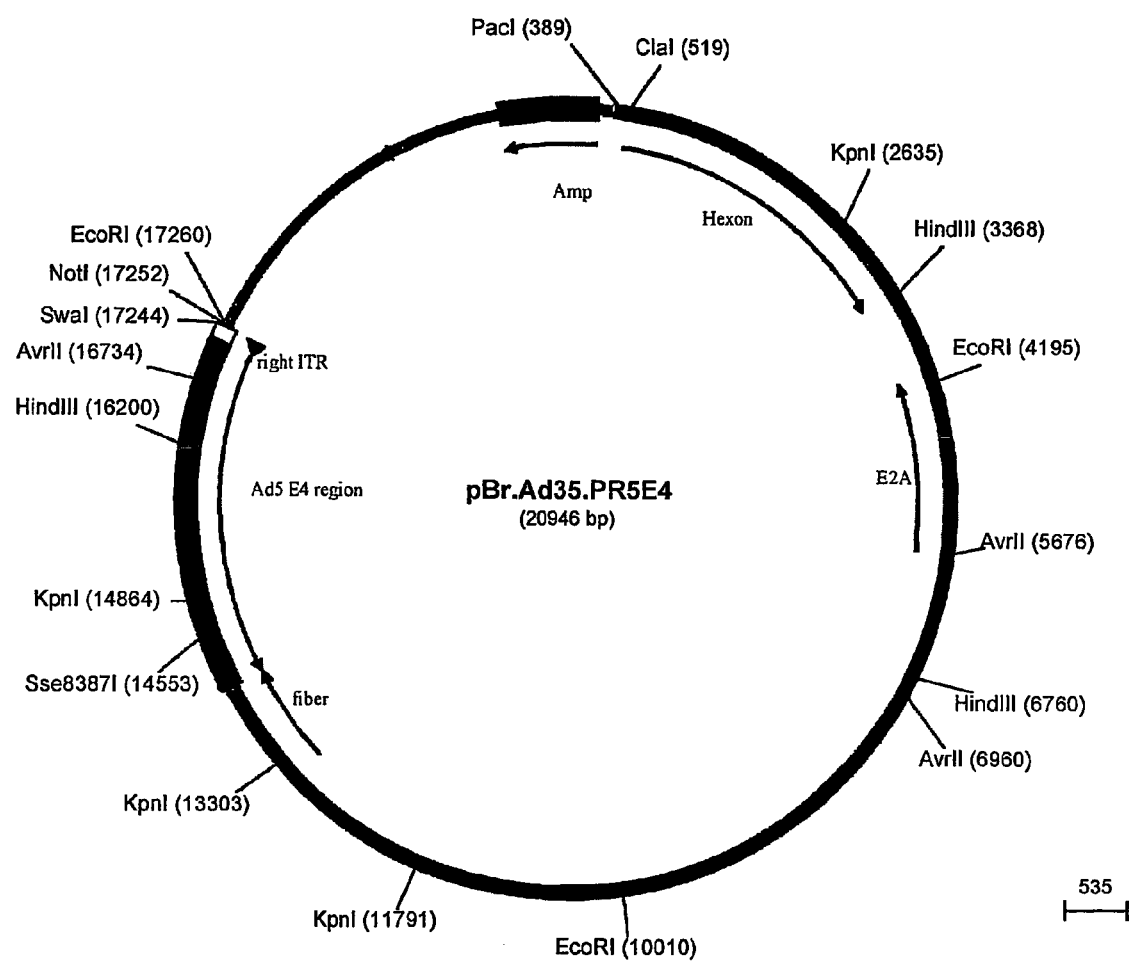
FIG. 16. Schematic representation of pBr.Ad35.PR5E4 (ECACC deposit no. P02041229).
Figure 17:
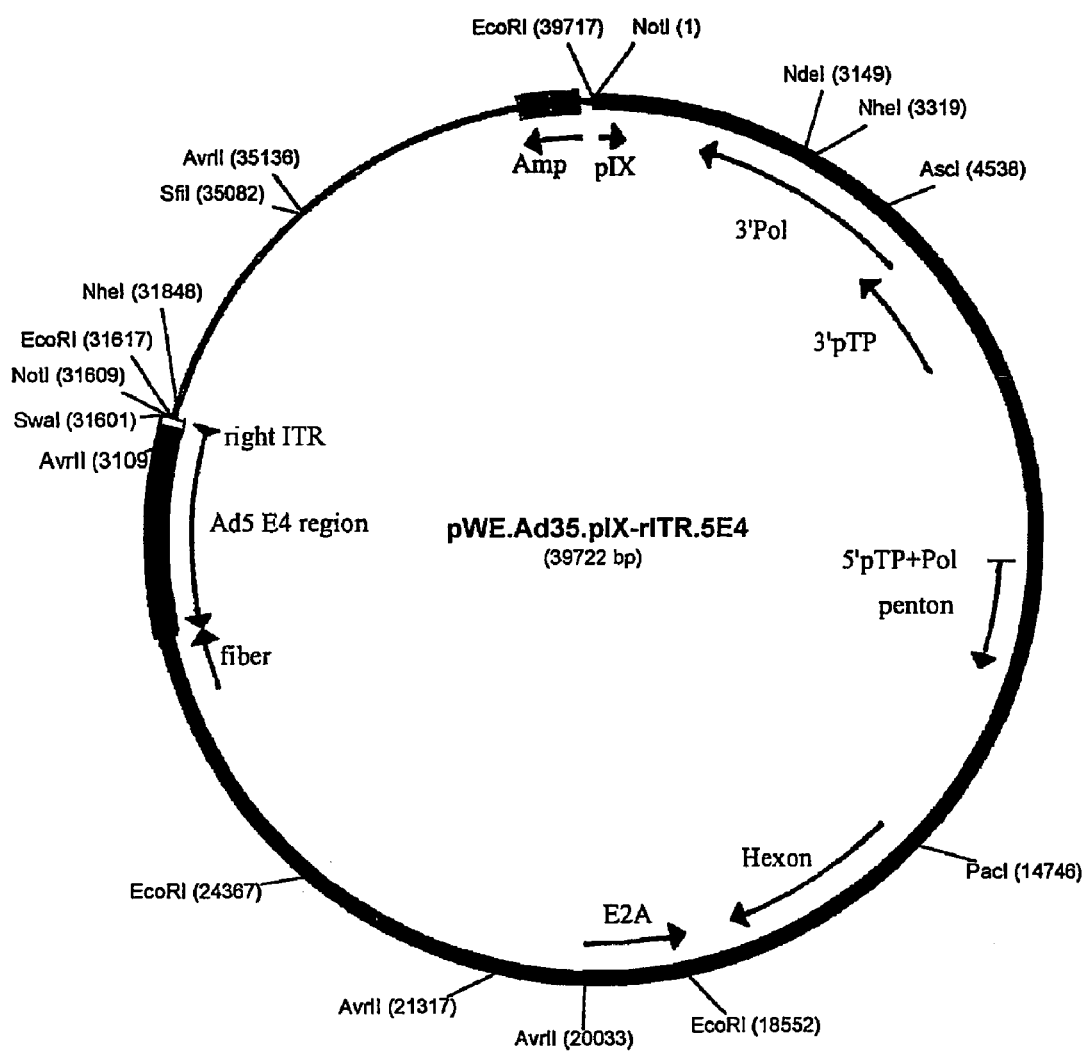
FIG. 17. Schematic representation of pWE.Ad35.pIX-rITR5E4.

A first PCR fragment was amplified using primers DF35-1 and 35FR. Amplification was done with pWE.Ad35.pIX-rITR (see WO 00/70071) as template DNA using Pwo DNA polymerase (Roche) with additional DMSO (Sigma, final concentration 3%). The program was as follows: 94° C. for two minutes followed by 30 cycles of (94° C. for 30 seconds, 52° C. for 30 seconds, 72° C. for three minutes) and a final step of 72° C. for eight minutes to ensure complete fragments. Amplification resulted in a 1.6 kb fragment corresponding to nucleotides 30224 to 31805 of the Ad35 sequence. A BamHI site was introduced at the 3' end. The amplified DNA was purified from gel using the GeneClean kit and ligated to the pCRScript/Amp cloning vector kit (Stratagene). Following transformation into electro-competent DH10B cells, white colonies were selected for further analysis. This resulted in construct pCR-fiber35. Due to the blunt cloning, the PCR fragment could be inserted in two orientations. A clone that had the insert with the BamHI site in the polylinker of the pCRScript/Amp vector at the 5' end was selected. Digestion with BamHI thus resulted in a 1.6 kb fragment. Sequencing confirmed correct amplification of the PCR fragment. A second PCR fragment was amplified using primers 5E4F and 5E4R. Amplification was done with pWE.Ad5.AflII-rITRsp, which is a cosmid vector containing an extra PacI site in pWE.Ad5.AflII-rITR (ECACC deposit no. P97082116 described in WO 02/40665). pWE.Ad5.AflII-rITRsp served as a template using Pwo DNA polymerase as described above, although pWE.Ad5.AflII-rITR could also be used for the same purpose. After purification from gel, the DNA was digested with SstI and BamHI (both sites introduced during the PCR) and the 3 kb fragment was purified from agarose gel using the GeneClean kit. The Ad5-E4 region that is amplified corresponds to bp 32794 to bp 35828 of the Ad5 sequence. A third PCR fragment was generated on pWE.Ad35.pIX-rITR using primers 3551TR and 3531TR. PCR amplification was performed as described above. The resulting 160 bp fragment is flanked by an SstI site (5' end) and an EcoRI site (3' end). After purification from gel as above, the DNA was digested with SstI and EcoRI. The 160 bp fragment corresponding to the right ITR of Ad35 was then separated from digested ends on a low melting-point agarose gel and collected in gel. Next, pUC119 was digested with BamHI and EcoRI and the 3.1 kb fragment was purified from gel using the GeneClean kit. The above-treated second and third PCR fragments were then ligated with BamHI/EcoRI-digested pUC 119 resulting in pUC.Ad5E4-351TR. The cloned PCR-derived inserts were sequenced to verify correct amplification. Next, the 1.6 kb insert in pCR-fiber35 was excised with BamHI and the fragment was purified from gel as above. pUC.Ad5E4-351TR was also digested with BamHI and the linear fragment was purified from gel. Ligation of both fragments and selection of the clones that had the correct orientation relative to each other resulted in pUC.35-5E4 (FIG. 14). The steps leading to the construction of pUC.35-5E4 are schematically represented in FIG. 13. The adenovirus insert in pUC.35-5E4 was sub-cloned into pBr.Ad35.PRn (FIG. 15; see WO 00/70071), a construct with Ad35 3' sequences. Hereto, construct pUC.35-5E4 is digested with MluI and NotI and the 4.7 kb fragment is purified from gel using the GeneClean kit. This fragment is then ligated with the vector fragment resulting from MuI and NotI digestion of construct pBr.Ad35.PRn. This 16.3 kb fragment was purified from gel using agarase enzyme (Roche). Ligations were then transformed into competent DH10B cells. The resulting construct was named pBr.Ad35.PR5E4 (FIG. 16, ECACC deposit no. PO$_{2041229}$). The last step entails cloning of the modified 3' end of the Ad35 sequence into the viral cosmid clone pWE.Ad35.pIX-rITR. Hereto, two fragments are combined in a lambda phage packaging reaction (Stratagene) according to the manufacturer's instructions. The first is the 16.8 kb modified Ad35 insert from pBr.Ad35.PR5E4 obtained by digestion with PacI and SwaI and the second is a 22.8 kb fragment obtained by digestion of pWE.Ad35.pIX-rITR with PacI and SwaI. The correct combination of the two fragments yields pWE.Ad35.pIX-rITR5E4 (FIG. 17). Thus, in this construct the E4 region in the Ad35 backbone is replaced with the corresponding region derived from Ad5.

Example 14

Construction of pWE.Ad35.pIX-rITR5Orf6

Figure 18:
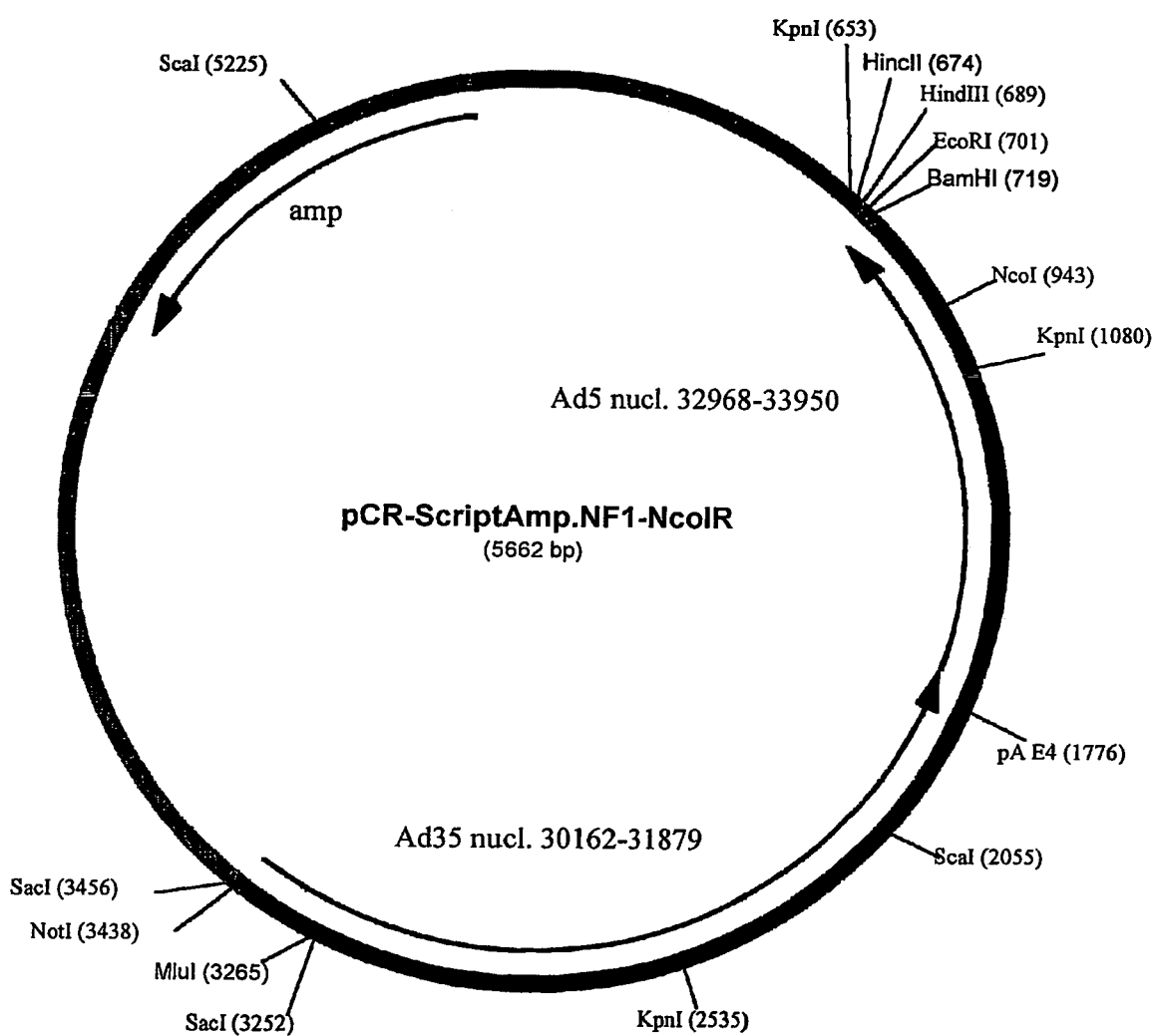
FIG. 18. Schematic representation of pCR-scriptAmp.NF1-NcoIR.
Figure 19:
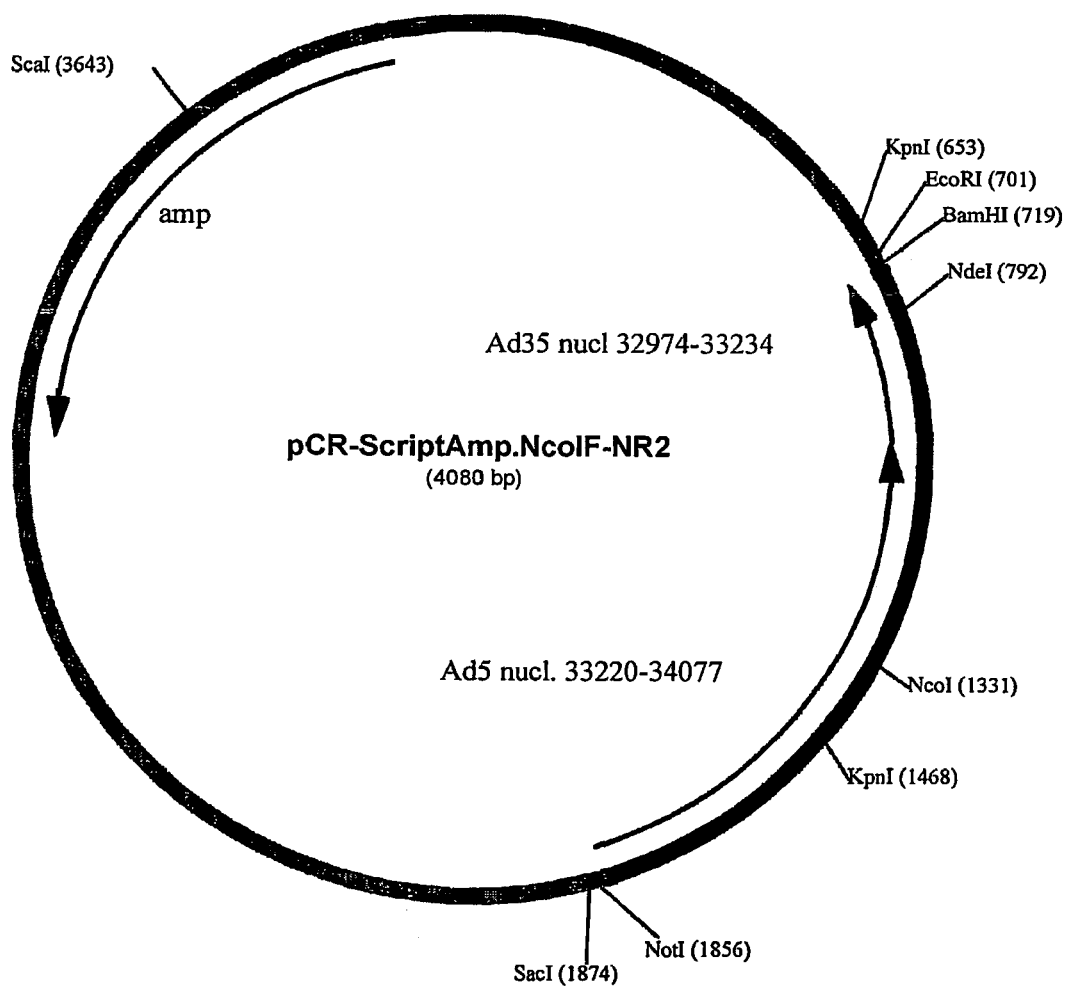
FIG. 19. Schematic representation of pCRscriptAmp.N-coIF-NR2.
Figure 20:
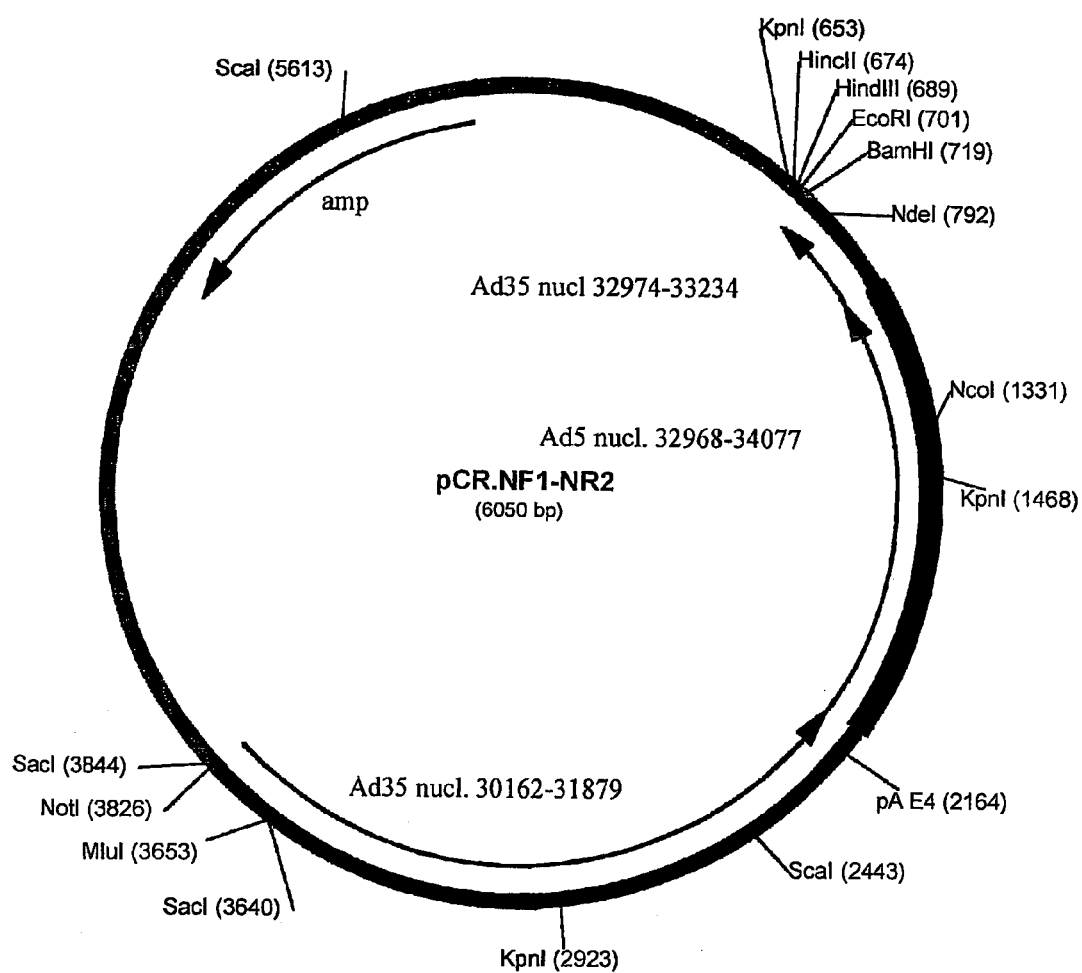
FIG. 20. Schematic representation of pCR.NF1-NR2.

To obtain an adenoviral backbone construct that contains the Ad35 sequences from the pIX gene (nucleotide 3401 in the Ad35 sequence) to the end of the right ITR but with the sequences for E4-orf6 and -orf6/7 exchanged for the corresponding sequences of Ad5, Ad35 and Ad5 sequences were PCR amplified and combined as described below. PCR fragments were generated with Pwo DNA polymerase with the addition of DMSO up to 3%. The first PCR was done with pBr.Ad35.PRn (FIG. 15; see WO 00/70071) as template and the primers E4-F1 and E4-R2. The program was set as follows: 94° C. for two minutes, five cycles of (94° C. for 30 seconds, 50° C. for 30 seconds and 72° C. for one minute) followed by 30 cycles of (94° C. for 30 seconds, 60° C. for 30 seconds and 72° C. for one minute) and ended with a final step at 68° C. for eight minutes. The resulting 1.8 kb fragment was purified using the GeneClean kit. The second PCR was done with pWE.Ad5.AflII-rITRsp, which is a cosmid vector containing a PacI site in pWE.Ad5.AflII-rITR (ECACC deposit no. P97082116, described in WO 02/40665), as template and the primers E4-F3 and E4-R4. The program was set as follows: 94° C. for two minutes followed by 30 cycles of (94° C. for 30 seconds, 62° C. for 30 seconds and 72° C. for one minute) and ended with a final step at 68° C. for eight minutes. The 1.1 kb fragment was purified as above. The third PCR was done with pBr.Ad35.PRn as template and the primers E4-F5 and E4-R6. The program was set as follows: 94° C. for two minutes, five cycles of (94° C. for 30 seconds, 48° C. for 30 seconds and 72° C. for 45 seconds) followed by 30 cycles of (94° C. for 30 seconds, 56° C. for 30 seconds and 72° C. for 45 seconds) and ended with a final step at 68° C. for eight minutes. The 366 bp fragment was purified as above. Samples of the purified fragments were loaded on a gel to estimate the concentration and then the fragments were mixed together to contain 700 ng PCR-1, 650 ng PCR-2 and 430 ng PCR-3 in a total of 30 μl. To this mixture, 3 μL EcoPol buffer (New England Biolabs), 3 μl 2 mM dNTP solution and 3 μl milliQ H$_2$O was added. The resulting mixture was incubated at 94° C. for three minutes and then cooled down to 65° C. in a PCR machine at a rate of 0.5° C./second. Following incubation at 65° C. for ten minutes, the mixture was further cooled down to 20° C. at a rate of 0.05° C. per second and incubated for ten minutes at 20° C. Then, 1 μl (5 units) Klenow enzyme (New England Biolabs) was added followed by an incubation of 60 minutes at 37° C. 5 μl of this Klenow mixture was used as a template to separately amplify two fragments as follows. Primer set 1: NF-1 and NcoI-R was used in a reaction using Pwo DNA polymerase (Roche) with the addition of DMSO to a final concentration of 3% and using the following settings of the PCR machine: 94° C. for two minutes followed by 30 cycles of (94° C. for 30 seconds, 66° C. for 30 seconds and 72° C. for three minutes) followed by a final incubation at 68° C. for eight minutes. Primer set 2: NcoI-F and NR-2 was used in a reaction using Pwo DNA polymerase (Roche) with the addition of DMSO to a final concentration of 3% and using the following settings of the PCR machine: 94° C. for two minutes followed by 30 cycles of (94° C. for 30 seconds, 62° C. for 30 seconds and 72° C. for 90 seconds) followed by a final incubation at 68° C. for eight minutes. The resulting fragments of 2.7 kb (primer set 1) and 1.1 kb (primer set 2) were purified from gel using the GeneClean kit and each was ligated to the pCRscriptAmp vector (Stratagene) and transformed into DH10B electro-competent cells. This resulted in construct pCRscriptAmp.NFI-NcoIR (FIG. 18) and construct pCRscriptAmp.NcoIF-NR2 (FIG. 19). Since the inserts contained blunt ends, two orientations were obtained of each cloning. Using KpnI digestions, the constructs with the orientation needed for further cloning were selected (see FIGS. 18 and 19). The inserts were then sequenced to verify correct amplification. Next, part of the insert from pCRscriptAmp-NcoIF-NR2 was excised using BamHI and NcoI and purified from gel as above. pCRscriptAmp-NFI-NcoIR was digested with the same enzymes and the vector-containing fragment was also purified from gel. Ligation of these fragments resulted in pCR.NF1-NR2 (FIG. 20). pCR.NF1-NR2 contains Ad35 sequences between nucleotides 30162 and 33234 of the Ad35 sequence with E4-orf6 and E4-orf6/7 sequences between nucleotides 31879 and 32974 replaced for Ad5-derived sequences located between 32968 and 34077 from the published Ad5 sequence in Genbank (Accession Number M73260). Thus, as can be seen in the amino acid alignments presented in FIGS. 21 and 22, the amino acid sequence of the cloned E4-orf6 protein is identical to the E4-orf6 sequence found in Ad5 (SEQ. ID. NO. 61; amino acid sequence of E4-orf6 of Ad35 is SEQ. ID. NO. 62) and the E4-orf6/7 amino acid sequence is, for the greater part, identical to the E4-orf6/7 sequence present in Ad5 (E4-orf6/7 sequence is given for Ad5 as SEQ. ID. NO. 63, for Ad35 as SEQ. ID. NO. 64, for the cloned fusion protein as SEQ. ID. NO. 65). Obviously, different hybrid Ad35-Ad5-E4 constructs can be designed using the general method outlined above without departing from the invention. This chimeric insert from pCR.NF1-NR2 was then cloned into pWE.Ad35.pIX-rITR: pCR.NF1-NR-2 was digested with MluI and NdeI and the resulting 2.8 kb fragment was purified from gel using the GeneClean kit. Construct pBr.Ad35.PRn was also digested with MluI and NdeI and the 18 kb vector fragment was isolated from gel using agarase enzyme (Roche). Ligation of both fragments resulted in construct pBr.Ad35.PR.5Orf6 (FIG. 23, ECACC deposit no. P02041227). The Ad35 sequences between PacI and SwaI containing the chimeric E4 region in this construct are then cloned into construct pWE.Ad35.pIX-rITR using lambda-phage packaging as described above. The resulting pWE.Ad35pIX-rITR.5Orf6 (FIG. 24) is then used to generate recombinant Ad35-based viruses by co-transfection on PER.C6™ packaging cells with an Ad35 adapter plasmid.

Example 15

Construction of pWE.Ad35.pIX-rITRΔE3.5E4 and pWE.Ad35.pIX-rITRΔE35Orf6

The Ad35 backbone was further modified by a deletion of E3 sequences. E3 proteins are known to modulate the host immune response to adenovirus infection and are, therefore, not necessary for in vitro propagation of recombinant viruses. Furthermore, the deletion of E3 sequences allows for insertion of larger heterologous sequences in the vectors without compromising the packaging efficiency. Also, for the application of adenoviral vectors as vaccination vehicles, expression of immunomodulatory genes encoded by the E3 region is not preferred.

The construction of pWE.Ad35.pIX-rITRΔE3 (FIG. 1) was described supra. To construct the E3-deleted versions of the E4-modified backbone constructs described above, the E4 modifications were introduced into the pBr.Ad35.PRnΔE3 (FIG. 25) construct as follows. Construct pUC.35-5E4 (FIG. 13) was digested with MluI and NotI and the 4.7 kb fragment was isolated from gel using the GeneClean II kit. Construct pBr.Ad35.PRnΔE3 was also digested with MluI and NotI and the 13.6 kb vector fragment was isolated from gel using the GeneClean spin kit. Ligation of these fragments resulted in construct pBr.Ad35.ΔE3.PR5E4 (FIG. 26). Construct pCR.NF1-NR2 (FIG. 20) was digested with MluI, NdeI and BglI (the latter to digest the vector fragment into smaller fragments) and the 2.8 kb fragment was isolated from gel using the GeneClean spin kit. Construct pBr.Ad35.PRnΔE3 was digested with MluI and NdeI, dephosphorylated using CIP enzyme (New England Biolabs) and the 15.2 kb vector fragment was also isolated using the GeneClean spin kit. Ligation of these fragments gave construct pBr.Ad35.ΔE3.PR5Orf6 (FIG. 27).

pBr.Ad35.ΔE3.PR5E4 and pBr.Ad35.ΔE3.PR5Orf6 are then used to swap the 3' PacI-SwaI fragment in pWE.Ad35.pIX-rITR for the corresponding regions from pBr.Ad35.ΔE3.PR5E4 and pBr.Ad35.ΔE3.PR5Orf6 as described intra. This leads to constructs pWE.Ad35.pIX-rITRΔE3.5E4 and pWE.Ad35.pIX-rITRΔE3.5Orf6. An alternative method to generate these large cosmids is to use three fragments in the ligation reaction for packaging: a 14.7 kb NotI-PacI fragment from pWE.Ad35.pIX-rITR, the PacI-NotI insert from pBr.Ad35.ΔE3.PR5E4 or pBr.Ad35.ΔE3.PR5Orf6 and the NotI digested pWE15 cosmid vector fragment (Stratagene). This latter fragment can also be isolated from the NotI/PacI digestion of pWE.Ad35.pIX-rITR.

Co-transfection of, e.g., the NotI-digested pWE.Ad35.pIX-rITRΔE3.5Orf6 with, e.g., PI-PspI-digested pAdApt35.LacZ.rsv (Example 9) into PER.C6™ cells will generate recombinant adenovirus derived from Ad35, which recombinant adenovirus comprises E4-orf6 derived from Ad5 (conferring the ability of propagation on PER.C6™), the recombinant adenovirus furthermore having a heterologous pIX promoter resulting in increased pIX-expression levels and stable virions.

Example 16

Generation of E1- and E1/E3-deleted Ad35-based vectors on PER.C6™ cells

To enable generation of recombinant Ad35 viruses on the complementing cell line PER.C6™ using the pBr.Ad35.PRn-based constructs, we first made a new construct containing Ad35 sequences from bp 3401 to bp 24650 of the Ad35 sequence (WO 00/70071) and thus overlaps with both the adapter plasmids and the pBr.Ad35.PRn-based constructs. Transfection of these three plasmids into PER.C6™ cells and a double-homologous recombination event leads to a complete viral genome and replication of recombinant viruses as outlined in FIG. 18. The required plasmid was made by deletion of a large part of the Ad35 sequences in pWE.Ad35.pIX-rITR. Hereto, pWE.Ad35.pIX-rITR was digested with EcoRV and the 29 kb vector-containing fragment was purified from a low melting-point gel using the GeneClean spin kit. The purified DNA was self-ligated and used to transform DH10B electro-competent bacteria (Invitrogen/LTI) resulting in pWE.Ad35.pIX-EcoRV (FIG. 29).

All DNAs used for transfection were digested as indicated in Table V, heat-inactivated at 65° C. for 15 minutes and used without further treatment in the transfection. PER.C6™ cells were seeded the day prior to transfection in T25 flasks at a density of $3 \times 10^6$ cells/flask and transfected as indicated in Table V using LipofectAmine (Invitrogen/LTI) according to the manufacturer's instructions, except that the transfection mixture in serum-free DMEM medium (Gibco/BRL) was replaced for PER.C6™ culture medium (DMEM, 10% FBS and 10 mM $MgCl_2$) after five hours. The day after, transfection efficiency was estimated at 50% by fluorescence microscopy. Two days later, cells were trypsinized and reseeded in T80 flasks and further incubated at 37° C./10% $CO_2$. Six days following transfection, all cultures showed full cytopathogenic effect (CPE, indicative for virus propagation) except for the PER.C6™ culture transfected with Ad35.AdApt.eGFP+pWE.Ad35.pIX-rITR. One day later, cells and medium in the flasks with CPE were harvested and subjected to two freeze/thaw cycles, clarified from cell debris by centrifugation (ten minutes at 1500 rpm) and 100 µl of these crude lysates were used to re-infect fresh PER.C6™ cells at 85% confluency in T80 flasks. The transfection of Ad35.AdApt.eGFP+pWE.Ad35.pIX-rITR that did not show signs of CPE was harvested by trypsinization and also treated as above. Two days following infection of fresh PER.C6™ cells, all flasks showed full CPE except for the one that showed no signs of CPE at the time of initial harvesting. This clearly shows that fully E1-deleted Ad35-based viruses can be made on PER.C6™ cells when the Ad5-E4-orf6 gene product is expressed from the Ad35 backbone.

Example 17

E1-Deleted Ad35 Viruses with a Heterologous Promoter Driving pIX Expression

To investigate the effect of a heterologous-promoter sequence activating the pIX gene in full E1-deleted viruses, a series of adapter plasmids was used to generate recombinant Ad35 viruses. Hereto, pAdApt35LacZ, pAdApt35.LacZ.rsv (Example 9), pAdApt535.LacZ (Example 5) and pAdApt35BLacZ (containing the Ad35-E1B-promoter sequence in front of the pIX gene, described below) were digested with pIPsp-1 and used to generate viruses with NotI-digested cosmid pWE/Ad35-3481 and pWE/Ad35-3481ΔE3 (Example 7) as described in Example 2 (and in WO 00/70071). In addition, viruses were generated with adapter plasmid pBr.Ad35ΔSM.AdAptLacZ (FIG. 7; Example 10). This adapter plasmid is deleted for E1A and a large part of the E1B sequences. It retains 0.6 kb of the 3' E1B-55K sequence and also has wild-type sequences between the stop codon of 55K and the start codon of pIX.

Upon full CPE, the cells and medium were harvested, freeze/thawed and centrifuged to remove the cell debris. The supernatant (cleared lysates) of each of the transfections was then used to perform a plaque assay as described in Example 9. Cleared lysates were diluted serially ten-fold and $10^{-5}$ to $10^{-9}$ dilutions were plated.

One week after addition of the agar overlay, plaques became visible and were stained with X-gal to monitor LacZ activity. Table VI summarizes the results of these experiments. All Ad35 viruses having additional or other sequences than just the endogenous proximal pIX upstream sequence regulating pIX perform better and have a higher number of expressing plaques in our assay as compared to the E1-deleted Ad35.AdApt.LacZ viruses. Note that the total genome length of the Ad35ΔSM.LacZ viruses (106% compared to wild-type Ad35) exceeds the maximum packagable length as determined for Ad5 viruses (105%). This may influence the results obtained for this virus. The Ad35.AdApt.LacZ.rsv (105%) is also at the border of the theoretical packagable size. Altogether, the results show that a heterologous promoter driving pIX expression improves the maximum tolerated packaging size and the stability of E1-deleted Ad35 viruses. The same is true for viruses that have a longer endogenous proximal sequence (Ad35ΔSM.LacZ), suggesting that the additional (E1B-55K) sequences herein contain regulatory elements for pIX expression.

pAdapt35BLacZ is an Ad35 adapter plasmid with the Ad35-E1B-promoter sequence regulating the pIX gene.

Adapter plasmid pAdApt35BLacZ was generated as follows:

The E1B-promoter fragment was amplified using the primers 35E1Blong and Ad35E1bpromrev. Both primers were phosphorylated. The reaction was done with Pwo DNA polymerase (Inno-train, Diagnostic GmbH) according to the manufacturer's instructions. pBr.Ad35.leftITR-pIX was used as template DNA (25 ng, described in WO 02/40665). The program was set as follows: two minutes at 94° C. and then 30 cycles of (94° C. for 30 seconds, 60° C. for 30 seconds and 72° C. for one minute) and ended by ten minutes at 72° C. The cooling/heating slope was set at 2° C./second. This PCR results in amplification of the potential E1B promoter of Ad35 of 125 nucleotides. Construct pAdapt535.LacZ (Example 5) was then digested with MfeI and BglII. After digestion, the vector was treated with Klenow enzyme to create blunt ends. A dephosphorylation step was done using SAP (Roche). The thus treated 8 kb vector fragment was then isolated from gel. The E1B-promoter region was also isolated from gel. These two fragments were ligated and transformed into DH5a-Tlr-competent cells (Invitrogen). The correct orientation of the E1B promoter in the resulting plasmid was confirmed by digesting with HpaI and ApaLI. After selection of the correct clone, the inserted E1 B-promoter sequence was also verified by sequencing.

Example 18

The Promoter of the pIX Gene is Located in the 3' end of the E1B-55K-Coding Sequence in Ad35 and Ad11 Viruses Based on the results described supra, we expected that the pIX promoter in subgroup B viruses would be located in the E1B-55K-coding region. To investigate this directly, we set out to identify the pIX mRNA cap site as described in Example 10. Hereto, wild-type Ad35, wild-type Ad11 and Ad35.E1B+.AdApt.Luc viruses were used to infect PER55K clone 16 cells at an MOI of 50 VP/cell. As a control, wild-type Ad5 was taken along since the promoter and mRNA start site of this virus is known. RNA was isolated from the infected cultures at 16-18 hours post-infection using TRIzol agent (Invitrogen) as described by the manufacturer. At the end of the procedure, the isolated RNA was stored in 100% formamide. The GeneRacer Kit (Invitrogen) was used to amplify the 5' end of pIX transcripts in order to locate the start of transcription. Before starting GeneRacer protocol, 5 µg RNA was purified from the formamide by sodium acetate precipitation as described in the GeneRacer protocol. Purified RNA was treated according to manufacturer's protocol for amplification of the 5' end of the pIX mRNA. After phosphatase treatment and subsequent removal of the cap structure with tobacco acid pyrophosphatase and ligation of the GeneRacer RNA oligo, SuperScript™ II Reverse Transcriptase from the kit was used for cDNA synthesis. cDNA was synthesized by reverse transcription using a gene-specific (reverse) primer for pIX. For Ad35 (wild-type and E1B+.Luc virus) and wild-type Ad11 primer, pIXrev was used. For Ad5, the primer pIXrev-Ad5 was used. The resulting cDNA (1 µl of unknown concentration) was used as a template for PCR to generate dsDNA. This PCR was done using Pwo DNA polymerase (Roche) according to the manufacturer's instructions and with the addition of DMSO (Sigma; 3% v/v). The amplification was done with the GeneRacer 5' primer from the kit which is specific for the oligonucleotide ligated to the 5' end of the mRNA and the gene-specific reverse primers, as mentioned above. Reaction conditions were as follows: denaturation at 94° C. for two minutes, followed by 30 cycles of (94° C. for 30 seconds, 60° C. for 30 seconds, 72° C. for two minutes) and finished by elongation at 68° C. for eight minutes. The resulting DNA fragments were size separated by electrophoresis on a 1.0% agarose gel. For Ad5, a 480 bp fragment was obtained and for Ad35 (both viruses) and Ad11, a 200 bp fragment was obtained. Ad11 also showed a 2 kb fragment. All fragments were excised and purified from agarose gel. The purified DNA fragments were cloned into the pCR4Blunt-TOPO® vector (Invitrogen). The vectors were sequenced using commercial M13 Forward and Reverse primers. The resulting sequences were aligned against wild-type sequences to locate the start of pIX transcription. The 200 bp band isolated from Ad35 and Ad11 cDNA preparations constituted the genuine pIX mRNA. The 2 kb fragment isolated from Ad11 turned out to originate from the E1 B promoter. FIG. 30 shows an alignment of the Ad35 (SEQ. ID. NO. 59) and Ad11 (SEQ. ID. NO. 58) cDNA sequences with the wild-type Ad35 sequence (SEQ. ID. NO. 60). The alignment reveals the location of a spliced intron sequence in the pIX mRNA. In FIG. 31, the locations of the identified cap site and splice sites are schematically shown in the E1B-pIX region of Ad35. For Ad5, the expected pIX mRNA (Babiss and Vales, 1991) was identified with the cap site located at position 3580 (not shown; numbering as in Genbank accession no. M73260). For Ad35, the cap site was located in the 3' end of the E1B-55K gene at position 3339 on an A residue (Ad35 sequence WO 00/70071). In Ad11, the cap site was similarly found on a T residue (position 3339 in Genbank Acc No. AY163756). Interestingly, the sequence between the stop codon of the 55K gene and the start codon of the pIX, where, in Ad5 viruses, the promoter for pIx is located, is spliced out of the mRNA in Ad35 and Ad11 viruses. These results provide strong evidence that in Ad35 and Ad11, pIX gene expression is regulated from a promoter located in the 3' end of the 55K gene.

Example 19

E1-Deleted Ad35 Viruses that Retain a Short Stretch of 3' E1B-55K Sequence Have a Larger Packaging Capacity With the identification of the pIX mRNA cap site it becomes possible to include the natural Ad35 promoter for correct pIX expression and also limit, as much as possible, the E1B-55K sequences in the viral vector. Here, we show, as a non-limiting example, the construction of an Ad35 adapter plasmid that retains 166 bp of the 3' end of the 55K-coding sequence (pAdApt35Bsu.Luc) and the generation of an E1-deleted Ad35Luc virus with increased stability and/or packaging capacity. This 166 bp sequence does not code a functional 55K gene product but contains the pIX mRNA cap site identified in the previous example in its natural position relative to the pIX-coding sequence.

Construct pAdApt35Bsu.Luc was generated as follows:

First, a PCR fragment was generated using 40 ng pBr.Ad35.leftITR-pIX as target DNA (described in WO 02/40665) and primers Bsu55KF and Age-pIXR. The PCR was performed with Pwo DNA polymerase (Genaxis) according to the manufacturer's instructions. In addition, 3% v/v DMSO (Sigma) was used. The program was set as follows: two minutes at 94° C., then 30 cycles of (94° C. for 30 seconds, 60° C. for 30 seconds and 72° C. for 1.5 minutes) and ended by eight minutes at 68° C. The resulting 1.2 kb product was cloned directly into the pCR4Blunt-TOPO vector (Invitrogen) according to the manufacturer's protocol, resulting in pCR4Blunt-TOPO.Bsu-Age. The construct was checked by digestion with PvuII (New England Biolabs). The Bsu-Age fragment was isolated from the pCR4Blunt-TOPO.Bsu-Age plasmid by digestion with Bsu36I (New England Biolabs) and treated with Klenow enzyme (New England Biolabs) to blunt ends. The DNA was then purified using the PCR purification kit (Qiagen) and was digested with AgeI (New England Biolabs). The 1 kb fragment was isolated from gel using the GeneClean II kit (BIO 101, Inc.). In parallel, construct pAdApt35.Luc (described in WO 00/70071) was digested with BglII and treated with Klenow enzyme. The DNA was purified using the PCR purification kit (Qiagen). The purified DNA was digested with AgeI (New England Biolabs) and dephosphorylated with SAP (Roche). The 5.8 kb fragment was isolated from gel with the GeneClean II kit (BIO 101, Inc.). The two fragments were mixed in equimolar amounts in a ligation reaction and transformed into Ti-resistant EM DH10B cells (Invitrogen). This resulted in plasmid pAdApt35Bsu.Luc.

To generate E1-deleted viruses, pAdApt35Bsu.Luc was digested with pIPsp-I and co-transfected onto PER55K clone 16 cells with NotI-digested pWE.Ad35-3481 (Example 7) and with pWE.Ad35-3481ΔE3 as described before. pWE.Ad35-3481ΔE3 contains the same E3 deletion as described for pWE.Ad35.pIX-rITRΔE3 (Example 2) and was generated according to the method described in Example 7 using construct pWE.Ad35-3481ΔNdeI and a 26.6 kb NdeI fragment from pWE.Ad35.pIX-rITRΔE3.

In addition, E1-deleted Ad35 viruses were generated that contained the E4-Orf6 and E4-Orf6/7 sequences from Ad5 in the viral backbone replacing the native Ad35 sequences (see Example 16 for the generation of such viruses on unmodified PER.C6™ cells). In the current example pAdApt35Bsu.Luc digested with pIPsp-I is co-transfected with NotI/EcoRV-digested pWE.Ad35.pIX-EcoRV and with PacI/NotI-digested pBr.Ad35.PR5Orf6 (with and without E3 region). All transfections gave rise to full CPE within a week following transfection and cells and medium were harvested as described before. Viruses were then plaque purified and viral stocks amplified on the appropriate complementation cells and those originating from single plaques were analyzed by PCR for integrity of the transgene region. Transgene PCRs were done as described in Example 3 using primers AdApt35CMVF and pIXrevN2. FIG. 32 shows an example of the PCR results on plaques originating from Ad35Bsu.Luc and from Ad35Bsu.Luc.5Orf6 viruses.

Irrespective of the presence of the E3 region or of the E4-Orf6 sequence in the viral backbone, all tested plaques (five to ten for each virus) contained an intact transgene. One exception occurred in one of the plaques from Ad35Bsu.Luc viruses that showed a faint band at approximately 1.6 kb (FIG. 32; lane 12), probably originating from a minor amount of viruses with a deletion. The faint band at approximately 500 bp that occurs in all virus samples, is a background band of the primers on the viral backbone. The observation that E3-containing Ad35 viruses with a luciferase-expression cassette proved stable following plaque purification is in contrast to previous results with Ad35.AdApt.Luc viruses that are fully E1-deleted and do not contain the 166 bp 3' 55K-coding sequence. Using standard pAdApt35.Luc plasmids, we were not able to generate plaque-purified viruses containing the E3 region. Thus, with incorporation of the extra 55K sequences in the backbone, we can now make viruses of more than 34.6 kb total length without severe instability. This closely matches the length of a wild-type Ad35 virus. If an E3-deleted backbone were used, the capacity for foreign sequences theoretically would be over 5 kb. Obviously, it is possible to incorporate more E1B-55K sequences than in the current example and/or to combine the 3' 55K sequences with heterologous enhancer sequences without departing from the invention disclosed herein.

Tables

TABLE I

Yields of E1- and E1/E3-deleted Ad35 viruses on clone #16 cells produced on triple-layer flasks.

| Virus | Scale (T175$^{III}$ flasks) | Total # of Virus Particles after DSP | VP/cell |
|---|---|---|---|
| Ad35.AdApt.eGFP | 4 | 7.5 × 10$^{11}$ | 2500 |
| Ad35.ΔE3.AdApt.empty | 8 | 2 × 10$^{12}$ | 3300 |
| Ad35.ΔE3.AdApt.LacZ | 8 | 3.8 × 10$^{11}$ | 600 |
| Ad35.ΔE3.AdApt.MV-F | 4 | 8.8 × 10$^{11}$ | 2900 |
| Ad35.ΔE3.AdApt.MV-H | 8 | 2.6 × 10$^{12}$ | 4250 |

TABLE II

Transgene (LacZ) activity test on A549 using crude lysates from second passage virus. Percent blue cells is given for each amount of virus used for infection.

| Virus | 10 μl | 1 μl | 0.1 μl |
|---|---|---|---|
| Ad35.AdApt.LacZ.rsv | 95 | 15 | <1 |
| Ad35.ΔE3.AdApt.LacZ.rsv | 90 | 10 | <1 |
| Ad35.AdApt.LacZ.C4 | 2 | <0.1 | 0 |
| Ad35.ΔE3.AdApt.LacZ.C4 | 15 | <1 | <0.1 |

TABLE III

Transgene (Luciferase) activity test on A549 using crude lysates from second passage virus. Activity is expressed in relative light units (RLU).

| Virus | 10 μl | 1 μl | 0.1 μl | 0.01 μl |
|---|---|---|---|---|
| Ad35.AdApt.Luc.rsv | 845453 | 27940 | 178 | 26 |
| Ad35.ΔE3.AdApt.Luc.rsv | 258269 | 2217 | 46 | 6 |
| Ad35.AdApt.Luc.C4 | 6130 | 175 | 18 | 33 |
| Ad35.ΔE3.AdApt.Luc.C4 | 814642 | 6278 | 147 | 23 |
| Ad35.ΔE1AΔ21K.Luc | 1514698 | 50196 | 503 | 57 |

TABLE IV

Primer sequences.

| name | sequence | SEQ. ID. NO. |
|---|---|---|
| 35FR | 5'-CGGGATCCACTTTATTTTAGTTGTCGTCTTC-3' | 1 |
| 35R4 | 5'-CGGAATTCTTAATTAAGGGAAATGCAAATCTGTGAGG-3' | 2 |
| 35psi-For | 5'-GTGGTATTTATGGCAGGGTG-3' | 3 |
| DF35-1 | 5'-CACTCACCACCTCCAATTCC-3' | 4 |
| 5E4F | 5'-CGGGATCCGTTTGTGTTATGTTTCAACGTG-3' | 5 |
| 5E4R | 5'-GCTGGCGAGCTCGGCGGAGTAACTTGTATGTG-3' | 6 |
| 35SITR | 5'-GATCCGGAGCTCACAACGTCATTTTCCCACG-3' | 7 |
| 353ITR | 5'-AGGAATTCGCGGCCGCATTTAAATC-3' | 8 |
| E4-F1 | 5'-AGAGGAACACATTCCCCC-3' | 9 |
| E4-R2 | 5'-GGGGAGAAAGGACTGTGTATTCTGTCAAATGG-3' | 10 |
| E4-F3 | 5'-TTTGACAGAATACACAGTCCTTTCTCCCCGGCTGG-3' | 11 |
| E4-R4 | 5'-ACAAAATACGAGAATGACTACGTCCGGCGTTCC-3' | 12 |
| E4-F5 | 5'-GGACGTAGTCATTCTCGTATTTTGTATAGC-3' | 13 |

TABLE IV-continued

Primer sequences.

| name | sequence | SEQ. ID. NO. |
|---|---|---|
| E4-R6 | 5'-TCACCAACACAGTGGGGG-3' | 14 |
| NF-1 | 5'-CCACAACCCCCACTACTCCC-3' | 15 |
| NR-2 | 5'-CGTCTCTTCCCTCTCCTCTCC-3' | 16 |
| NcoI-R | 5'-AGGATCATCCGCTGCTGCCC-3' | 17 |
| NcoI-F | 5'-CATCAGGATAGGGCGGTGG-3' | 18 |
| 35E3for | 5'-AATGACTAATGCAGGTGCGC-3' | 19 |
| 35E3rev | 5'-CGACGCGTTGTAGTCGTTGAGCTTCTAG-3' | 20 |
| AdApt35CMVF | 5'-GTAGGTGTCAGCCTAGGTGGTC-3' | 21 |
| 35pIXR | 5'-TCATGTCAGCTGCAAGACAG-3' | 22 |
| SV40for | 5'-CAATGTATCTTATCATGTCTAG-3' | 23 |
| pIX5Rmfe | 5'-CTCTCTCAATTGCAGATACAAAACTACATAAGACC-3' | 24 |
| pIX35Fmfe | 5'-CTCTCTCAATTGTCTGTCTTGCAGCTGACATG-3' | 25 |
| AdApt35pIXrev | 5'-CAATCTGTCCATCTGAAAATCC-3' | 26 |
| pIXcosF-2 | 5'-CTGCTGGACGTCGCGGCCGCGACATGAGTGGAAATGCTTC-3' | 27 |
| Adapt35-3 | 5'-TGCAAATCTGTGAGGGGAAC-3' | 28 |
| 35D21 | 5'-TTA GAT CCA TGG ATC CCG CAG ACT C-3' | 29 |
| 35B3 | 5'-CCT CAG CCC CAT TTC CAG-3' | 30 |
| 35F1 | 5'-CGGAATTCTTAATTAATCGACATCATCAATAATATACCTTATAG-3' | 31 |
| 35R4 | 5'-CGGAATTCTTCTTAATTAAGGGAAATGCAAATCTGTGAGG-3' | 32 |
| Ad3555KMfeF | 5'-AACCAAGCTTCAATTGTCTCTGAA-3' | 33 |
| Ad35pIXNcoR | 5'-CCACCCATGGCAGCTGCAAGACAG-3' | 34 |
| Ad35pIXrev | 5'-TCAGCTGCAAGACAGAAAAAAC-3' | 35 |
| Epr-F | 5'-GTGTTTACTTAAGGTGACGTC-3' | 36 |
| Epr-R | 5'-GAAAGCCAGCTCCTATGAGC-3' | 37 |
| pIXrev | 5'-GGCGGGTTGAACGGGTCTTCCA-3' | 38 |
| pIXrev-N2 | 5'-GATGGGAGACGCCCTGTCAGATAAGG-3' | 39 |
| 35E1Blong | 5'-AAGGTGACGTCAATATTTGTGTG-3' | 40 |
| Ad35E1bpromrev | 5'-ATGAAAGCCAGCTCCTATGAG-3' | 41 |
| pIXrev-Ad5 | 5'-AGGGGAGGAAGCCTTCAGG-3' | 42 |
| Bsu55KF | 5'-AGG TGG GCG TAG AGG AAT G-3' | 43 |
| Age-pIXR | 5'-CAA GAC GGG ATC TTG GCG G-3' | 44 |

TABLE V

List of constructs used for generation of E1-deleted Ad35-based viruses on PER.C6 ™ cells as described in the Examples. Adapter constructs were digested with PacI; pWE.Ad35.pIX-EcoRV was digested with NotI and EcoRV; E4-modified pBr-based constructs were digested with PacI and NotI.

| No. | Constructs | | | CPE |
|---|---|---|---|---|
| 1 | pAdApt35.eGFP | pWE.Ad35.pIX-EcoRV | pBr.Ad35.PR5E4 | Yes |
| 2 | pAdApt35.eGFP | pWE.Ad35.pIX-EcoRV | pBr.Ad35.PR5Orf6 | Yes |
| 3 | pAdApt35.eGFP | pWE.Ad35.pIX-EcoRV | pBr.Ad35.ΔE3PR5E4 | Yes |
| 4 | pAdApt35.eGFP | pWE.Ad35.pIX-EcoRV | pBr.Ad35.ΔE3.PR5Orf6 | Yes |
| 5 | pAdApt35.eGFP | | pWE.Ad35.pIX-rITRxNotI | No |
| 6 | pAdApt5.eGFP | | pWE.Ad5.AflII-rITRxPacI | Yes |

TABLE VI

Percentages of LacZ-positive plaques of Ad35 viruses having different promoter sequences driving pIX expression.
(NP = no plaques visible)

| | % of blue plaques | | |
|---|---|---|---|
| Virus name | with E3 region | w/o E3 region | virus length (incl. E3 region) |
| Ad35.AdApt.LacZ | 0% | 50% | 36.1 kb |
| Ad535.AdApt.LacZ | NP | 100% | 36.1 kb |
| Ad35.AdAptB.LacZ | 5% | 80% | 36.2 kb |
| Ad35.AdApt.LacZ.rsv | 90% | 100% | 36.5 kb |
| Ad35ΔSM.LacZ | 50% | 100% | 36.7 kb |

REFERENCES

Abrahamsen, K., Kong, H.-L., Mastrangeli, A., Brough, D., Lizonova, A., Crystal, R. and Falck-Pedersen, E. (1997). Construction of an adenovirus type 7a E1A⁻ vector. J. Virol. 11:8946-8951.

Babiss, L. E. and Vales, L. D. (1991). Promoter of the adenoviral polypeptide 1x gene: Similarity to E1B and inactivation by substitution of the simian virus TATA element. J. Virol. 65(2), p. 598-605.

Bett, A. J., Prevec, L. and Graham, F. L. (1993). Packaging capacity and stability of human adenovirus type 5 vectors. J. Virol. 67(10), p. 5911-5921.

Boshart, M., Weber, F., Jahn, G., Dorsch-Hasler, K., Fleckenstein B. and Schaffner W. (1985). A very strong enhancer is located upstream of an immediate early gene of human cytomegalovirus. Cell 41, 521-530.

Caravokyri, C. and Leppard, K. N. (1995). Constitutive episomal expression of polypeptide IX (pIX) in a 293-based cell line complements the deficiency of pIX mutant adenovirus type 5. J. Virol. 69(11), p. 6627-6633.

Fallaux, F. J., Kranenburg, O., Cramer, S. J., Houweling, A., van Ormondt, H., Hoeben, R. C. and van der Eb, A. J. (1996). Characterization of 911: A new helper cell line for the titration and propagation of early region 1-deleted adenoviral vectors. Hum. Gene Ther. 7, p. 215-222.

Fallaux, F. J., Bout, A., van der Velde, I., van den Wollenberg, D. J., Hehir, K. M., Keegan, J., Auger, C., Cramer, S. J., van Ormondt, H., van der Eb, A. J., Valerio, D. and Hoeben, R. C. (1998). New helper cells and matched early region 1-deleted adenovirus vectors prevent generation of replication competent adenoviruses. Hum. Gene Ther. 9, p. 1909-1917.

Farina, S. F., Gao, G. P., Xiang, Z. Q., Rux, J. J., Burnett, R. M., Alvira, M. R., Marsh, J., Ertl, H. C. and Wilson, J. M. (2001). Replication-defective vector based on a chimpanzee adenovirus. J. Virol. 75(23), p. 11603-11613.

Francki, R. I. B., Fauquet, C. M., Knudson, L. and Brown, F. (1991). Classification and nomenclature of viruses. Fifth report of the international committee on taxonomy of viruses. Arch. Virol. Suppl. 2, p. 140-144.

Furcinitti, P. S., van Oostrom, J. and Burnett R. M. (1989). Adenovirus polypeptide IX revealed as capsid cement by difference images from electron microscopy and crystallography. EMBO. J. 8(12), p. 3563-3570.

Grable, M. and Hearing, P. (1990). Adenovirus type 5 packaging domain is composed of a repeated element that is functionally redundant. J. Virol. Vol. 64, No. 5, p. 2047-2056.

Graham, F. O., Smiley, J., Russell, W. and Naim, R. (1970). Characteristics of a human cell line transformed by DNA from human adenovirus type 5. J. Gen. Virol. 36, p. 59-72.

Gustin, K. E. and Imperiale, M. J. (1998). Encapsidation of viral DNA requires the adenovirus LI 52/55-kilodalton protein. J. Virol. Vol. 72, No. 10, p. 7860-7870.

Ghosh-Choudhury, G., Haj-Ahmad, Y. and Graham, F. L. (1987). Protein IX, a minor component of the human adenovirus capsid, is essential for the packaging of full length genomes. EMBO. J. 6(6), p. 1733-1739.

Hagmeyer, B. M., Duyndam, M. C., Angel, P., De Groot, R. P., Verlaan, M., Elfferich, P., Van der Eb, A. J. and Zantema, A. (1996). Oncogene 12: 1025-1032.

Hehir, K. M., Armentano, D., Cardoza, L. M., Choquette, T. L., Berthelette, P. B., White, G. A., Couture, L. A., Everton, M. B., Keegan, J., Martin, J. M., Pratt, D. A., Smith, M. P., Smith, A. E. and Wadsworth, S. C. (1996). Molecular characterization of replication-competent variants of adenovirus vectors and genome modifications to prevent their occurrence. J. Virol. 70(12), p. 8459-8467.

Herrman, C. H. and Mathews, M. B. (1989). The adenovirus E1B 19-kilodalton protein stimulates gene expression by increasing DNA levels. Mol. Cell. Biol. 9, p. 5412-5423.

Horwitz, M. S. (2001). Adenovirus immunoregulatory genes and their cellular targets. Virology 279(1), p. 1-8.

Leppard, K. N. (1997). E4 gene function in adenovirus, adenovirus vector and adeno-associated virus infections. J. Gen. Virol. 78, p. 2131-2138.

Leppard, K. N. (1998). Regulated RNA processing and RNA transport during adenovirus infection. Seminars in Virology 8, p. 301-307.

Lutz, P., Rosa-Calatrava, M. and Kedinger, C. (1997). The product of the adenovirus intermediate gene IX is a transcriptional activator. J. Virol. 71(7), p. 5102-5109.

Pilder, S., Logan, J. and Shenk, T. (1984). Deletion of the gene encoding the adenovirus type 5 early region 1B 21,000-molecular-weight polypeptide leads to degradation of viral and host cell DNA. J. Virol. 52(2), p. 664-671.

Pilder, S., Moore, M., Logan, J. and Shenk, T. (1986). The adenovirus E1B 55K transforming polypeptide modulates transport or cytoplasmic stabilization of viral and host cell mRNAs. Mol. Cell. Biol. 6, p. 470-476.

Rao, L., Debbas, M., Sabbatini, P., Hockenbery, D., Korsmeyer, S. and White, E. (1992). The adenovirus E1A proteins induce apoptosis, which is inhibited by the E1B 19-kDa and Bcl-2 proteins. Proc. Natl. Acad. Sci. USA Vol. 89, pp. 7742-7746.

Reese, M. G. and Eeckman, F. H. (1995). Novel neural network algorithms for improved eukaryotic promoter site recognition. Talk and Abstract from the Seventh International Genome Sequencing and Analysis Conference, Hyatt Regency, Hilton Head Island, South Carolina, Sep. 16-20, 1995. (http://www.fruitfly.org/seq_tools/promoter.html).

Robert, J.-J., Gauffeny, I., Maccario, J., Jullien, C., Benoit, P., Vigne, E., Crouzet, J., Perricaudet, M. and Yeh, P. (2001). Degenerated pIX-IVa2 adenoviral vector sequences lowers reacquisition of the E1 genes during virus amplification in 293 cells. Gene Ther. 8, p. 1713-1720.

Russell, W. C. (2000). Update on adenoviruses and its vectors. J. Gen. Virol. 81, pp. 2573-2604. Sambrook, J. and Russell, D. (2001). Molecular Cloning: A laboratory manual. Third Edition. Cold Spring Harbor Press. ISBN 0-87969-576-5.

Shabram, P. W., Giroux, D. D., Goudreau, A. M., Gregory, R. J., Horn, M. T., Huyghe, B. G., Liu, X., Nunnally, M. H., Sugarman, B. J. and Sutjipto, S. (1997). Analytical anion-exchange HPLC of recombinant type-5 adenoviral particles. Hum. Gene Ther. 8(4): 453-465.

Shenk, T. (1996). Adenoviridae: The viruses and their replication. In Virology, eds. Fields, B. N., Knipe, D. M. and Howley, P. M. (Lippincott-Raven, New York), Vol. 2, pp. 2111-2148.

Van der Vliet, P. C. (1995). Adenovirus DNA replication. In The Molecular Repertoire of Adenoviruses II, eds. Doerfler, W. and Böhm, P. (Springer-Verlag, Berlin). Current Topics in Microbiology and Immunology 199/II, pp. 1-30.

White, E., Grodzicker, T. and Stillman, B. W. (1984). Mutations in the gene encoding the adenovirus early region 1B 19,000 molecular-weight tumor antigen cause degradation of chromosomal DNA. J. Virol. 52(2), p. 410-419.

Yew, P. R. and Berk, A. J. (1992). Inhibition of p53 transactivation required for transformation by adenovirus early region 1B protein. Nature 357, pp. 82-85.

Zhang, W., Low, J. A., Christensen, J. B. and Imperiale, M. I. (2001). Role for the adenovirus IVa2 protein in packaging of viral DNA. J. Virol. Vol. 75 No. 21, pp. 10446-10454.

What is claimed is:

1. A recombinant subgroup B adenovirus particle comprising an adenovirus genome wherein the genome comprises a deletion in the E1-region, which adenovirus genome does not encode a functional E1B 55K gene product, said adenovirus genome comprising a functional pIX coding sequence under control of an expression sequence, said expression sequence-comprising part of the 3' end of the E1B 55K coding sequence-containing from 150 to 600 nucleotides of adenovirus sequences directly upstream of the pIX open reading frame of a wild-type subgroup B adenovirus, and said expression sequence being capable of increasing expression of the pIX coding sequence in a packaging cell, relative to the expression of said pIX coding sequence when preceded by sequences between the E1B 55K stop codon and the start codon of pIX and without nucleotides from the 3' end of the E1B55K coding sequence.

2. The recombinant adenovirus particle of claim 1, wherein said expression sequence contains from 150 to 250 nucleotides of the adenovirus sequences that are directly upstream of the pIX open reading frame of a wild-type subgroup B adenovirus.

3. The recombinant adenovirus particle of claim 1, wherein said expression sequence contains 166 base pairs of the 3' end of the E1B 55K open reading frame sequence.

4. The recombinant adenovirus particle of claim 1, wherein said expression sequence contains from 150 to 200 nucleotides of adenovirus sequences directly upstream of the pIX open reading frame of a wild-type subgroup B adenovirus.

5. The recombinant adenovirus particle of claim 1, wherein said adenovirus particle is an adenovirus serotype 35 particle or an adenovirus serotype 11 particle.

6. The recombinant adenovirus particle of claim 1, further comprising a sequence encoding a functional E4-orf6 protein of adenovirus subgroup C origin.

7. An isolated nucleic acid, comprising a genome of the recombinant adenovirus particle of claim 1.

8. A vaccine comprising the recombinant adenovirus particle of claim 1 and a suitable carrier or an adjuvant.

9. A recombinant adenovirus packaging cell comprising the recombinant adenovirus particle of claim 1.

10. A recombinant subgroup B adenovirus particle comprising an adehoviral genome comprising a pIX coding sequence and with a deletion in the E1-region and which adenovirus particle does not encode a functional E1B 55K gene product, wherein the pIX coding sequence is under control of a heterologous promoter, wherein said heterologous promoter is capable of increasing expression of the pIX coding sequence in a packaging cell, relative to the expression of said pIX coding sequence when preceded by sequences between the E1B 55K stop codon and the start codon of pIX and without nucleotides from the E1B 55K coding sequence.

11. The recombinant adenovirus particle of claim 10, wherein said heterologous promoter comprises a nucleic acid sequence selected from the group consisting of a non-endogenous adenoviral proximal pIX promoter, a non-adenovirus viral promoter, a cellular promoter, a synthetic promoter and a hybrid promoter.

12. The recombinant adenovirus particle of claim 11, wherein said heterologous promoter is selected from the group consisting of an Ad5 proximal pIX promoter or a Rous Sarcoma Virus promoter.

* * * * *

SEQUENCE LISTING

```
<160> NUMBER OF SEQ ID NOS: 65

<210> SEQ ID NO 1
<211> LENGTH: 31
<212> TYPE: DNA
<213> ORGANISM: Artificial
<220> FEATURE:
<223> OTHER INFORMATION: primer 35FR

<400> SEQUENCE: 1
cgggatccac tttattttag ttgtcgtctt c                                        31

<210> SEQ ID NO 2
<211> LENGTH: 37
<212> TYPE: DNA
<213> ORGANISM: Artificial
<220> FEATURE:
<223> OTHER INFORMATION: primer 35R4

<400> SEQUENCE: 2
cggaattctt aattaaggga aatgcaaatc tgtgagg                                  37

<210> SEQ ID NO 3
<211> LENGTH: 20
<212> TYPE: DNA
<213> ORGANISM: Artificial
<220> FEATURE:
<223> OTHER INFORMATION: primer 35psi-For

<400> SEQUENCE: 3
gtggtattta tggcagggtg                                                     20
```

```
<210> SEQ ID NO 4
<211> LENGTH: 20
<212> TYPE: DNA
<213> ORGANISM: Artificial
<220> FEATURE:
<223> OTHER INFORMATION: primer DF35-1

<400> SEQUENCE: 4
cactcaccac ctccaattcc                                              20

<210> SEQ ID NO 5
<211> LENGTH: 30
<212> TYPE: DNA
<213> ORGANISM: Artificial
<220> FEATURE:
<223> OTHER INFORMATION: primer 5E4F

<400> SEQUENCE: 5
cgggatccgt tgtgttatg tttcaacgtg                                    30

<210> SEQ ID NO 6
<211> LENGTH: 32
<212> TYPE: DNA
<213> ORGANISM: Artificial
<220> FEATURE:
<223> OTHER INFORMATION: primer 5E4R

<400> SEQUENCE: 6
gctggcgagc tcggcggagt aacttgtatg tg                                32

<210> SEQ ID NO 7
<211> LENGTH: 31
<212> TYPE: DNA
<213> ORGANISM: Artificial
<220> FEATURE:
<223> OTHER INFORMATION: primer 355ITR

<400> SEQUENCE: 7
gatccggagc tcacaacgtc attttcccac g                                 31

<210> SEQ ID NO 8
<211> LENGTH: 25
<212> TYPE: DNA
<213> ORGANISM: Artificial
<220> FEATURE:
<223> OTHER INFORMATION: primer 353ITR

<400> SEQUENCE: 8
aggaattcgc ggccgcattt aaatc                                        25

<210> SEQ ID NO 9
<211> LENGTH: 18
<212> TYPE: DNA
<213> ORGANISM: Artificial
<220> FEATURE:
<223> OTHER INFORMATION: primer E4-F1

<400> SEQUENCE: 9
agaggaacac attccccc                                                18

<210> SEQ ID NO 10
<211> LENGTH: 32
<212> TYPE: DNA
<213> ORGANISM: Artificial
<220> FEATURE:
<223> OTHER INFORMATION: primer E4-R2
```

```
<400> SEQUENCE: 10
ggggagaaag gactgtgtat tctgtcaaat gg                          32

<210> SEQ ID NO 11
<211> LENGTH: 35
<212> TYPE: DNA
<213> ORGANISM: Artificial
<220> FEATURE:
<223> OTHER INFORMATION: primer E4-F3

<400> SEQUENCE: 11
tttgacagaa tacacagtcc tttctccccg gctgg                       35

<210> SEQ ID NO 12
<211> LENGTH: 33
<212> TYPE: DNA
<213> ORGANISM: Artificial
<220> FEATURE:
<223> OTHER INFORMATION: primer E4-R4

<400> SEQUENCE: 12
acaaaatacg agaatgacta cgtccggcgt tcc                         33

<210> SEQ ID NO 13
<211> LENGTH: 30
<212> TYPE: DNA
<213> ORGANISM: Artificial
<220> FEATURE:
<223> OTHER INFORMATION: primer E4-F5

<400> SEQUENCE: 13
ggacgtagtc attctcgtat tttgtatagc                             30

<210> SEQ ID NO 14
<211> LENGTH: 18
<212> TYPE: DNA
<213> ORGANISM: Artificial
<220> FEATURE:
<223> OTHER INFORMATION: primer E4-R6

<400> SEQUENCE: 14
tcaccaacac agtggggg                                          18

<210> SEQ ID NO 15
<211> LENGTH: 20
<212> TYPE: DNA
<213> ORGANISM: Artificial
<220> FEATURE:
<223> OTHER INFORMATION: primer NF-1

<400> SEQUENCE: 15
ccacaacccc cactactccc                                        20

<210> SEQ ID NO 16
<211> LENGTH: 21
<212> TYPE: DNA
<213> ORGANISM: Artificial
<220> FEATURE:
<223> OTHER INFORMATION: primer NR-2

<400> SEQUENCE: 16
cgtctcttcc ctctcctctc c                                      21

<210> SEQ ID NO 17
```

```
<211> LENGTH: 20
<212> TYPE: DNA
<213> ORGANISM: Artificial
<220> FEATURE:
<223> OTHER INFORMATION: primer NcoI-R

<400> SEQUENCE: 17
aggatcatcc gctgctgccc                                                  20

<210> SEQ ID NO 18
<211> LENGTH: 19
<212> TYPE: DNA
<213> ORGANISM: Artificial
<220> FEATURE:
<223> OTHER INFORMATION: primer NcoI-F

<400> SEQUENCE: 18
catcaggata gggcggtgg                                                   19

<210> SEQ ID NO 19
<211> LENGTH: 20
<212> TYPE: DNA
<213> ORGANISM: Artificial
<220> FEATURE:
<223> OTHER INFORMATION: primer 35E3for

<400> SEQUENCE: 19
aatgactaat gcaggtgcgc                                                  20

<210> SEQ ID NO 20
<211> LENGTH: 28
<212> TYPE: DNA
<213> ORGANISM: Artificial
<220> FEATURE:
<223> OTHER INFORMATION: primer 35E3rev

<400> SEQUENCE: 20
cgacgcgttg tagtcgttga gcttctag                                         28

<210> SEQ ID NO 21
<211> LENGTH: 22
<212> TYPE: DNA
<213> ORGANISM: Artificial
<220> FEATURE:
<223> OTHER INFORMATION: primer AdApt35CMVF

<400> SEQUENCE: 21
gtaggtgtca gcctaggtgg tc                                               22

<210> SEQ ID NO 22
<211> LENGTH: 20
<212> TYPE: DNA
<213> ORGANISM: Artificial
<220> FEATURE:
<223> OTHER INFORMATION: primer 35pIXR

<400> SEQUENCE: 22
tcatgtcagc tgcaagacag                                                  20

<210> SEQ ID NO 23
<211> LENGTH: 22
<212> TYPE: DNA
<213> ORGANISM: Artificial
<220> FEATURE:
<223> OTHER INFORMATION: primer SV40for

<400> SEQUENCE: 23
```

```
caatgtatct tatcatgtct ag                                              22

<210> SEQ ID NO 24
<211> LENGTH: 35
<212> TYPE: DNA
<213> ORGANISM: Artificial
<220> FEATURE:
<223> OTHER INFORMATION: primer pIX5Rmfe

<400> SEQUENCE: 24
ctctctcaat tgcagataca aaactacata agacc                                35

<210> SEQ ID NO 25
<211> LENGTH: 32
<212> TYPE: DNA
<213> ORGANISM: Artificial
<220> FEATURE:
<223> OTHER INFORMATION: primer pIX35Fmfe

<400> SEQUENCE: 25
ctctctcaat tgtctgtctt gcagctgaca tg                                   32

<210> SEQ ID NO 26
<211> LENGTH: 22
<212> TYPE: DNA
<213> ORGANISM: Artificial
<220> FEATURE:
<223> OTHER INFORMATION: primer AdApt35pIXr

<400> SEQUENCE: 26
caatctgtcc atctgaaaat cc                                              22

<210> SEQ ID NO 27
<211> LENGTH: 40
<212> TYPE: DNA
<213> ORGANISM: Artificial
<220> FEATURE:
<223> OTHER INFORMATION: primer pIXcosF-2

<400> SEQUENCE: 27
ctgctggacg tcgcggccgc gacatgagtg gaaatgcttc                           40

<210> SEQ ID NO 28
<211> LENGTH: 20
<212> TYPE: DNA
<213> ORGANISM: Artificial
<220> FEATURE:
<223> OTHER INFORMATION: primer Adapt35-3

<400> SEQUENCE: 28
tgcaaatctg tgagggggaac                                                20

<210> SEQ ID NO 29
<211> LENGTH: 25
<212> TYPE: DNA
<213> ORGANISM: Artificial
<220> FEATURE:
<223> OTHER INFORMATION: primer 35D21

<400> SEQUENCE: 29
ttagatccat ggatcccgca gactc                                           25

<210> SEQ ID NO 30
<211> LENGTH: 18
<212> TYPE: DNA
```

```
<213> ORGANISM: Artificial
<220> FEATURE:
<223> OTHER INFORMATION: primer 35B3

<400> SEQUENCE: 30
cctcagcccc atttccag                                                    18

<210> SEQ ID NO 31
<211> LENGTH: 44
<212> TYPE: DNA
<213> ORGANISM: Artificial
<220> FEATURE:
<223> OTHER INFORMATION: primer 35F1

<400> SEQUENCE: 31
cggaattctt aattaatcga catcatcaat aatatacctt atag                       44

<210> SEQ ID NO 32
<211> LENGTH: 40
<212> TYPE: DNA
<213> ORGANISM: Artificial
<220> FEATURE:
<223> OTHER INFORMATION: primer 35R4

<400> SEQUENCE: 32
cggaattctt cttaattaag ggaaatgcaa atctgtgagg                            40

<210> SEQ ID NO 33
<211> LENGTH: 24
<212> TYPE: DNA
<213> ORGANISM: Artificial
<220> FEATURE:
<223> OTHER INFORMATION: primer Ad3555KMfeF

<400> SEQUENCE: 33
aaccaagctt caattgtctc tgaa                                             24

<210> SEQ ID NO 34
<211> LENGTH: 24
<212> TYPE: DNA
<213> ORGANISM: Artificial
<220> FEATURE:
<223> OTHER INFORMATION: primer Ad35pIXNcoR

<400> SEQUENCE: 34
ccacccatgg cagctgcaag acag                                             24

<210> SEQ ID NO 35
<211> LENGTH: 22
<212> TYPE: DNA
<213> ORGANISM: Artificial
<220> FEATURE:
<223> OTHER INFORMATION: primer Ad35pIXrev

<400> SEQUENCE: 35
tcagctgcaa gacagaaaaa ac                                               22

<210> SEQ ID NO 36
<211> LENGTH: 21
<212> TYPE: DNA
<213> ORGANISM: Artificial
<220> FEATURE:
<223> OTHER INFORMATION: primer Epr-F

<400> SEQUENCE: 36
gtgtttactt aaggtgacgt c                                                21
```

```
<210> SEQ ID NO 37
<211> LENGTH: 20
<212> TYPE: DNA
<213> ORGANISM: Artificial
<220> FEATURE:
<223> OTHER INFORMATION: primer Epr-R

<400> SEQUENCE: 37
gaaagccagc tcctatgagc                                             20

<210> SEQ ID NO 38
<211> LENGTH: 22
<212> TYPE: DNA
<213> ORGANISM: Artificial
<220> FEATURE:
<223> OTHER INFORMATION: primer pIXrev

<400> SEQUENCE: 38
ggcgggttga acgggtcttc ca                                          22

<210> SEQ ID NO 39
<211> LENGTH: 26
<212> TYPE: DNA
<213> ORGANISM: Artificial
<220> FEATURE:
<223> OTHER INFORMATION: primer pIXrev-N2

<400> SEQUENCE: 39
gatgggagac gccctgtcag ataagg                                      26

<210> SEQ ID NO 40
<211> LENGTH: 23
<212> TYPE: DNA
<213> ORGANISM: Artificial
<220> FEATURE:
<223> OTHER INFORMATION: primer 35E1Blong

<400> SEQUENCE: 40
aaggtgacgt caatatttgt gtg                                         23

<210> SEQ ID NO 41
<211> LENGTH: 21
<212> TYPE: DNA
<213> ORGANISM: Artificial
<220> FEATURE:
<223> OTHER INFORMATION: primer Ad35E1bpromrev

<400> SEQUENCE: 41
atgaaagcca gctcctatga g                                           21

<210> SEQ ID NO 42
<211> LENGTH: 19
<212> TYPE: DNA
<213> ORGANISM: Artificial
<220> FEATURE:
<223> OTHER INFORMATION: primer pIXrev-Ad5

<400> SEQUENCE: 42
aggggaggaa gccttcagg                                              19

<210> SEQ ID NO 43
<211> LENGTH: 19
<212> TYPE: DNA
<213> ORGANISM: Artificial
<220> FEATURE:
```

```
<223> OTHER INFORMATION: primer Bsu55KF

<400> SEQUENCE: 43
aggtgggcgt agaggaatg                                                   19

<210> SEQ ID NO 44
<211> LENGTH: 19
<212> TYPE: DNA
<213> ORGANISM: Artificial
<220> FEATURE:
<223> OTHER INFORMATION: primer Age-pIXR

<400> SEQUENCE: 44
caagacggga tcttggcgg                                                   19

<210> SEQ ID NO 45
<211> LENGTH: 102
<212> TYPE: DNA
<213> ORGANISM: Adenovirus type 2
<220> FEATURE:
<221> NAME/KEY: misc_feature
<223> OTHER INFORMATION: Ad2 proximal pIX upstream sequence
<220> FEATURE:
<221> NAME/KEY: E1B 55K stopcodon
<222> LOCATION: (1)..(3)
<220> FEATURE:
<221> NAME/KEY: Sp1 site
<222> LOCATION: (18)..(24)
<220> FEATURE:
<221> NAME/KEY: TATA_signal
<222> LOCATION: (45)..(51)
<220> FEATURE:
<221> NAME/KEY: pIX startcodon
<222> LOCATION: (99)..(102)

<400> SEQUENCE: 45
tgaggtactg aaatgtgtgg gcgtggctta agggtgggaa agaatatata aggtggggggt    60 ctcatgtagt tttgtatctg ttttgcagca gccgccgcca tg                        102

<210> SEQ ID NO 46
<211> LENGTH: 105
<212> TYPE: DNA
<213> ORGANISM: Adenovirus type 5
<220> FEATURE:
<221> NAME/KEY: misc_feature
<223> OTHER INFORMATION: Ad5 proximal pIX upstream sequence
<220> FEATURE:
<221> NAME/KEY: E1B 55K stopcodon
<222> LOCATION: (1)..(3)
<220> FEATURE:
<221> NAME/KEY: Sp1 site
<222> LOCATION: (18)..(24)
<220> FEATURE:
<221> NAME/KEY: TATA_signal
<222> LOCATION: (45)..(51)
<220> FEATURE:
<221> NAME/KEY: pIX startcodon
<222> LOCATION: (103)..(105)

<400> SEQUENCE: 46
tgaggtactg aaatgtgtgg gcgtggctta agggtgggaa agaatatata aggtggggggt    60 cttatgtagt tttgtatctg ttttgcagca gccgccgccg ccatg                     105

<210> SEQ ID NO 47
<211> LENGTH: 84
<212> TYPE: DNA
<213> ORGANISM: Adenovirus type 12
<220> FEATURE:
<221> NAME/KEY: misc_feature
```

<223> OTHER INFORMATION: Ad12 proximal pIX upstream sequence
<220> FEATURE:
<221> NAME/KEY: E1B 55K stopcodon
<222> LOCATION: (1)..(3)
<220> FEATURE:
<221> NAME/KEY: pIX startcodon
<222> LOCATION: (81)..(84)

<400> SEQUENCE: 47
tgaggtaagt gggtggagct aggtgggatt ataaaaggct ggaagtcaac taaaaattgt    60
ttttgttctt ttaacagcac gatg                                          84

<210> SEQ ID NO 48
<211> LENGTH: 93
<212> TYPE: DNA
<213> ORGANISM: Adenovirus type 9
<220> FEATURE:
<221> NAME/KEY: misc_feature
<223> OTHER INFORMATION: Ad9 proximal pIX upstream sequence
<220> FEATURE:
<221> NAME/KEY: E1B 55K stopcodon
<222> LOCATION: (1)..(3)
<220> FEATURE:
<221> NAME/KEY: pIX startcodon
<222> LOCATION: (91)..(93)

<400> SEQUENCE: 48
tagaggtagg tcgagtgagt agtgggcgtg gctaaggtga ctataaaggc gggtgtctta    60
cgagggtctt tttgcttttc tgcagacatc atg                                93

<210> SEQ ID NO 49
<211> LENGTH: 73
<212> TYPE: DNA
<213> ORGANISM: Adenovirus type 40
<220> FEATURE:
<221> NAME/KEY: misc_feature
<223> OTHER INFORMATION: Ad40 proximal pIX upstream sequence
<220> FEATURE:
<221> NAME/KEY: E1B 55K stopcodon
<222> LOCATION: (1)..(3)
<220> FEATURE:
<221> NAME/KEY: pIX startcodon
<222> LOCATION: (71)..(73)

<400> SEQUENCE: 49
taagggtaag gggcggagcc tattacaggt ataaaggttg ggtagagta aaaaaaggg      60 aagttacaaa atg                                                      73

<210> SEQ ID NO 50
<211> LENGTH: 90
<212> TYPE: DNA
<213> ORGANISM: Adenovirus type 4
<220> FEATURE:
<221> NAME/KEY: misc_feature
<223> OTHER INFORMATION: Ad4 proximal pIX upstream sequence
<220> FEATURE:
<221> NAME/KEY: E1B 55K stopcodon
<222> LOCATION: (1)..(3)
<220> FEATURE:
<221> NAME/KEY: pIX startcodon
<222> LOCATION: (88)..(90)

<400> SEQUENCE: 50
tagagtgagt agtgttctgg ggcgggggag gacctgcatg agggccagaa taactgaaat    60
ctgtgctttt ctgtgtgttg cagcagcatg                                    90

<210> SEQ ID NO 51

```
<211> LENGTH: 90
<212> TYPE: DNA
<213> ORGANISM: simian Adenovirus type 25
<220> FEATURE:
<221> NAME/KEY: misc_feature
<223> OTHER INFORMATION: sAd25 proximal pIX upstream sequence
<220> FEATURE:
<221> NAME/KEY: E1B 55K stopcodon
<222> LOCATION: (1)..(3)
<220> FEATURE:
<221> NAME/KEY: pIX startcodon
<222> LOCATION: (88)..(90)

<400> SEQUENCE: 51
tagagtgagt agtgttctgg ggcgggggag gacctgcatg agggccagaa taactgaaat      60
ctgtgctttt ctgtgtgttg cagcagcatg                                      90

<210> SEQ ID NO 52
<211> LENGTH: 89
<212> TYPE: DNA
<213> ORGANISM: Adenovirus type 35
<220> FEATURE:
<221> NAME/KEY: misc_feature
<223> OTHER INFORMATION: Ad35 proximal pIX upstream sequence
<220> FEATURE:
<221> NAME/KEY: E1B 55K stopcodon
<222> LOCATION: (1)..(3)
<220> FEATURE:
<221> NAME/KEY: pIX startcodon
<222> LOCATION: (87)..(89)

<400> SEQUENCE: 52
taaggtgagt attgggaaaa ctttggggtg ggattttcag atggacagat tgagtaaaaa      60 tttgttttttt ctgtcttgca gctgacatg                                      89

<210> SEQ ID NO 53
<211> LENGTH: 89
<212> TYPE: DNA
<213> ORGANISM: Adenovirus type 11
<220> FEATURE:
<221> NAME/KEY: misc_feature
<223> OTHER INFORMATION: Ad11 proximal pIX upstream sequence
<220> FEATURE:
<221> NAME/KEY: E1B 55K stopcodon
<222> LOCATION: (1)..(3)
<220> FEATURE:
<221> NAME/KEY: pIX stopcodon
<222> LOCATION: (87)..(89)

<400> SEQUENCE: 53
taaggtgagt attgggaaaa ctttggggtg ggattttcag atggacagat tgagtaaaaa      60 tttgttttttt ctgtcttgca gctgtcatg                                      89

<210> SEQ ID NO 54
<211> LENGTH: 100
<212> TYPE: DNA
<213> ORGANISM: Adenovirus type 7
<220> FEATURE:
<221> NAME/KEY: misc_feature
<223> OTHER INFORMATION: Ad7 proximal pIX upstream sequence
<220> FEATURE:
<221> NAME/KEY: E1B 55K stopcodon
<222> LOCATION: (1)..(3)
<220> FEATURE:
<221> NAME/KEY: pIX startcodon
<222> LOCATION: (98)..(100)

<400> SEQUENCE: 54
taaagtaagt agtgggggca aaatgtggat ggggactttc aggttggtaa ggtggacaaa      60
```

-continued ttgggtaaat tttgttaatt tctgtcttgc agctgccatg          100

<210> SEQ ID NO 55
<211> LENGTH: 2430
<212> TYPE: DNA
<213> ORGANISM: Adenovirus type 35
<220> FEATURE:
<221> NAME/KEY: misc_feature
<223> OTHER INFORMATION: Ad35 E1B-pIX region

<400> SEQUENCE: 55
aataaaaata tgttaactgt tcactggttt ttattgcttt ttgggcgggg actcaggtat      60
ataagtagaa gcagacctgt gtggttagct cataggagct ggctttcatc catggaggtt    120
tgggccattt tggaagacct taggaagact aggcaactgt tagagagcgc ttcgacgga     180
gtctccggtt tttggagatt ctggttcgct agtgaattag ctagggtagt ttttaggata    240
aaacaggact ataaacaaga atttgaaaag ttgttggtag attgcccagg acttttgaa     300
gctcttaatt tgggccatca ggttcacttt aaagaaaaag ttttatcagt tttagacttt    360
tcaaccccag gtagaactgc tgctgctgtg gcttttctta cttttatatt agataaatgg    420
atcccgcaga ctcatttcag caggggatac gttttggatt tcatagccac agcattgtgg    480
agaacatgga aggttcgcaa gatgaggaca atcttaggtt actggccagt gcagcctttg    540
ggtgtagcgg gaatcctgag gcatccaccg gtcatgccag cggttctgga ggaggaacag    600
caagaggaca acccgagagc cggcctggac cctccagtgg aggaggcgga gtagctgact    660
tgtctcctga actgcaacgg gtgcttactg gatctacgtc cactggacgg gatagggggcg    720
ttaagaggga gagggcatcc agtggtactg atgctagatc tgagttggct ttaagtttaa    780
tgagtcgcag acgtcctgaa accatttggt ggcatgaggt tcagaaagag ggaagggatg    840
aagtttctgt attgcaggag aaatattcac tggaacaggg gaaaacatgt tggttggagc    900
cagaggatga ttgggcggtg gccattaaaa attatgccaa gatagctttg aggcctgata    960
aacagtataa gatcagtaga cggattaata tccggaatgc ttgttacata tctggaaatg   1020
gggctgaggt ggtaatagat actcaagaca agacagttat tagatgctgc atgatggata   1080
tgtggcctgg agtagtcggt atggaagcag tcacttttgt aaatgttaag tttaggggag   1140
atggttataa tggaatagtg tttatggcca ataccaaact tatattgcat ggttgtagct   1200
ttttttggtt caacaatacc tgtgtagatg cctggggaca ggttagtgta cgggggtgta   1260
gtttctatgc gtgttggatt gccacagctg gcagaaccaa gagtcaattg tctctgaaga   1320
aatgcatatt ccaaagatgt aacctgggca ttctgaatga aggcgaagca agggtccgtc   1380
actgcgcttc tacagatact ggatgtttta ttttaattaa gggaaatgcc agcgtaaagc   1440
ataacatgat ttgtggtgct tccgatgaga ggccttatca aatgctcact tgtgctggtg   1500
ggcattgtaa tatgctggct actgtgcata ttgtttccca tcaacgcaaa aaatggcctg   1560
tttttgatca caatgtgttg accaagtgca ccatgcatgc aggtgggcgt agaggaatgt   1620
ttatgcctta ccagtgtaac atgaatcatg tgaaagtgtt gttggaacca gatgcctttt   1680
ccagaatgag cctaacagga atctttgaca tgaacacgca atctggaag atcctgaggt    1740
atgatgatac gagatcgagg gtgcgcgcat gcgaatgcgg aggcaagcat gccaggttcc   1800
agccggtgtg tgtagatgtg accgaagatc tcagaccgga tcatttggtt attgcccgca   1860
ctggagcaga gttcggatcc agtggagaag aaactgacta aggtgagtat tgggaaaact   1920
ttggggtggg attttcagat ggacagattg agtaaaaatt tgtttttttct gtcttgcagc   1980

-continued

```
tgacatgagt ggaaatgctt cttttaaggg gggagtcttc agcccttatc tgacagggcg   2040
tctcccatcc tgggcaggag ttcgtcagaa tgttatggga tctactgtgg atggaagacc   2100
cgttcaaccc gccaattctt caacgctgac ctatgctact ttaagttctt cacctttgga   2160
cgcagctgca gccgctgccg ccgcctctgt cgccgctaac actgtgcttg aatgggtta    2220 ctatggaagc atcgtggcta attccacttc ctctaataac ccttctacac tgactcagga   2280
caagttactt gtccttttgg cccagctgga ggctttgacc caacgtctgg gtgaactttc   2340
tcagcaggtg gccgagttgc gagtacaaac tgagtctgct gtcggcacgg caaagtctaa   2400
ataaaaaaaa ttccagaatc aatgaataaa                                    2430
```

<210> SEQ ID NO 56
<211> LENGTH: 2429
<212> TYPE: DNA
<213> ORGANISM: Adenovirus type 11
<220> FEATURE:
<221> NAME/KEY: misc_feature
<223> OTHER INFORMATION: Ad11 E1B-pIX region

<400> SEQUENCE: 56

```
aataaaaata tgttaactgt tcactggttt ttattgcttt ttgggcgggg actcaggtat     60
ataagtagaa gcagacctgt gtggttagct cataggagct ggctttcatc catgtgaggtt   120 tgggccattt tggaagacct taggaagact aggcaactgt tagagaacgc ttcggacgga    180
gtctccggtt tttggagatt ctggttcgct agtgaattag ctagggtagt ttttaggata    240
aaacaggact ataaacaaga atttgaaaag ttgttggtag attgcccagg acttttttgaa   300 gctcttaatt tgggccatca ggttcacttt aaagaaaaag ttttatcagt tttagacttt    360 tcaacccag gtagaactgc tgctgctgtg cttttctta cttttatatt agataaatgg      420
atcccgcaga ctcatttcag caggggatac gttttggatt tcatagccac agcattgtgg    480
agaacatgga aggttcgcaa gatgaggaca atcttaggtt actggccagt gcagcctttg    540
ggtgtagcgg gaatcctgag gcatccaccg gtcatgccag cggttctgga ggaggaacag    600
caagaggaca acccgagagc cggcctggac cctccagtgg aggagcgga gtagctgact     660 tgtctcctga actgcaacgg gtgcttactg gatctacgtc cactggacgg gataggggcg    720
ttaagaggga gagggcatct agtggtactg atgctagatc tgagttggct ttaagtttaa    780
tgagtcgcag acgtcctgaa accatttggt ggcatgaggt tcagaaagag ggaagggatg    840
aagtttctgt attgcaggag aaatattcac tggaacaggt gaaaacatgt tggttggagc    900
ctgaggatga ttgggaggtg gccattaaaa attatgccaa gatagctttg aggcctgata    960
aacagtataa gattactaga cggattaata tccggaatgc ttgttacata tctggaaatg   1020
gggctgaggt ggtaatagat actcaagaca aggcagttat tagatgctgc atgatggata   1080
tgtggcctgg ggtagtcggt atggaagcag taacttttgt aaatgttaag tttaggggag   1140
atggttataa tggaatagtg tttatggcca ataccaaact tatattgcat ggttgtagct   1200
tttttggttt caacaatacc tgtgtagatg cctggggaca ggttagtgta cgggatgta    1260 gtttctatgc gtgttggatt gccacagctg gcagaaccaa gagtcaattg tctctgaaga   1320
aatgcatatt tcaaagatgt aacctgggca ttctgaatga aggcgaagca agggtccgcc   1380
actgcgcttc tacagatact ggatgtttta ttttgattaa gggaaatgcc agcgtaaagc   1440
ataacatgat ttgcggtgct tccgatgaga ggccttatca aatgctcact tgtgctggtg   1500
ggcattgtaa tatgctggct actgtgcata ttgtttccca tcaacgcaaa aaatggcctg   1560
```

-continued

```
tttttgatca caatgtgatg acgaagtgta ccatgcatgc aggtgggcgt agaggaatgt    1620
ttatgcctta ccagtgtaac atgaatcatg tgaaagtgtt gttggaacca gatgcctttt    1680
ccagaatgag cctaacagga attttttgaca tgaacatgca aatctggaag atcctgaggt   1740
atgatgatac gagatcgagg gtacgcgcat gcgaatgcgg aggcaagcat gccaggttcc    1800
agccggtgtg tgtagatgtg actgaagatc tcagaccgga tcatttggtt attgcccgca    1860
ctggagcaga gttcggatcc agtggagaag aaactgacta aggtgagtat gggaaaact    1920 ttggggtggg atttcagat ggacagattg agtaaaaatt tgtttttcct gtcttgcagc     1980
tgtcatgagt ggaaacgctt cttttaaggg gggagtcttc agcccttatc tgacagggcg    2040
tctcccatcc tgggcaggag ttcgtcagaa tgttatggga tctactgtgg atggaagacc    2100
cgtccaaccc gccaattctt caacgctgac ctatgctact ttaagttctt cacctttgga   2160
cgcagctgca gctgccgccg ccgcttctgt tgccgctaac actgtgcttg aatgggtta    2220 ctatggaagc atcatggcta attccacttc ctctaataac ccttctaccc tgactcagga   2280
caagttactt gtccttttgg cccagctgga ggctttgacc caacgtctgg gtgaactttc   2340
tcagcaggtg gtcgagttgc gagtacaaac tgagtctgct gtcggcacgg caaagtctaa    2400
ataaaaaaat cccagaatca atgaataaa                                      2429
```

<210> SEQ ID NO 57
<211> LENGTH: 2426
<212> TYPE: DNA
<213> ORGANISM: Adenovirus type 7
<220> FEATURE:
<221> NAME/KEY: misc_feature
<223> OTHER INFORMATION: Ad7 E1B-pIX region

<400> SEQUENCE: 57

```
aataaaatta tgtcagctgc tgagtgtttt attacttctt gggtggggtc ttggatatat     60
aagtaggagc agatctgtgt ggttagctca cagcaacttg ctgccatcca tggaggtttg    120
ggctatcttg gaagacctca gacagactag gctactacta gaaaacgcct cggacggagt    180
ctctggcctt tggagattct ggttcggtgg tgatctagct aggctagtgt ttaggataaa    240
acaggactac agggaagaat ttgaaaagtt attggacgac attccaggac ttttgaagc    300 tcttaacttg ggccatcagg ctcattttaa ggagaaggtt ttatcagttt tagattttc    360 tactcctggt agaactgctg ctgctgtagc ttttcttact tttatattgg ataaatggat    420
ccgccaaact cacttcagca agggatacgt tttggatttc atagcagcag cttttgtggag   480 aacatggaag gctcgcagga tgaggacaat cttagattac tggccagtgc agcctctggg    540
agtagcaggg atactgagac acccaccgac catgccagcg gttctgcagg aggagcagca    600
ggaggacaat ccgagagccg gcctggaccc tccggtggag gagtagctga cctgtttcct    660
gaactgcgac gggtgcttac taggtctacg accagtggac agaacagggg aattaagagg    720
gagaggaatc ctagtgggaa taattcaaga accgagttgg ctttaagttt aatgagccgc    780
aggcgtcctg aaactgtttg gtggcatgag gttcagagcg aaggcaggga tgaagtttca    840
atattgcagg agaaatattc actagaacaa cttaagacct gttggttgga acctgaggat    900
gattgggagg tggccattag gaattatgct aagatatctc tgaggcctga taacaatat    960 agaattacta agaagattaa tattagaaat gcatgctaca tatcagggaa tggggcagag    1020
gttataatag atacacaaga taagcagct tttgatgtt gtatgatggg tatgtggcca    1080
ggggttgtcg gcatggaagc aataacactt atgaatatta ggtttagagg ggatgggtat    1140
```

-continued

```
aatggcattg tatttatggc taacactaag ctgattctac atggttgtag cttttttggg      1200
tttaataata cgtgtgtaga agcttggggg caagttagtg tgagggggttg tagtttttat    1260 gcatgctgga ttgcaacatc aggtagggtg aagagtcagt tgtctgtgaa gaaatgcatg    1320
tttgagagat gtaatcttgg catactgaat gaaggtgaag caagggtccg ccactgcgca    1380
gctacagaaa ctgcctgctt cattctaata aagggaaatg ccagtgtgaa gcataatatg    1440
atctgtggac attcggatga gaggccttat cagatgctaa cctgcgctgg tggacattgc    1500
aatattcttg ctaccgtgca tatcgtttca catgcacgca agaaatggcc tgtatttgaa    1560
cataatgtga ttaccaagtg caccatgcat ataggtggtc gcagggaat gtttatgcct     1620 taccagtgta acatgaatca tgtgaaggta atgttggaac cagatgcctt ttccagagtg    1680
agcgtaacag gaatctttga tatgaatatt caactatgga agatcctgag atatgatgac   1740
actaaaccaa gggtgcgcgc atgcgaatgc ggaggcaagc atgctagatt ccagccggtg    1800
tgcgtggatg tgactgaaga cctgaggccc gatcatttgg tgcttgcctg cactggagcg    1860
gagttcggtt ctagtggtga agaaactgac taaagtaagt agtgggggca aaatgtggat    1920
ggggactttc aggttggtaa ggtggacaaa ttgggtaaat tttgttaatt tctgtcttgc    1980
agctgccatg agtggaagcg cttcttttga gggggggagta tttagccctt atctgacggg    2040
caggctccca ccatgggcag gagttcgtca gaatgtcatg ggatccactg tggatgggag    2100
acccgtccag cccgccaatt cctcaacgct gacctatgcc actttgagtt cgtcaccatt    2160
ggatgcagct gcagccgccg ccgctactgc tgccgccaac accatccttg gaatgggcta    2220
ttacggaagc attgttgcca attccagttc ctctaataat ccttcaaccc tggctgagga    2280
caagctactt gttctcttgg ctcagctcga ggccttaacc caacgcttag gcgaactgtc    2340
taagcaggtg gcccagttgc gtgagcaaac tgagtctgct gttgccacag caaagtctaa    2400
ataaagatct caaatcaata aataaa                                         2426
```

<210> SEQ ID NO 58
<211> LENGTH: 240
<212> TYPE: DNA
<213> ORGANISM: Adenovirus type 11
<220> FEATURE:
<221> NAME/KEY: misc_feature
<223> OTHER INFORMATION: Ad11 pIX cDNA sequence

<400> SEQUENCE: 58

```
cgactggagc acgaggacac tgacatggac tgaaggagta gaaatcattt ggttattgcc      60
cgcactggag cagagttcgg atccagtgga aagaaactg actaagctgt catgagtgga     120
aacgcttctt ttaaggggggg agtcttcagc ccttatctga cagggcgtct cccatcctgg     180
gcaggagttc gtcagaatgt tatgggatct actgtggatg gaacacccgt tcaacccgcc    240
```

<210> SEQ ID NO 59
<211> LENGTH: 227
<212> TYPE: DNA
<213> ORGANISM: Adenovirus type 35
<220> FEATURE:
<221> NAME/KEY: misc_feature
<223> OTHER INFORMATION: Ad35 pIX cDNA sequence

<400> SEQUENCE: 59

```
ggacactgac atggactgaa ggagtagaaa tcatttggt tattgcccgc actggagcag       60
agttcggatc cagtggagaa gaaactgact aagctgacat gagtggaaat gcttctttta    120
```

-continued

```
agggggagt cttcagccct tatctgacag gcgtctccc atcctgggca ggagttcgtc      180
agaatgttat gggatctact gtggatggaa gacccgttca acccgcc                  227
```

<210> SEQ ID NO 60
<211> LENGTH: 289
<212> TYPE: DNA
<213> ORGANISM: Adenovirus type 35
<220> FEATURE:
<221> NAME/KEY: misc_feature
<223> OTHER INFORMATION: wild-type Ad35 sequence nt 3339-3628
<220> FEATURE:
<221> NAME/KEY: Intron
<222> LOCATION: (62)..(138)
<220> FEATURE:
<221> NAME/KEY: startcodon pIX
<222> LOCATION: (146)..(148)

<400> SEQUENCE: 60

```
atcatttggt tattgcccgc actggagcag agttcggatc cagtggagaa gaaactgact      60
aaggtgagta ttgggaaaac tttggggtgg gattttcaga tggacagatt gagtaaaaat    120
ttgttttttc tgtcttgcag ctgacatgag tggaaatgct tcttttaagg ggggagtctt    180
cagcccttat ctgacagggc gtctcccatc ctgggcagga gttcgtcaga atgttatggg    240
atctactgtg gatggaagac ccgttcaacc cgccaattct tcaacgctg                289
```

<210> SEQ ID NO 61
<211> LENGTH: 294
<212> TYPE: PRT
<213> ORGANISM: Adenovirus type 5
<220> FEATURE:
<221> NAME/KEY: MISC_FEATURE
<223> OTHER INFORMATION: amino acid sequence of the E4-orf6 protein of Ad5

<400> SEQUENCE: 61

```
Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

Pro Glu Cys Asn Thr Leu Thr Met His Asn Val Ser Tyr Val Arg Gly
    50                  55                  60

Leu Pro Cys Ser Val Gly Phe Thr Leu Ile Gln Glu Trp Val Val Pro
65                  70                  75                  80

Trp Asp Met Val Leu Thr Arg Glu Glu Leu Val Ile Leu Arg Lys Cys
                85                  90                  95

Met His Val Cys Leu Cys Cys Ala Asn Ile Asp Ile Met Thr Ser Met
            100                 105                 110

Met Ile His Gly Tyr Glu Ser Trp Ala Leu His Cys His Cys Ser Ser
        115                 120                 125

Pro Gly Ser Leu Gln Cys Ile Ala Gly Gly Gln Val Leu Ala Ser Trp
    130                 135                 140

Phe Arg Met Val Val Asp Gly Ala Met Phe Asn Gln Arg Phe Ile Trp
145                 150                 155                 160

Tyr Arg Glu Val Val Asn Tyr Asn Met Pro Lys Glu Val Met Phe Met
                165                 170                 175

Ser Ser Val Phe Met Arg Gly Arg His Leu Ile Tyr Leu Arg Leu Trp
            180                 185                 190
```

```
Tyr Asp Gly His Val Gly Ser Val Pro Ala Met Ser Phe Gly Tyr
        195                 200                 205

Ser Ala Leu His Cys Gly Ile Leu Asn Asn Ile Val Leu Cys Cys
        210                 215                 220

Ser Tyr Cys Ala Asp Leu Ser Glu Ile Arg Val Arg Cys Cys Ala Arg
225                 230                 235                 240

Arg Thr Arg Arg Leu Met Leu Arg Ala Val Arg Ile Ile Ala Glu Glu
                245                 250                 255

Thr Thr Ala Met Leu Tyr Ser Cys Arg Thr Glu Arg Arg Gln Gln
                260                 265                 270

Phe Ile Arg Ala Leu Leu Gln His Arg Pro Ile Leu Met His Asp
            275                 280                 285

Tyr Asp Ser Thr Pro Met
        290

<210> SEQ ID NO 62
<211> LENGTH: 299
<212> TYPE: PRT
<213> ORGANISM: Adenovirus type 35
<220> FEATURE:
<221> NAME/KEY: MISC_FEATURE
<223> OTHER INFORMATION: amino acid sequence of the E4-orf6 protein of
      Ad35

<400> SEQUENCE: 62

Met Ser Gly Ser Asn Ser Ile Met Thr Arg Leu Arg Ala Arg Ser Thr
1               5                   10                  15

Ser Cys Ala Arg His His Pro Tyr Thr Arg Ala Gln Leu Pro Arg Cys
            20                  25                  30

Glu Glu Asn Glu Thr Arg Ala Ser Met Thr Glu Asp His Pro Leu Leu
        35                  40                  45

Pro Asp Cys Asp Thr Met Thr Met His Ser Val Ser Cys Val Arg Gly
    50                  55                  60

Leu Pro Cys Ser Ala Ser Phe Thr Val Leu Gln Glu Leu Pro Ile Pro
65                  70                  75                  80

Trp Asp Met Phe Leu Asn Pro Glu Glu Leu Lys Ile Met Arg Arg Cys
                85                  90                  95

Met His Leu Cys Leu Cys Cys Ala Thr Ile Asp Ile Phe His Ser Gln
            100                 105                 110

Val Ile His Gly Arg Glu Asn Trp Val Leu His Cys His Cys Asn Gln
        115                 120                 125

Gln Gly Ser Leu Gln Cys Met Ala Gly Gly Ala Val Leu Ala Val Trp
    130                 135                 140

Phe Arg Lys Val Ile Leu Gly Cys Met Ile Asn Gln Arg Cys Pro Trp
145                 150                 155                 160

Tyr Arg Gln Ile Val Asn Met His Met Pro Lys Glu Ile Met Tyr Val
                165                 170                 175

Gly Ser Val Phe Leu Arg Glu Arg His Leu Ile Tyr Ile Lys Leu Trp
            180                 185                 190

Tyr Asp Gly His Ala Gly Ala Ile Ile Ser Asp Met Ser Phe Gly Trp
        195                 200                 205

Ser Ala Phe Asn Tyr Gly Leu Leu Asn Asn Ile Val Ile Met Cys Cys
    210                 215                 220

Thr Tyr Cys Lys Asp Leu Ser Glu Ile Arg Met Arg Cys Cys Ala His
225                 230                 235                 240

Arg Thr Arg Lys Leu Met Leu Arg Ala Ile Lys Ile Met Leu Gln Glu
```

-continued

```
                245                 250                 255
Thr Val Asp Pro Asp Pro Ile Asn Ser Ser Arg Thr Glu Arg Arg
            260                 265                 270

Gln Arg Leu Leu Val Gly Leu Met Arg His Asn Arg Pro Ile Pro Phe
        275                 280                 285

Ser Asp Tyr Asp Ser His Arg Ser Ser Ser Arg
    290                 295

<210> SEQ ID NO 63
<211> LENGTH: 150
<212> TYPE: PRT
<213> ORGANISM: Adenovirus type 5
<220> FEATURE:
<221> NAME/KEY: misc_feature
<223> OTHER INFORMATION: amino acid sequence of the E4-orf6+7 protein of
      Ad5

<400> SEQUENCE: 63

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

Pro Glu Cys Asn Thr Leu Thr Met His Asn Ala Trp Thr Ser Pro Ser
    50                  55                  60

Pro Pro Val Lys Gln Pro Gln Val Gly Gln Pro Val Ala Gln Gln
65                  70                  75                  80

Leu Asp Ser Asp Met Asn Leu Ser Glu Leu Pro Gly Glu Phe Ile Asn
                85                  90                  95

Ile Thr Asp Glu Arg Leu Ala Arg Gln Glu Thr Val Trp Asn Ile Thr
            100                 105                 110

Pro Lys Asn Met Ser Val Thr His Asp Met Met Leu Phe Lys Ala Ser
        115                 120                 125

Arg Gly Glu Arg Thr Val Tyr Ser Val Cys Trp Glu Gly Gly Gly Arg
    130                 135                 140

Leu Asn Thr Arg Val Leu
145                 150

<210> SEQ ID NO 64
<211> LENGTH: 141
<212> TYPE: PRT
<213> ORGANISM: Adenovirus type 35
<220> FEATURE:
<221> NAME/KEY: misc_feature
<223> OTHER INFORMATION: amino acid sequence of the E4-orf6+7 protein of
      Ad35

<400> SEQUENCE: 64

Met Ser Gly Ser Asn Ser Ile Met Thr Arg Leu Arg Ala Arg Ser Thr
1               5                   10                  15

Ser Cys Ala Arg His His Pro Tyr Thr Arg Ala Gln Leu Pro Arg Cys
            20                  25                  30

Glu Glu Asn Glu Thr Arg Ala Ser Met Thr Glu Asp His Pro Leu Leu
        35                  40                  45

Pro Asp Cys Asp Thr Met Thr Met His Ser Met Thr Val Ile Gln Thr
    50                  55                  60

Pro Glu Ser His Pro Gln Gln Leu Asp Cys Glu Ser Ala Leu Lys Asp
65                  70                  75                  80
```

Tyr Arg Asp Gly Phe Leu Ser Ile Thr Asp Pro Arg Leu Ala Arg Ser
                85                  90                  95

Glu Thr Val Trp Asn Val Glu Ser Lys Thr Met Ser Ile Ser Asn Gly
            100                 105                 110

Ile Gln Met Phe Lys Ala Val Arg Gly Glu Arg Leu Val Tyr Ser Val
        115                 120                 125

Lys Trp Glu Gly Gly Lys Ile Thr Thr Arg Ile Leu
    130                 135                 140

<210> SEQ ID NO 65
<211> LENGTH: 150
<212> TYPE: PRT
<213> ORGANISM: Artificial
<220> FEATURE:
<223> OTHER INFORMATION: amino acid sequence of the E4-orf6+7 fusion
      protein from Ad5 and Ad35

<400> SEQUENCE: 65

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

Pro Glu Cys Asn Thr Leu Thr Met His Asn Ala Trp Thr Ser Pro Ser
    50                  55                  60

Pro Pro Val Lys Gln Pro Gln Val Gly Gln Gln Pro Val Ala Gln Gln
65                  70                  75                  80

Leu Asp Ser Asp Met Asn Leu Ser Glu Leu Pro Gly Glu Phe Ile Asn
            85                  90                  95

Ile Thr Asp Glu Arg Leu Ala Arg Gln Glu Thr Val Trp Asn Ile Thr
        100                 105                 110

Pro Lys Asn Met Ser Val Thr His Asp Met Met Leu Phe Lys Ala Ser
        115                 120                 125

Arg Gly Glu Arg Thr Val Tyr Ser Val Lys Trp Glu Gly Gly Gly Lys
    130                 135                 140

Ile Thr Thr Arg Ile Leu
145                 150